United States Patent
Nagatsuka et al.

(10) Patent No.: US 11,512,203 B2
(45) Date of Patent: Nov. 29, 2022

(54) WATER-SOLUBLE AZO COMPOUND OR SALT THEREOF, INK AND RECORDING MEDIUM

(71) Applicant: Nippon Kayaku Kabushiki Kaisha, Tokyo (JP)

(72) Inventors: Shinya Nagatsuka, Tokyo (JP); Taku Iino, Tokyo (JP); Hitomi Muto, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 825 days.

(21) Appl. No.: 16/336,826

(22) PCT Filed: Oct. 20, 2017

(86) PCT No.: PCT/JP2017/038038
§ 371 (c)(1),
(2) Date: Mar. 26, 2019

(87) PCT Pub. No.: WO2018/079442
PCT Pub. Date: May 3, 2018

(65) Prior Publication Data
US 2021/0292566 A1      Sep. 23, 2021

(30) Foreign Application Priority Data

| Oct. 31, 2016 | (JP) | JP2016-213232 |
| Oct. 31, 2016 | (JP) | JP2016-213233 |
| Oct. 31, 2016 | (JP) | JP2016-213234 |
| Oct. 31, 2016 | (JP) | JP2016-213238 |
| Feb. 10, 2017 | (JP) | JP2017-023615 |
| Feb. 10, 2017 | (JP) | JP2017-023616 |
| Feb. 10, 2017 | (JP) | JP2017-023617 |
| Feb. 10, 2017 | (JP) | JP2017-023618 |
| Feb. 10, 2017 | (JP) | JP2017-023619 |
| Feb. 10, 2017 | (JP) | JP2017-023620 |

(51) Int. Cl.
| C09D 11/00   | (2014.01) |
| C09B 43/16   | (2006.01) |
| B41J 2/175   | (2006.01) |
| B41M 5/00    | (2006.01) |
| B41M 5/50    | (2006.01) |
| C07D 251/70  | (2006.01) |
| C07D 405/12  | (2006.01) |
| C09D 11/033  | (2014.01) |
| C09D 11/037  | (2014.01) |
| C09D 11/328  | (2014.01) |
| C09D 11/36   | (2014.01) |
(Continued)

(52) U.S. Cl.
CPC .......... C09B 43/16 (2013.01); B41J 2/17503 (2013.01); B41M 5/0023 (2013.01); B41M 5/502 (2013.01); C07D 251/70 (2013.01); C07D 405/12 (2013.01); C09D 11/033 (2013.01); C09D 11/037 (2013.01); C09D 11/328 (2013.01); C09D 11/36 (2013.01)

(58) Field of Classification Search
USPC ...................... 106/31.01, 31.13, 31.27, 31.43
See application file for complete search history.

(56) References Cited

U.S. PATENT DOCUMENTS

| 5,560,771 A     | 10/1996 | Takemoto     |
| 2002/0050225 A1 | 5/2002  | Mafune et al. |
(Continued)

FOREIGN PATENT DOCUMENTS

| JP | H11-070729 | 3/1999  |
| JP | 3346755    | 11/2002 |
(Continued)

OTHER PUBLICATIONS

Office Action issued in Indian Patent Application No. 201917012175, dated Oct. 22, 2020.
(Continued)

*Primary Examiner* — James E McDonough
(74) *Attorney, Agent, or Firm* — Knobbe, Martens, Olson & Bear LLP

(57) ABSTRACT

A compound represented by formula (1) or a salt thereof, and an ink including the same. In formula (1), each Q independently represents a halogen atom; $R^{11}$ and $R^{12}$ independently represent an alkyl group substituted by an ionic hydrophilic group; and $A^1$ represents a C1-C3 alkoxy-substituted alkylamino group (1)

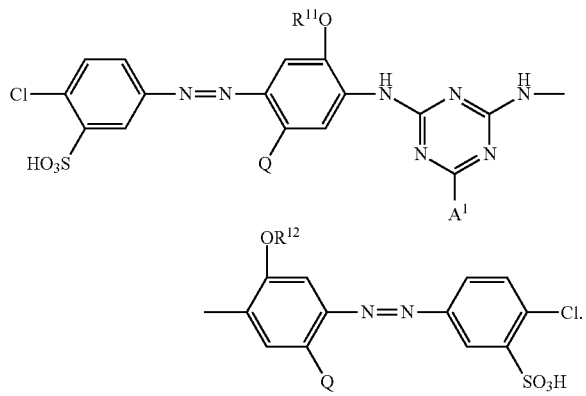

8 Claims, No Drawings

(51) Int. Cl.
   *C09D 1/00*   (2006.01)
   *C09D 4/00*   (2006.01)
   *C09D 5/00*   (2006.01)

(56) References Cited

U.S. PATENT DOCUMENTS

| | | |
|---|---|---|
| 2010/0118067 A1 | 5/2010 | Morita et al. |
| 2012/0037037 A1 | 2/2012 | Morita et al. |
| 2012/0202019 A1 | 8/2012 | Matsui et al. |
| 2013/0002757 A1 | 1/2013 | Aruga et al. |

FOREIGN PATENT DOCUMENTS

| | | |
|---|---|---|
| JP | 4100880 | 6/2008 |
| JP | 2012-246342 A | 12/2012 |
| JP | 2013-010825 | 1/2013 |
| JP | 2013-018849 A | 1/2013 |
| JP | 2014-118437 | 6/2014 |
| JP | 2014-118439 | 6/2014 |
| JP | 2016-098274 A | 5/2016 |
| JP | 2016-098276 A | 5/2016 |
| KR | 10-2012-0083904 A | 7/2012 |
| WO | WO 2008/142989 A1 | 11/2008 |
| WO | WO 2010/125903 A1 | 4/2010 |
| WO | WO 2011/043184 A1 | 4/2011 |
| WO | WO 2011/068046 A1 | 6/2011 |
| WO | WO 2011/122427 A1 | 10/2011 |
| WO | WO-2011122427 A1 * 10/2011 ........... C07D 251/70 |
| WO | WO 2012/099059 | 7/2012 |
| WO | WO-2012099059 A1 * 7/2012 ........... C07D 251/70 |

OTHER PUBLICATIONS

Partial Supplemental European Search Report issued in European Patent Application No. 17864034.8, dated Jun. 15, 2020.

* cited by examiner

WATER-SOLUBLE AZO COMPOUND OR SALT THEREOF, INK AND RECORDING MEDIUM

This application is the U.S. National Phase under 35 U.S.C. § 371 of International Application PCT/JP2017/038038, filed Oct. 20, 2017, designating the U.S., and published in Japanese as WO 2018/079442 on May 3, 2018 which claims priority to Japanese Patent Application Nos. 2016-213232, 2016-213233, 2016-213234, and 2016-213238, all filed Oct. 31, 2016; and to Japanese Patent Application Nos. 2017-023615, 2017-023616, 2017-023617, 2017-023618, 2017-023619, and 2017-023620, all filed Feb. 10, 2017, the entire contents of which are incorporated herein by reference.

TECHNICAL FIELD

The present invention relates to a water-soluble azo compound or a salt thereof, an ink containing the water-soluble azo compound or a salt thereof, a method of ink-jet recording with the ink, an ink-jet printer having a container for the ink, and a recording medium on which the water-soluble azo compound or a salt thereof or the ink is attached.

BACKGROUND ART

Various ink discharging systems have been developed for a method of recording with an ink-jet printer, which is one of representative methods of various color recording methods. These systems all involve generating a droplet of ink, which is then allowed to attach to various recording media (paper, film, textile and the like), thereby performing recording. This method is quiet since a recording head does not make direct contact with a recording medium, generating no sound. Further, these systems, which can easily be downsized, accelerated, and adapted to full-color, have become increasingly popular in recent years, and significant and continuous growth is expected.

Conventionally, coloring matters for use in various recording inks that find their uses in fountain pens felt-tip pens, ink-jet recording and the like may be classified broadly into two groups: water-soluble and water-insoluble coloring matters. Water-soluble coloring matters include direct dyes, acid dyes, reactive dyes and the like. Water-insoluble coloring matters include pigments, disperse dyes, solvent dyes and the like. Among these coloring matters, dyes are thought to have excellent color saturation and the like as compared with pigments, leading to high quality recorded images.

However, the robustness of recorded images such as light resistance may be inferior as compared with that of pigments.

The term "light resistance" as used herein refers to being resistant to a phenomenon where a coloring matter attached on a recorded image will undergo degradation due to exposure to various types of light such as sunlight and light from fluorescent lamps, resulting in discoloration of the recorded image. As one of the features of ink-jet recording, mentioned is the ability of producing photo-quality recorded images. As one of the methods of obtaining a photo-quality recorded image, mentioned is the use of a recording medium having an ink receiving layer. Such an ink receiving layer generally includes a porous white inorganic substance in order to achieve rapid drying of an ink, and obtain a high-quality image with less color blurring. Nonetheless, a significant light-induced discoloring phenomenon may be observed in such a recording medium. For this reason, improving light resistance of recorded images is considered as one of the most important technical issues in the art of ink-jet recording.

Patent Documents 1 to 3 disclose C.I. Direct Yellow 132 as a known yellow coloring matter for ink-jet with excellent water solubility and vividness. Moreover, Patent Document 4 discloses a yellow coloring matter for ink-jet that is excellent in terms of various aspects of robustness.

Patent Document 1: Japanese Unexamined Patent Application, Publication No. H11-70729
Patent Document 2: Japanese Patent No. 3346755
Patent Document 3: Japanese Patent No. 4100880
Patent Document 4: PCT International Publication No. WO2011/122427

DISCLOSURE OF THE INVENTION

Problems to be Solved by the Invention

An object of the present invention is to provide a water-soluble azo compound capable of producing a recorded image with excellent light resistance, and a yellow ink containing the above compound for use in various types of recording, in particular an ink-jet recording purpose.

Means for Solving the Problems

After conducting extensive studies to solve the above described problems, the present inventors have found that a specific water-soluble azo compound represented by the following formula and an ink containing the above compound can solve the above problems, leading to the completion of the present invention.

That is, the present invention relates to the following 1) to 30).

1) A compound represented by the following formula (1) or (2) or a salt thereof:

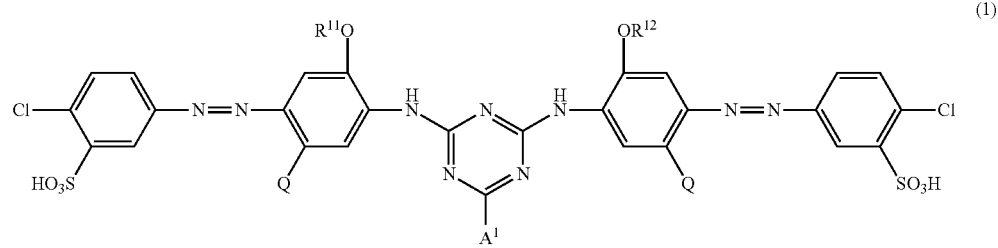

(1)

in which, each Q independently represents a halogen atom, each $R^{11}$ and $R^{12}$ independently represents an alkyl group substituted with an ionic hydrophilic group, and $A^1$ is a group represented by the following formula (A1-1), a group represented by the following formula (A1-2), a C1-C3 alkoxy-substituted alkylamino group, a C1-C6 alkyl-monosubstituted amino group, a C2-C6 alkyl-monosubstituted amino group having two or more hydroxy groups, a group represented by the following formula (A1-3), a group represented by the following formula (A1-4), or a cyclic amine group,

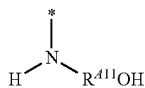

(A1-1)

in which, $R^{411}$ represents a branched alkylene group, and the symbol "*" indicates a position of attachment to a triazine ring,

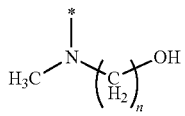

(A1-2)

In which, n represents an integer of 1 to 6, and the symbol "*" indicates a position of attachment to the triazine ring,

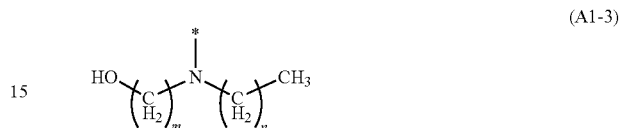

(A1-3)

in which, m represents an integer of 1 to 6, n represents an integer of 1 to 5, and the symbol "*" indicates a position of attachment to the triazine ring,

(A1-4)

in which, n represents an integer of 2 to 6, and the symbol "*" indicates a position of attachment to the triazine ring,

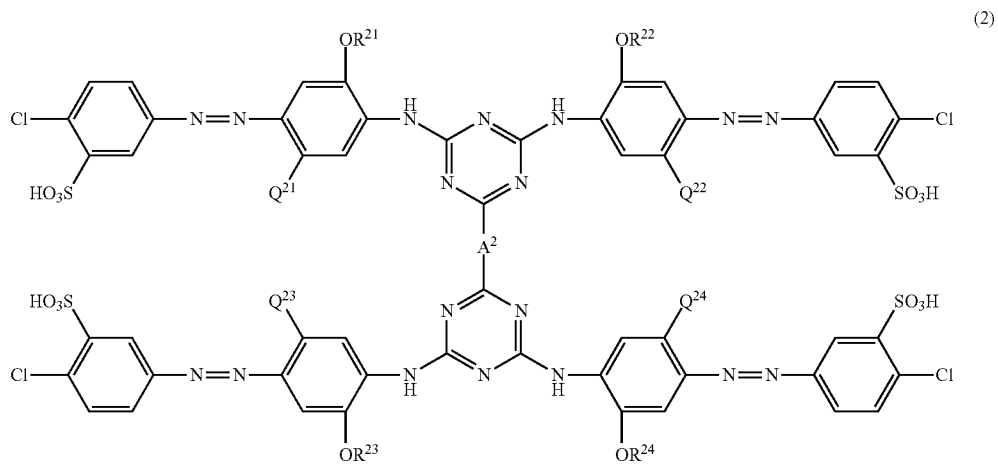

(2)

in which, each $Q^{21}$ to $Q^{24}$ independently represents a halogen atom, and each $R^{21}$ to $R^{24}$ independently represents an alkyl group substituted with an ionic hydrophilic group, and $A^2$ represents a divalent group.

2) The compound or a salt thereof according to 1), in which the compound represented by the formula (1) is represented by the following formula (1-1):

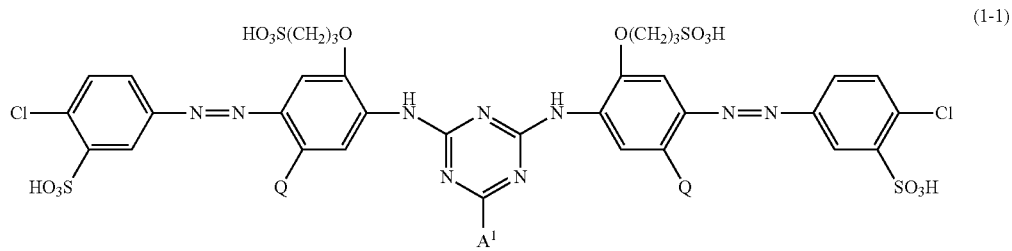
(1-1)

in which, Q and $A^1$ have the same meanings as defined in the formula (1), and each x independently represents an integer of 2 to 4.

3) The compound or a salt thereof according to 2), in which in the formula (1-1), Q is a chlorine atom.

4) The compound or a salt thereof according to 2) or 3), in which in the formula (1-1), x is 3.

5) The compound or a salt thereof according to 1), in which the compound represented by the formula (1) is represented by any of the following formulae (1-11) to (1-15):

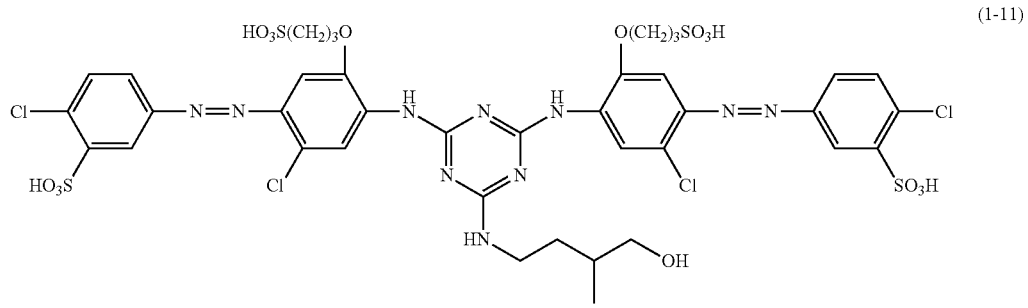
(1-11)

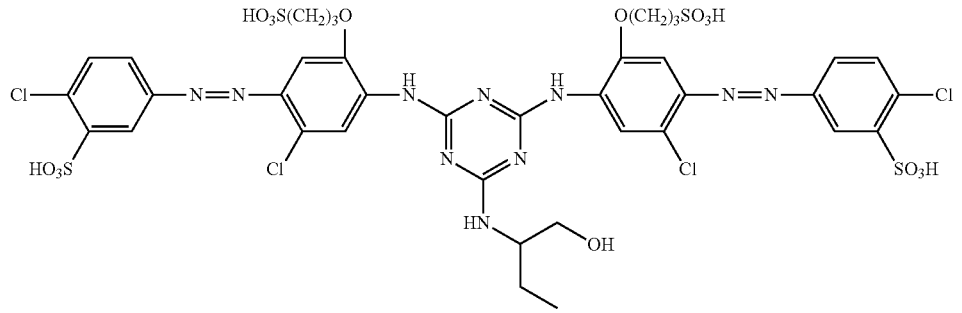
(1-12)

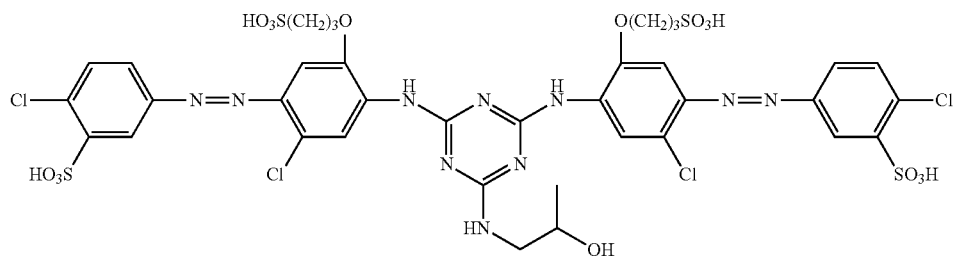
(1-13)

-continued

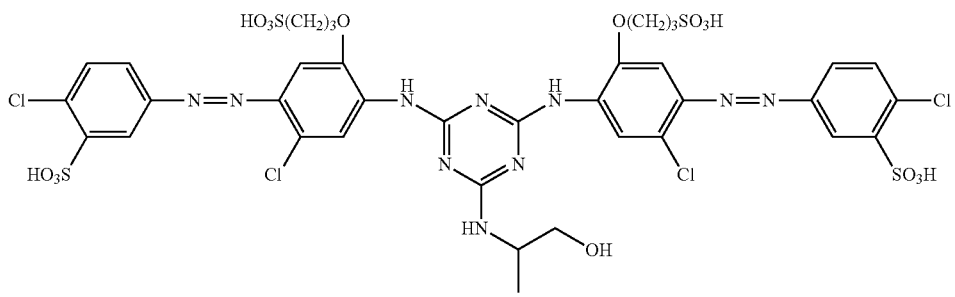
(1-14)

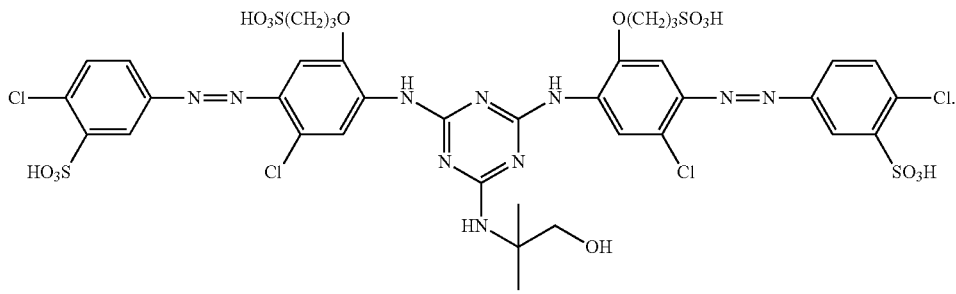
(1-15)

6) The compound or a salt thereof according to any one of 1) to 4), in which in the formula (A1-2), n is 2.

7) The compound or a salt thereof according to 1), in which the compound represented by the formula (1) is represented by the following formula (1-16).

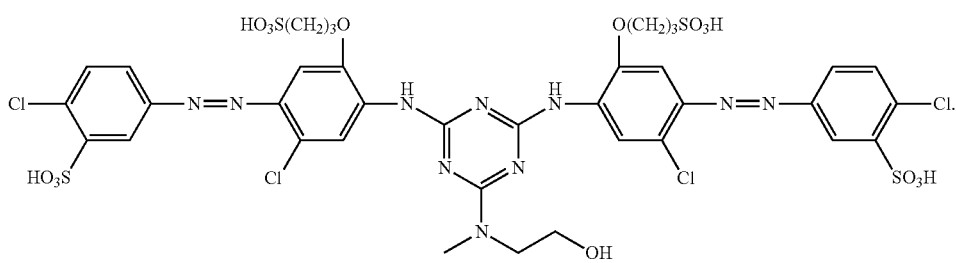
(1-16)

8) The compound or a salt thereof according to 2), in which in the the formula (1-1), Q is a chlorine atom, x is 3, and $A^1$ is a group represented by the following formula (A1-5):

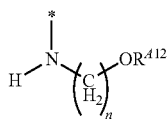
(A1-5)

in which, $R^{412}$ represents a C1-C3 alkyl group, n represents an integer of 1 to 6, and the symbol "*" indicates a position of attachment to the triazine ring.

9) The compound or a salt thereof according to 8), in which in the formula (A1-5), n is 3.

10) The compound or a salt thereof according to 2), in which in the formula (1-1), Q is a chlorine atom, x is 3, and $A^1$ is a C1-C4 alkyl-monosubstituted amino group.

11) The compound or a salt thereof according to 10), wherein in the the formula (1-1), Q is a chlorine atom, x is 3, and $A^1$ is a linear C1-C4 alkyl-monosubstituted amino group.

12) The compound or a salt thereof according to 2), wherein in the formula (1-1), Q is a chlorine atom, x is 3, and $A^1$ is a group represented by the following formula (A1-6):

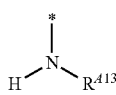
(A1-6)

in which, $R^{413}$ represents a C2-C6 alkyl group having two or more hydroxy groups, and the symbol "*" indicates a position of attachment to the triazine ring.

13) The compound or a salt thereof according to 12), in which in the formula (A1-6), $R^{413}$ is a C2-C4 alkyl group having two hydroxy groups.

14) The compound or a salt thereof according to any one of 1) to 4), in which in the formula (1), $A^1$ is a group represented by following formula (A1-7) or (A1-8):

(A1-7)

(A1-8)

in which, the symbol "*" indicates a position of attachment to the triazine ring.

15) The compound or a salt thereof according to any one of 1) to 4), in which in the formula (A1-3), m is 2.

16) The compound or a salt thereof according to 1), in which the compound represented by the formula (1) is represented by the following formula (1-17) or (1-18):

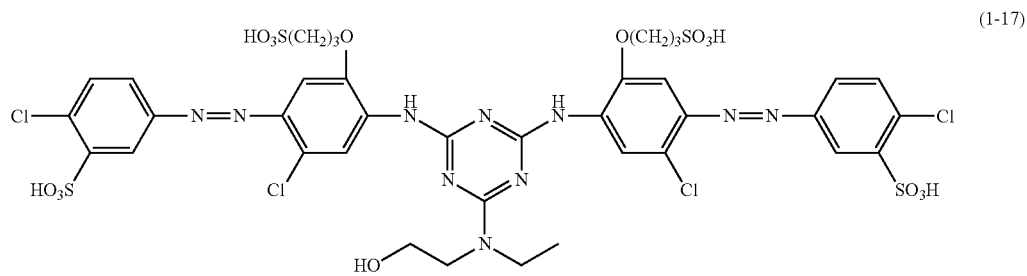
(1-17)

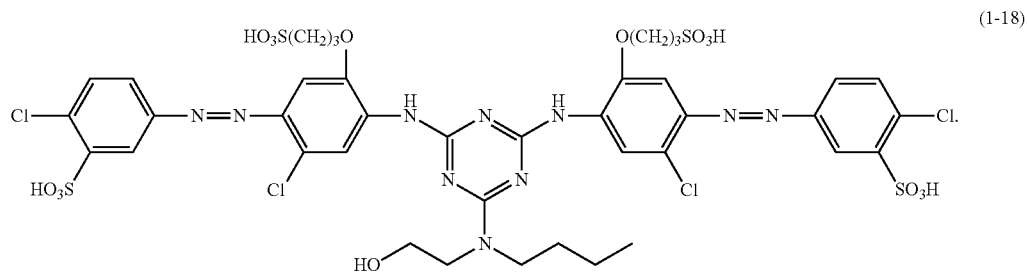
(1-18)

17) The compound or a salt thereof according to 2), in which in the formula (1-1), Q is a chlorine atom, x is 3, and $A^1$ is a group represented by the formula (1-4) wherein n is 3.

18) The compound or a salt thereof according to 2), in which in the formula (1-1), Q is a chlorine atom, x is 3, and $A^1$ is a group represented by the following formula (A1-9):

(A1-9)

in which, each $R^{A14}$ to $R^{A21}$ independently represents a hydrogen atom or a substituent, and the symbol "*" indicates a position of attachment to the triazine ring.

19) The compound or a salt thereof according to 18), in which in the formula (A1-9), $R^{A14}$ to $R^{A21}$ are hydrogen atoms.

20) The compound or a salt thereof according to 1), in which the compound represented by the formula (2) is represented by the following formula (2-1):

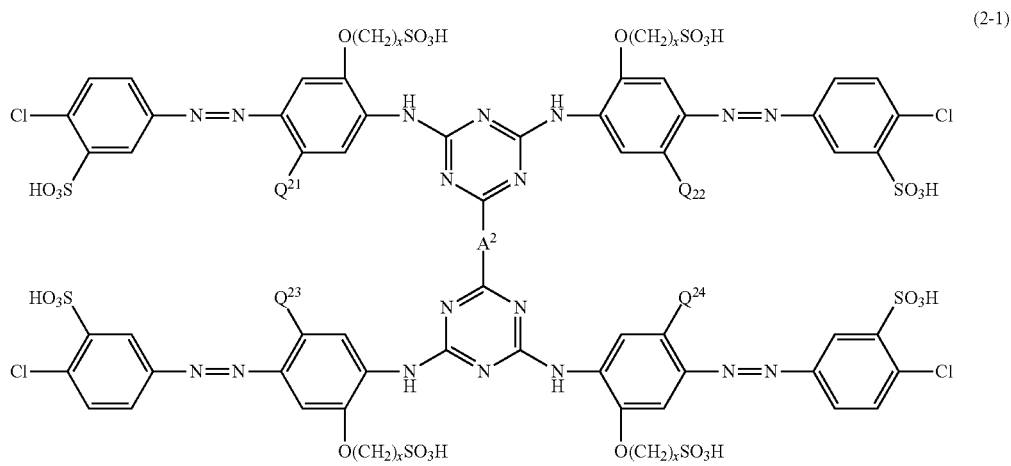

(2-1)

in which, $Q^{21}$ to $Q^{24}$ and $A^2$ have the same meanings as defined in the formula (2), each x independently represents an integer of 2 to 4.

21) The compound or a salt thereof according to 20), in which in the formula (2-1), $Q^{21}$ to $Q^{24}$ are chlorine atoms.

22) The compound or a salt thereof according to 20) or 21), in which in the formula (2-1), x is 3.

23) The compound or a salt thereof according to 20), in which in the formula (2-1), $Q^{21}$ to $Q^{24}$ are chlorine atoms, x is 3, and $A^2$ is a 1,4-piperazinediyl group.

24) An ink including the compound or a salt thereof according to any one of 1) to 23).

25) The ink according to 24), further including a water-soluble organic solvent.

26) Use of the ink according to 24) or 25) for ink-jet recording.

27) An ink-jet recording method, including discharging a droplet of the ink according to 24) or 25) in response to a recording signal to allow for attachment to a recording medium.

28) An ink-jet recording method according to 27), in which the recording medium is plain paper or a sheet having an ink receiving layer.

29) A recording medium to which either (a) the compound or a salt thereof according to any one of 1) to 23) or (b) the ink according to 24) or 25) is attached.

30) An ink-jet printer loaded with a container containing the ink according to 24) or 25).

Effects of the Invention

The present invention can provide a water-soluble azo compound capable of producing a recorded image with excellent light resistance, and a yellow ink containing the above compound for use in various types of recording, in particular for an ink-jet recording purpose.

PREFERRED MODE FOR CARRYING OUT THE INVENTION

The water-soluble azo compound according to the present invention (the compound or a salt thereof represented by the above formula (1) or (2)) is a water-soluble yellow coloring matter. Unless otherwise specifically stated, among ionic hydrophilic groups, acidic functional groups are shown in a form of a free acid. This also applies to Examples. Further, unless otherwise specifically stated, the term "compound" having an ionic hydrophilic group as used herein is meant to encompass both a "compound or a salt thereof". Moreover, unless otherwise specifically stated, the terms "%" and "part" as used herein are based on mass. This also applies to Examples.

[Compound Represented by Formula (1)]

In the above formula (1), Q represents a halogen atom. Halogen atoms include a fluorine atom, a chlorine atom, a bromine atom, and an iodine atom. Among these, a fluorine atom or a chlorine atom is preferred, and a chlorine atom is more preferred.

In the above formula (1), each $R^{11}$ and $R^{12}$ independently represents an alkyl group substituted with an ionic hydrophilic group. The carbon number of an alkyl group moiety is preferably 2 to 4, and more preferably 3. Ionic hydrophilic groups include a group selected from a sulfo group, a carboxy group, a phospho group, and a quaternary ammonium group. Among these, preferred is a group selected from a sulfo group, a carboxy group, and a phospho group. More preferred is a group selected from a sulfo group and a carboxy group. Even more preferred is a sulfo group. There is no particular limitation for the number of substitutions in an ionic hydrophilic group, but it is usually 1 to 5, preferably 1 to 4, more preferably 1 to 3, even more preferably 1 or 2, and in particular preferably 1.

Specific examples of an alkyl group substituted with an ionic hydrophilic group include, for example, a sulfomethyl group, a sulfoethyl group, a 2,3-disulfopropyl group, a 3-sulfopropyl group, a 4-sulfobutyl group, a 5-sulfopentyl group, a 6-sulfohexyl group, a 7-sulfoheptyl group, an 8-sulfooctyl group, a carboxymethyl group, a carboxyethyl group, a 3-carboxypropyl group, a 4-carboxybutyl group, a 5-carboxypentyl group, a 6-carboxyhexyl group, a 7-carboxyheptyl group, an 8-carboxyoctyl group, a phosphomethyl group, a phosphoethyl group, a 3-phosphopropyl group, a 4-phosphobutyl group, a 5-phosphopentyl group, a 6-phosphohexyl group, a 7-phosphoheptyl group, an 8-phosphooctyl group, a trimethylammoniummethyl group, a trimethylammoniumethyl group, 3-trimethylammoniumpropyl group, a 4-trimethylammoniumbutyl group, a 5-trimethylammoniumpentyl group, a 6-trimethylammoniumhexyl group, a 7-trimethylammoniumheptyl group, an 8-trimethylammoniumoctyl group, a 2-methyl-3-sulfopropyl group, a 2,2-dimethyl-3-sulfopropyl group, a 4-sulfocyclohexyl group, a 2,5-disulfocyclohexylmethyl group and the like. A 3-sulfopropyl group is preferred.

In the above formula (1), $A^1$ represents a group represented by the above formula (A1-1), a group represented by the above formula (A1-2), a C1-C3 alkoxy-substituted alkylamino group, a C1-C6 alkyl-monosubstituted amino group, a C2-C6 alkyl-monosubstituted amino group having two or more hydroxy groups, a group represented by the above formula (A1-3), a group represented by the above formula (A1-4), or a cyclic amine group. $A^1$ will be described in detail below.

Among the compounds represented by the above formula (1), preferred is a compound represented by the above formula (1-1). In the above formula (1-1), Q and $A^1$ have the same meanings as defined in the above formula (1), including those preferred and the like. In the above formula (1-1), each x independently represents an integer of 2 to 4, and preferably 3.

(Group Represented by Formula (A1-1))

In the above formula (A1-1), $R^{411}$ represents a branched alkylene group. The carbon number of $R^{411}$ is usually 2 to 20, preferably 3 to 12, more preferably 3 to 8, and even more preferably 3 to 6. Specific examples of a group represented by the above formula (A1-1) include, for example, an isopropylene group, an isobutylene group, an s-butylene group, a t-butylene group, a 1-methyl-n-butylene group, a 2-methyl-n-butylene group, a 3-methyl-n-butylene group, a 1,1-dimethyl-n-propylene group, a 1,2-dimethyl-n-propylene group, a 2,2-dimethyl-n-propylene group, a 1-ethyl-n-propylene group, an n-hexylene group, a 1-methyl-n-pentylene group, a 2-methyl-n-pentylene group, a 3-methyl-n-pentylene group, a 4-methyl-n-pentylene group, a 1,1-dimethyl-n-butylene group, a 1,2-dimethyl-n-butylene group, a 1,3-dimethyl-n-butylene group, a 2,2-dimethyl-n-butylene group, a 2,3-dimethyl-n-butylene group, a 3,3-dimethyl-n-butylene group, a 1-ethyl-n-butylene group, a 2-ethyl-n-butylene group, a 1,1,2-trimethyl-n-propylene group, a 1,2,2-trimethyl-n-propylene group, a 1-ethyl-1-methyl-n-propylene group, a 1-ethyl-2-methyl-n-propylene group and the like. An isobutylene group or a 3-methyl-n-butylene group is preferred.

When $A^1$ in the above formula (1) is a group represented by the above formula (A1-1), preferred compounds include, for example, those represented by the above formulae (1-11) to (1-15).

(Group Represented by Formula (A1-2))

In the above formula (A1-2), n represents an integer of 1 to 6, preferably an integer of 2 to 5, and more preferably 2.

Specific examples of a compound in which $A^1$ in the above formula (1) is a group represented by the above formula (A1-2) are shown in the Tables 1 and 2 below. However, the present invention shall not be limited to these specific examples. Abbreviations in Tables 1 and 2 have the following meanings.

2-SEt: 2-sulfoethyl (*—$CH_2CH_2$—$SO_3H$)
3-S″Pr: 3-sulfo-n-propyl (*—$CH_2CH_2CH_2$—$SO_3H$)
4-S″Bu: 3-sulfo-n-butyl (*—$CH_2CH_2CH_2CH_2$—$SO_3H$)

The symbol "*" in the above formulae indicates a position of attachment to the oxygen atom.

TABLE 1

| No. | Q | $R^{11}$ | $R^{12}$ | $A^1$ |
|---|---|---|---|---|
| 1 | Cl | 2-SEt | 2-SEt | Formula (A1-2), n = 1 |
| 2 | Cl | 3-S″Pr | 3-S″Pr | Formula (A1-2), n = 1 |
| 3 | Cl | 4-S″Bu | 4-S″Bu | Formula (A1-2), n = 1 |
| 4 | Cl | 2-SEt | 2-SEt | Formula (A1-2), n = 2 |
| 5 | Cl | 3-S″Pr | 3-S″Pr | Formula (A1-2), n = 2 |
| 6 | Cl | 4-S″Bu | 4-S″Bu | Formula (A1-2), n = 2 |
| 7 | Cl | 2-SEt | 2-SEt | Formula (A1-2), n = 3 |
| 8 | Cl | 3-S″Pr | 3-S″Pr | Formula (A1-2), n = 3 |
| 9 | Cl | 4-S″Bu | 4-S″Bu | Formula (A1-2), n = 3 |
| 10 | Cl | 2-SEt | 2-SEt | Formula (A1-2), n = 4 |
| 11 | Cl | 3-S″Pr | 3-S″Pr | Formula (A1-2), n = 4 |
| 12 | Cl | 4-S″Bu | 4-S″Bu | Formula (A1-2), n = 4 |
| 13 | Cl | 2-SEt | 2-SEt | Formula (A1-2), n = 5 |
| 14 | Cl | 3-S″Pr | 3-S″Pr | Formula (A1-2), n = 5 |
| 15 | Cl | 4-S″Bu | 4-S″Bu | Formula (A1-2), n = 5 |
| 16 | Cl | 2-SEt | 2-SEt | Formula (A1-2), n = 6 |
| 17 | Cl | 3-S″Pr | 3-S″Pr | Formula (A1-2), n = 6 |
| 18 | Cl | 4-S″Bu | 4-S″Bu | Formula (A1-2), n = 6 |
| 19 | Br | 2-SEt | 2-SEt | Formula (A1-2), n = 1 |

TABLE 1-continued

| No. | Q | $R^{11}$ | $R^{12}$ | $A^1$ |
|---|---|---|---|---|
| 20 | Br | 3-S"Pr | 3-S"Pr | Formula (A1-2), n = 1 |
| 21 | Br | 4-S"Bu | 4-S"Bu | Formula (A1-2), n = 1 |
| 22 | Br | 2-SEt | 2-SEt | Formula (A1-2), n = 2 |
| 23 | Br | 3-S"Pr | 3-S"Pr | Formula (A1-2), n = 2 |
| 24 | Br | 4-S"Bu | 4-S"Bu | Formula (A1-2), n = 2 |
| 25 | Br | 2-SEt | 2-SEt | Formula (A1-2), n = 3 |
| 26 | Br | 3-S"Pr | 3-S"Pr | Formula (A1-2), n = 3 |
| 27 | Br | 4-S"Bu | 4-S"Bu | Formula (A1-2), n = 3 |
| 28 | Br | 2-SEt | 2-SEt | Formula (A1-2), n = 4 |
| 29 | Br | 3-S"Pr | 3-S"Pr | Formula (A1-2), n = 4 |
| 30 | Br | 4-S"Bu | 4-S"Bu | Formula (A1-2), n = 4 |

TABLE 2

| No. | Q | $R^{11}$ | $R^{12}$ | $A^1$ |
|---|---|---|---|---|
| 31 | Br | 2-SEt | 2-SEt | Formula (A1-2), n = 5 |
| 32 | Br | 3-S"Pr | 3-S"Pr | Formula (A1-2), n = 5 |
| 33 | Br | 4-S"Bu | 4-S"Bu | Formula (A1-2), n = 5 |
| 34 | Br | 2-SEt | 2-SEt | Formula (A1-2), n = 6 |
| 35 | Br | 3-S"Pr | 3-S"Pr | Formula (A1-2), n = 6 |
| 36 | Br | 4-S"Bu | 4-S"Bu | Formula (A1-2), n = 6 |
| 37 | F | 2-SEt | 2-SEt | Formula (A1-2), n = 1 |
| 38 | F | 3-S"Pr | 3-S"Pr | Formula (A1-2), n = 1 |
| 39 | F | 4-S"Bu | 4-S"Bu | Formula (A1-2), n = 1 |
| 40 | F | 2-SEt | 2-SEt | Formula (A1-2), n = 2 |
| 41 | F | 3-S"Pr | 3-S"Pr | Formula (A1-2), n = 2 |
| 42 | F | 4-S"Bu | 4-S"Bu | Formula (A1-2), n = 2 |
| 43 | F | 2-SEt | 2-SEt | Formula (A1-2), n = 3 |
| 44 | F | 3-S"Pr | 3-S"Pr | Formula (A1-2), n = 3 |
| 45 | F | 4-S"Bu | 4-S"Bu | Formula (A1-2), n = 3 |
| 46 | F | 2-SEt | 2-SEt | Formula (A1-2), n = 4 |
| 47 | F | 3-S"Pr | 3-S"Pr | Formula (A1-2), n = 4 |
| 48 | F | 4-S"Bu | 4-S"Bu | Formula (A1-2), n = 4 |
| 49 | F | 2-SEt | 2-SEt | Formula (A1-2), n = 5 |
| 50 | F | 3-S"Pr | 3-S"Pr | Formula (A1-2), n = 5 |
| 51 | F | 4-S"Bu | 4-S"Bu | Formula (A1-2), n = 5 |
| 52 | F | 2-SEt | 2-SEt | Formula (A1-2), n = 6 |
| 53 | F | 3-S"Pr | 3-S"Pr | Formula (A1-2), n = 6 |
| 54 | F | 4-S"Bu | 4-S"Bu | Formula (A1-2), n = 6 |

When $A^1$ in the above formula (1) is a group represented by the above formula (A1-2), preferred compounds include, for example, one represented by the above formula (1-16).

(C1-C3 Alkoxy-Substituted Alkylamino Group)

The carbon number of an alkyl moiety in a C1-C3 alkoxy-substituted alkylamino group is preferably 1 to 6, more preferably 2 to 5, and even more preferably 3. The number of substitutions in a C1-C3 alkoxy group of a C1-C3 alkoxy-substituted alkylamino group is usually 1 or 2, preferably 1.

Among C1-C3 alkoxy-substituted alkylamino groups, preferred is a group represented by the above formula (A1-5). In the above formula (A1-5), $R^{412}$ represents a C1-C3 alkyl group. Further, in the above formula (A1-5), n represents an integer of 1 to 6, preferably an integer of 2 to 5, and more preferably 3.

Specific examples of a compound in which $A^1$ in the above formula (1) is a C1-C3 alkoxy-substituted alkylamino group are shown in the Tables 3 to 14 below. However, the present invention shall not be limited to these specific examples. Abbreviations in Tables 3 to 14 have the following meanings.

SMe: sulfomethyl (*—$CH_2$—$SO_3H$)
2-SEt: 2-sulfoethyl (*—$CH_2CH_2$—$SO_3H$)
3-S"Pr: 3-sulfo-n-propyl (*—$CH_2CH_2CH_2$—$SO_3H$)
4-S"Bu: 3-sulfo-n-butyl (*—$CH_2CH_2CH_2CH_2$—$SO_3H$)

The symbol "*" in the above formulae indicates a position of attachment to the oxygen atom.

TABLE 3

| No. | Q | $R^{11}$ | $R^{12}$ | $A^1$ |
|---|---|---|---|---|
| 1 | Cl | SMe | SMe | Formula (A1-5), n = 1, $R^{412} = CH_3$ |
| 2 | Cl | SMe | 2-SEt | Formula (A1-5), n = 1, $R^{412} = CH_3$ |
| 3 | Cl | SMe | 3-S"Pr | Formula (A1-5), n = 1, $R^{412} = CH_3$ |
| 4 | Cl | SMe | 4-S"Bu | Formula (A1-5), n = 1, $R^{412} = CH_3$ |
| 5 | Cl | 2-SEt | 2-SEt | Formula (A1-5), n = 1, $R^{412} = CH_3$ |
| 6 | Cl | 2-SEt | 3-S"Pr | Formula (A1-5), n = 1, $R^{412} = CH_3$ |
| 7 | Cl | 2-SEt | 4-S"Bu | Formula (A1-5), n = 1, $R^{412} = CH_3$ |
| 8 | Cl | 3-S"Pr | 3-S"Pr | Formula (A1-5), n = 1, $R^{412} = CH_3$ |
| 9 | Cl | 3-S"Pr | 4-S"Bu | Formula (A1-5), n = 1, $R^{412} = CH_3$ |
| 10 | Cl | 4-S"Bu | 4-S"Bu | Formula (A1-5), n = 1, $R^{412} = CH_3$ |
| 11 | Cl | SMe | SMe | Formula (A1-5), n = 2, $R^{412} = CH_3$ |
| 12 | Cl | SMe | 2-SEt | Formula (A1-5), n = 2, $R^{412} = CH_3$ |
| 13 | Cl | SMe | 3-S"Pr | Formula (A1-5), n = 2, $R^{412} = CH_3$ |
| 14 | Cl | SMe | 4-S"Bu | Formula (A1-5), n = 2, $R^{412} = CH_3$ |
| 15 | Cl | 2-SEt | 2-SEt | Formula (A1-5), n = 2, $R^{412} = CH_3$ |
| 16 | Cl | 2-SEt | 3-S"Pr | Formula (A1-5), n = 2, $R^{412} = CH_3$ |
| 17 | Cl | 2-SEt | 4-S"Bu | Formula (A1-5), n = 2, $R^{412} = CH_3$ |
| 18 | Cl | 3-SnPr | 3-S"Pr | Formula (A1-5), n = 2, $R^{412} = CH_3$ |
| 19 | Cl | 3-S"Pr | 4-S"Bu | Formula (A1-5), n = 2, $R^{412} = CH_3$ |
| 20 | Cl | 4-S"Bu | 4-S"Bu | Formula (A1-5), n = 2, $R^{412} = CH_3$ |
| 21 | Cl | SMe | SMe | Formula (A1-5), n = 3, $R^{412} = CH_3$ |
| 22 | Cl | SMe | 2-SEt | Formula (A1-5), n = 3, $R^{412} = CH_3$ |
| 23 | Cl | SMe | 3-S"Pr | Formula (A1-5), n = 3, $R^{412} = CH_3$ |
| 24 | Cl | SMe | 4-S"Bu | Formula (A1-5), n = 3, $R^{412} = CH_3$ |
| 25 | Cl | 2-SEt | 2-SEt | Formula (A1-5), n = 3, $R^{412} = CH_3$ |
| 26 | Cl | 2-SEt | 3-S"Pr | Formula (A1-5), n = 3, $R^{412} = CH_3$ |
| 27 | Cl | 2-SEt | 4-S"Bu | Formula (A1-5), n = 3, $R^{412} = CH_3$ |
| 28 | Cl | 3-S"Pr | 3-S"Pr | Formula (A1-5), n = 3, $R^{412} = CH_3$ |
| 29 | Cl | 3-S"Pr | 4-S"Bu | Formula (A1-5), n = 3, $R^{412} = CH_3$ |
| 30 | Cl | 4-S"Bu | 4-S"Bu | Formula (A1-5), n = 3, $R^{412} = CH_3$ |

TABLE 4

| No. | Q | $R^{11}$ | $R^{12}$ | $A^1$ |
|---|---|---|---|---|
| 31 | Cl | SMe | SMe | Formula (A1-5), n = 4, $R^{412} = CH_3$ |
| 32 | Cl | SMe | 2-SEt | Formula (A1-5), n = 4, $R^{412} = CH_3$ |
| 33 | Cl | SMe | 3-S"Pr | Formula (A1-5), n = 4, $R^{412} = CH_3$ |
| 34 | Cl | SMe | 4-S"Bu | Formula (A1-5), n = 4, $R^{412} = CH_3$ |
| 35 | Cl | 2-SEt | 2-SEt | Formula (A1-5), n = 4, $R^{412} = CH_3$ |
| 36 | Cl | 2-SEt | 3-S"Pr | Formula (A1-5), n = 4, $R^{412} = CH_3$ |
| 37 | Cl | 2-SEt | 4-S"Bu | Formula (A1-5), n = 4, $R^{412} = CH_3$ |
| 38 | Cl | 3-S"Pr | 3-S"Pr | Formula (A1-5), n = 4, $R^{412} = CH_3$ |
| 39 | Cl | 3-S"Pr | 4-S"Bu | Formula (A1-5), n = 4, $R^{412} = CH_3$ |
| 40 | Cl | 4-S"Bu | 4-S"Bu | Formula (A1-5), n = 4, $R^{412} = CH_3$ |
| 41 | Cl | SMe | SMe | Formula (A1-5), n = 5, $R^{412} = CH_3$ |
| 42 | Cl | SMe | 2-SEt | Formula (A1-5), n = 5, $R^{412} = CH_3$ |
| 43 | Cl | SMe | 3-S"Pr | Formula (A1-5), n = 5, $R^{412} = CH_3$ |
| 44 | Cl | SMe | 4-S"Bu | Formula (A1-5), n = 5, $R^{412} = CH_3$ |
| 45 | Cl | 2-SEt | 2-SEt | Formula (A1-5), n = 5, $R^{412} = CH_3$ |
| 46 | Cl | 2-SEt | 3-S"Pr | Formula (A1-5), n = 5, $R^{412} = CH_3$ |
| 47 | Cl | 2-SEt | 4-S"Bu | Formula (A1-5), n = 5, $R^{412} = CH_3$ |
| 48 | Cl | 3-S"Pr | 3-S"Pr | Formula (A1-5), n = 5, $R^{412} = CH_3$ |
| 49 | Cl | 3-S"Pr | 4-S"Bu | Formula (A1-5), n = 5, $R^{412} = CH_3$ |
| 50 | Cl | 4-S"Bu | 4-S"Bu | Formula (A1-5), n = 5, $R^{412} = CH_3$ |
| 51 | Cl | SMe | SMe | Formula (A1-5), n = 6, $R^{412} = CH_3$ |
| 52 | Cl | SMe | 2-SEt | Formula (A1-5), n = 6, $R^{412} = CH_3$ |
| 53 | Cl | SMe | 3-S"Pr | Formula (A1-5), n = 6, $R^{412} = CH_3$ |
| 54 | Cl | SMe | 4-S"Bu | Formula (A1-5), n = 6, $R^{412} = CH_3$ |
| 55 | Cl | 2-SEt | 2-SEt | Formula (A1-5), n = 6, $R^{412} = CH_3$ |
| 56 | Cl | 2-SEt | 3-S"Pr | Formula (A1-5), n = 6, $R^{412} = CH_3$ |
| 57 | Cl | 2-SEt | 4-S"Bu | Formula (A1-5), n = 6, $R^{412} = CH_3$ |
| 58 | Cl | 3-S"Pr | 3-S"Pr | Formula (A1-5), n = 6, $R^{412} = CH_3$ |
| 59 | Cl | 3-S"Pr | 4-S"Bu | Formula (A1-5), n = 6, $R^{412} = CH_3$ |
| 60 | Cl | 4-S"Bu | 4-S"Bu | Formula (A1-5), n = 6, $R^{412} = CH_3$ |

TABLE 5

| No. | Q | $R^{11}$ | $R^{12}$ | $A^1$ |
|---|---|---|---|---|
| 61 | Cl | SMe | SMe | Formula (A1-5), n = 1, $R^{412} = CH_2CH_3$ |
| 62 | Cl | SMe | 2-SEt | Formula (A1-5), n = 1, $R^{412} = CH_2CH_3$ |
| 63 | Cl | SMe | 3-S"Pr | Formula (A1-5), n = 1, $R^{412} = CH_2CH_3$ |

TABLE 5-continued

| No. | Q | R$^{11}$ | R$^{12}$ | A$^1$ |
|---|---|---|---|---|
| 64 | Cl | SMe | 4-S"Bu | Formula (A1-5), n = 1, R$^{412}$ = CH$_2$CH$_3$ |
| 65 | Cl | 2-SEt | 2-SEt | Formula (A1-5), n = 1, R$^{412}$ = CH$_2$CH$_3$ |
| 66 | Cl | 2-SEt | 3-S"Pr | Formula (A1-5), n = 1, R$^{412}$ = CH$_2$CH$_3$ |
| 67 | Cl | 2-SEt | 4-S"Bu | Formula (A1-5), n = 1, R$^{412}$ = CH$_2$CH$_3$ |
| 68 | Cl | 3-S"Pr | 3-S"Pr | Formula (A1-5), n = 1, R$^{412}$ = CH$_2$CH$_3$ |
| 69 | Cl | 3-S"Pr | 4-S"Bu | Formula (A1-5), n = 1, R$^{412}$ = CH$_2$CH$_3$ |
| 70 | Cl | 4-S"Bu | 4-S"Bu | Formula (A1-5), n = 1, R$^{412}$ = CH$_2$CH$_3$ |
| 71 | Cl | SMe | SMe | Formula (A1-5), n = 2, R$^{412}$ = CH$_2$CH$_3$ |
| 72 | Cl | SMe | 2-SEt | Formula (A1-5), n = 2, R$^{412}$ = CH$_2$CH$_3$ |
| 73 | Cl | SMe | 3-S"Pr | Formula (A1-5), n = 2, R$^{412}$ = CH$_2$CH$_3$ |
| 74 | Cl | SMe | 4-S"Bu | Formula (A1-5), n = 2, R$^{412}$ = CH$_2$CH$_3$ |
| 75 | Cl | 2-SEt | 2-SEt | Formula (A1-5), n = 2, R$^{412}$ = CH$_2$CH$_3$ |
| 76 | Cl | 2-SEt | 3-S"Pr | Formula (A1-5), n = 2, R$^{412}$ = CH$_2$CH$_3$ |
| 77 | Cl | 2-SEt | 4-S"Bu | Formula (A1-5), n = 2, R$^{412}$ = CH$_2$CH$_3$ |
| 78 | Cl | 3-S"Pr | 3-S"Pr | Formula (A1-5), n = 2, R$^{412}$ = CH$_2$CH$_3$ |
| 79 | Cl | 3-S"Pr | 4-S"Bu | Formula (A1-5), n = 2, R$^{412}$ = CH$_2$CH$_3$ |
| 80 | Cl | 4-S"Bu | 4-S"Bu | Formula (A1-5), n = 2, R$^{412}$ = CH$_2$CH$_3$ |
| 81 | Cl | SMe | SMe | Formula (A1-5), n = 3, R$^{412}$ = CH$_2$CH$_3$ |
| 82 | Cl | SMe | 2-SEt | Formula (A1-5), n = 3, R$^{412}$ = CH$_2$CH$_3$ |
| 83 | Cl | SMe | 3-S"Pr | Formula (A1-5), n = 3, R$^{412}$ = CH$_2$CH$_3$ |
| 84 | Cl | SMe | 4-S"Bu | Formula (A1-5), n = 3, R$^{412}$ = CH$_2$CH$_3$ |
| 85 | Cl | 2-SEt | 2-SEt | Formula (A1-5), n = 3, R$^{412}$ = CH$_2$CH$_3$ |
| 86 | Cl | 2-SEt | 3-S"Pr | Formula (A1-5), n = 3, R$^{412}$ = CH$_2$CH$_3$ |
| 87 | Cl | 2-SEt | 4-S"Bu | Formula (A1-5), n = 3, R$^{412}$ = CH$_2$CH$_3$ |
| 88 | Cl | 3-S"Pr | 3-S"Pr | Formula (A1-5), n = 3, R$^{412}$ = CH$_2$CH$_3$ |
| 89 | Cl | 3-S"Pr | 4-S"Bu | Formula (A1-5), n = 3, R$^{412}$ = CH$_2$CH$_3$ |
| 90 | Cl | 4-S"Bu | 4-S"Bu | Formula (A1-5), n = 3, R$^{412}$ = CH$_2$CH$_3$ |

TABLE 6

| No. | Q | R$^{11}$ | R$^{12}$ | A$^1$ |
|---|---|---|---|---|
| 91 | Cl | SMe | SMe | Formula (A1-5), n = 4, R$^{412}$ = CH$_2$CH$_3$ |
| 92 | Cl | SMe | 2-SEt | Formula (A1-5), n = 4, R$^{412}$ = CH$_2$CH$_3$ |
| 93 | Cl | SMe | 3-S"Pr | Formula (A1-5), n = 4, R$^{412}$ = CH$_2$CH$_3$ |
| 94 | Cl | SMe | 4-S"Bu | Formula (A1-5), n = 4, R$^{412}$ = CH$_2$CH$_3$ |
| 95 | Cl | 2-SEt | 2-SEt | Formula (A1-5), n = 4, R$^{412}$ = CH$_2$CH$_3$ |
| 96 | Cl | 2-SEt | 3-S"Pr | Formula (A1-5), n = 4, R$^{412}$ = CH$_2$CH$_3$ |
| 97 | Cl | 2-SEt | 4-S"Bu | Formula (A1-5), n = 4, R$^{412}$ = CH$_2$CH$_3$ |
| 98 | Cl | 3-S"Pr | 3-S"Pr | Formula (A1-5), n = 4, R$^{412}$ = CH$_2$CH$_3$ |
| 99 | Cl | 3-S"Pr | 4-S"Bu | Formula (A1-5), n = 4, R$^{412}$ = CH$_2$CH$_3$ |
| 100 | Cl | 4-S"Bu | 4-S"Bu | Formula (A1-5), n = 4, R$^{412}$ = CH$_2$CH$_3$ |
| 101 | Cl | SMe | SMe | Formula (A1-5), n = 5, R$^{412}$ = CH$_2$CH$_3$ |
| 102 | Cl | SMe | 2-SEt | Formula (A1-5), n = 5, R$^{412}$ = CH$_2$CH$_3$ |
| 103 | Cl | SMe | 3-S"Pr | Formula (A1-5), n = 5, R$^{412}$ = CH$_2$CH$_3$ |
| 104 | Cl | SMe | 4-S"Bu | Formula (A1-5), n = 5, R$^{412}$ = CH$_2$CH$_3$ |
| 105 | Cl | 2-SEt | 2-SEt | Formula (A1-5), n = 5, R$^{412}$ = CH$_2$CH$_3$ |
| 106 | Cl | 2-SEt | 3-S"Pr | Formula (A1-5), n = 5, R$^{412}$ = CH$_2$CH$_3$ |
| 107 | Cl | 2-SEt | 4-S"Bu | Formula (A1-5), n = 5, R$^{412}$ = CH$_2$CH$_3$ |
| 108 | Cl | 3-S"Pr | 3-S"Pr | Formula (A1-5), n = 5, R$^{412}$ = CH$_2$CH$_3$ |
| 109 | Cl | 3-S"Pr | 4-S"Bu | Formula (A1-5), n = 5, R$^{412}$ = CH$_2$CH$_3$ |
| 110 | Cl | 4-S"Bu | 4-S"Bu | Formula (A1-5), n = 5, R$^{412}$ = CH$_2$CH$_3$ |
| 111 | Cl | SMe | SMe | Formula (A1-5), n = 6, R$^{412}$ = CH$_2$CH$_3$ |
| 112 | Cl | SMe | 2-SEt | Formula (A1-5), n = 6, R$^{412}$ = CH$_2$CH$_3$ |
| 113 | Cl | SMe | 3-S"Pr | Formula (A1-5), n = 6, R$^{412}$ = CH$_2$CH$_3$ |
| 114 | Cl | SMe | 4-S"Bu | Formula (A1-5), n = 6, R$^{412}$ = CH$_2$CH$_3$ |
| 115 | Cl | 2-SEt | 2-SEt | Formula (A1-5), n = 6, R$^{412}$ = CH$_2$CH$_3$ |
| 116 | Cl | 2-SEt | 3-S"Pr | Formula (A1-5), n = 6, R$^{412}$ = CH$_2$CH$_3$ |
| 117 | Cl | 2-SEt | 4-S"Bu | Formula (A1-5), n = 6, R$^{412}$ = CH$_2$CH$_3$ |
| 118 | Cl | 3-S"Pr | 3-S"Pr | Formula (A1-5), n = 6, R$^{412}$ = CH$_2$CH$_3$ |
| 119 | Cl | 3-S"Pr | 4-S"Bu | Formula (A1-5), n = 6, R$^{412}$ = CH$_2$CH$_3$ |
| 120 | Cl | 4-S"Bu | 4-S"Bu | Formula (A1-5), n = 6, R$^{412}$ = CH$_2$CH$_3$ |

TABLE 7

| No. | Q | R$^{11}$ | R$^{12}$ | A$^1$ |
|---|---|---|---|---|
| 121 | Br | SMe | SMe | Formula (A1-5), n = 1, R$^{412}$ = CH$_3$ |
| 122 | Br | SMe | 2-SEt | Formula (A1-5), n = 1, R$^{412}$ = CH$_3$ |
| 123 | Br | SMe | 3-S"Pr | Formula (A1-5), n = 1, R$^{412}$ = CH$_3$ |
| 124 | Br | SMe | 4-S"Bu | Formula (A1-5), n = 1, R$^{412}$ = CH$_3$ |
| 125 | Br | 2-SEt | 2-SEt | Formula (A1-5), n = 1, R$^{412}$ = CH$_3$ |
| 126 | Br | 2-SEt | 3-S"Pr | Formula (A1-5), n = 1, R$^{412}$ = CH$_3$ |
| 127 | Br | 2-SEt | 4-S"Bu | Formula (A1-5), n = 1, R$^{412}$ = CH$_3$ |
| 128 | Br | 3-S"Pr | 3-S"Pr | Formula (A1-5), n = 1, R$^{412}$ = CH$_3$ |
| 129 | Br | 3-S"Pr | 4-S"Bu | Formula (A1-5), n = 1, R$^{412}$ = CH$_3$ |
| 130 | Br | 4-S"Bu | 4-S"Bu | Formula (A1-5), n = 1, R$^{412}$ = CH$_3$ |
| 131 | Br | SMe | SMe | Formula (A1-5), n = 2, R$^{412}$ = CH$_3$ |
| 132 | Br | SMe | 2-SEt | Formula (A1-5), n = 2, R$^{412}$ = CH$_3$ |
| 133 | Br | SMe | 3-S"Pr | Formula (A1-5), n = 2, R$^{412}$ = CH$_3$ |
| 134 | Br | SMe | 4-S"Bu | Formula (A1-5), n = 2, R$^{412}$ = CH$_3$ |
| 135 | Br | 2-SEt | 2-SEt | Formula (A1-5), n = 2, R$^{412}$ = CH$_3$ |
| 136 | Br | 2-SEt | 3-S"Pr | Formula (A1-5), n = 2, R$^{412}$ = CH$_3$ |
| 137 | Br | 2-SEt | 4-S"Bu | Formula (A1-5), n = 2, R$^{412}$ = CH$_3$ |
| 138 | Br | 3-S"Pr | 3-S"Pr | Formula (A1-5), n = 2, R$^{412}$ = CH$_3$ |
| 139 | Br | 3-S"Pr | 4-S"Bu | Formula (A1-5), n = 2, R$^{412}$ = CH$_3$ |
| 140 | Br | 4-S"Bu | 4-S"Bu | Formula (A1-5), n = 2, R$^{412}$ = CH$_3$ |
| 141 | Br | SMe | SMe | Formula (A1-5), n = 3, R$^{412}$ = CH$_3$ |
| 142 | Br | SMe | 2-SEt | Formula (A1-5), n = 3, R$^{412}$ = CH$_3$ |
| 143 | Br | SMe | 3-S"Pr | Formula (A1-5), n = 3, R$^{412}$ = CH$_3$ |
| 144 | Br | SMe | 4-S"Bu | Formula (A1-5), n = 3, R$^{412}$ = CH$_3$ |
| 145 | Br | 2-SEt | 2-SEt | Formula (A1-5), n = 3, R$^{412}$ = CH$_3$ |
| 146 | Br | 2-SEt | 3-S"Pr | Formula (A1-5), n = 3, R$^{412}$ = CH$_3$ |
| 147 | Br | 2-SEt | 4-S"Bu | Formula (A1-5), n = 3, R$^{412}$ = CH$_3$ |
| 148 | Br | 3-S"Pr | 3-S"Pr | Formula (A1-5), n = 3, R$^{412}$ = CH$_3$ |
| 149 | Br | 3-S"Pr | 4-S"Bu | Formula (A1-5), n = 3, R$^{412}$ = CH$_3$ |
| 150 | Br | 4-S"Bu | 4-S"Bu | Formula (A1-5), n = 3, R$^{412}$ = CH$_3$ |

TABLE 8

| No. | Q | R$^{11}$ | R$^{12}$ | A$^1$ |
|---|---|---|---|---|
| 151 | Br | SMe | SMe | Formula (A1-5), n = 4, R$^{412}$ = CH$_3$ |
| 152 | Br | SMe | 2-SEt | Formula (A1-5), n = 4, R$^{412}$ = CH$_3$ |
| 153 | Br | SMe | 3-S"Pr | Formula (A1-5), n = 4, R$^{412}$ = CH$_3$ |
| 154 | Br | SMe | 4-S"Bu | Formula (A1-5), n = 4, R$^{412}$ = CH$_3$ |
| 155 | Br | 2-SEt | 2-SEt | Formula (A1-5), n = 4, R$^{412}$ = CH$_3$ |
| 156 | Br | 2-SEt | 3-S"Pr | Formula (A1-5), n = 4, R$^{412}$ = CH$_3$ |
| 157 | Br | 2-SEt | 4-S"Bu | Formula (A1-5), n = 4, R$^{412}$ = CH$_3$ |
| 158 | Br | 3-S"Pr | 3-S"Pr | Formula (A1-5), n = 4, R$^{412}$ = CH$_3$ |
| 159 | Br | 3-S"Pr | 4-S"Bu | Formula (A1-5), n = 4, R$^{412}$ = CH$_3$ |
| 160 | Br | 4-S"Bu | 4-S"Bu | Formula (A1-5), n = 4, R$^{412}$ = CH$_3$ |
| 161 | Br | SMe | SMe | Formula (A1-5), n = 5, R$^{412}$ = CH$_3$ |
| 162 | Br | SMe | 2-SEt | Formula (A1-5), n = 5, R$^{412}$ = CH$_3$ |
| 163 | Br | SMe | 3-S"Pr | Formula (A1-5), n = 5, R$^{412}$ = CH$_3$ |
| 164 | Br | SMe | 4-S"Bu | Formula (A1-5), n = 5, R$^{412}$ = CH$_3$ |
| 165 | Br | 2-SEt | 2-SEt | Formula (A1-5), n = 5, R$^{412}$ = CH$_3$ |
| 166 | Br | 2-SEt | 3-S"Pr | Formula (A1-5), n = 5, R$^{412}$ = CH$_3$ |
| 167 | Br | 2-SEt | 4-S"Bu | Formula (A1-5), n = 5, R$^{412}$ = CH$_3$ |
| 168 | Br | 3-S"Pr | 3-S"Pr | Formula (A1-5), n = 5, R$^{412}$ = CH$_3$ |
| 169 | Br | 3-S"Pr | 4-S"Bu | Formula (A1-5), n = 5, R$^{412}$ = CH$_3$ |
| 170 | Br | 4-S"Bu | 4-S"Bu | Formula (A1-5), n = 5, R$^{412}$ = CH$_3$ |
| 171 | Br | SMe | SMe | Formula (A1-5), n = 6, R$^{412}$ = CH$_3$ |
| 172 | Br | SMe | 2-SEt | Formula (A1-5), n = 6, R$^{412}$ = CH$_3$ |
| 173 | Br | SMe | 3-S"Pr | Formula (A1-5), n = 6, R$^{412}$ = CH$_3$ |
| 174 | Br | SMe | 4-S"Bu | Formula (A1-5), n = 6, R$^{412}$ = CH$_3$ |
| 175 | Br | 2-SEt | 2-SEt | Formula (A1-5), n = 6, R$^{412}$ = CH$_3$ |
| 176 | Br | 2-SEt | 3-S"Pr | Formula (A1-5), n = 6, R$^{412}$ = CH$_3$ |
| 177 | Br | 2-SEt | 4-S"Bu | Formula (A1-5), n = 6, R$^{412}$ = CH$_3$ |
| 178 | Br | 3-S"Pr | 3-S"Pr | Formula (A1-5), n = 6, R$^{412}$ = CH$_3$ |
| 179 | Br | 3-S"Pr | 4-S"Bu | Formula (A1-5), n = 6, R$^{412}$ = CH$_3$ |
| 180 | Br | 4-S"Bu | 4-S"Bu | Formula (A1-5), n = 6, R$^{412}$ = CH$_3$ |

TABLE 9

| No. | Q | R$^{11}$ | R$^{12}$ | A$^1$ |
|---|---|---|---|---|
| 181 | Br | SMe | SMe | Formula (A1-5), n = 1, R$^{412}$ = CH$_2$CH$_3$ |
| 182 | Br | SMe | 2-SEt | Formula (A1-5), n = 1, R$^{412}$ = CH$_2$CH$_3$ |
| 183 | Br | SMe | 3-S"Pr | Formula (A1-5), n = 1, R$^{412}$ = CH$_2$CH$_3$ |
| 184 | Br | SMe | 4-S"Bu | Formula (A1-5), n = 1, R$^{412}$ = CH$_2$CH$_3$ |
| 185 | Br | 2-SEt | 2-SEt | Formula (A1-5), n = 1, R$^{412}$ = CH$_2$CH$_3$ |
| 186 | Br | 2-SEt | 3-S"Pr | Formula (A1-5), n = 1, R$^{412}$ = CH$_2$CH$_3$ |
| 187 | Br | 2-SEt | 4-S"Bu | Formula (A1-5), n = 1, R$^{412}$ = CH$_2$CH$_3$ |
| 188 | Br | 3-S"Pr | 3-S"Pr | Formula (A1-5), n = 1, R$^{412}$ = CH$_2$CH$_3$ |
| 189 | Br | 3-S"Pr | 4-S"Bu | Formula (A1-5), n = 1, R$^{412}$ = CH$_2$CH$_3$ |

TABLE 9-continued

| No. | Q | R¹¹ | R¹² | A¹ |
|---|---|---|---|---|
| 190 | Br | 4-S"Bu | 4-S"Bu | Formula (A1-5), n = 1, $R^{A12}$ = CH$_2$CH$_3$ |
| 191 | Br | SMe | SMe | Formula (A1-5), n = 2, $R^{A12}$ = CH$_2$CH$_3$ |
| 192 | Br | SMe | 2-SEt | Formula (A1-5), n = 2, $R^{A12}$ = CH$_2$CH$_3$ |
| 193 | Br | SMe | 3-S"Pr | Formula (A1-5), n = 2, $R^{A12}$ = CH$_2$CH$_3$ |
| 194 | Br | SMe | 4-S"Bu | Formula (A1-5), n = 2, $R^{A12}$ = CH$_2$CH$_3$ |
| 195 | Br | 2-SEt | 2-SEt | Formula (A1-5), n = 2, $R^{A12}$ = CH$_2$CH$_3$ |
| 196 | Br | 2-SEt | 3-S"Pr | Formula (A1-5), n = 2, $R^{A12}$ = CH$_2$CH$_3$ |
| 197 | Br | 2-SEt | 4-S"Bu | Formula (A1-5), n = 2, $R^{A12}$ = CH$_2$CH$_3$ |
| 198 | Br | 3-S"Pr | 3-S"Pr | Formula (A1-5), n = 2, $R^{A12}$ = CH$_2$CH$_3$ |
| 199 | Br | 3-S"Pr | 4-S"Bu | Formula (A1-5), n = 2, $R^{A12}$ = CH$_2$CH$_3$ |
| 200 | Br | 4-S"Bu | 4-S"Bu | Formula (A1-5), n = 2, $R^{A12}$ = CH$_2$CH$_3$ |
| 201 | Br | SMe | SMe | Formula (A1-5), n = 3, $R^{A12}$ = CH$_2$CH$_3$ |
| 202 | Br | SMe | 2-SEt | Formula (A1-5), n = 3, $R^{A12}$ = CH$_2$CH$_3$ |
| 203 | Br | SMe | 3-S"Pr | Formula (A1-5), n = 3, $R^{A12}$ = CH$_2$CH$_3$ |
| 204 | Br | SMe | 4-S"Bu | Formula (A1-5), n = 3, $R^{A12}$ = CH$_2$CH$_3$ |
| 205 | Br | 2-SEt | 2-SEt | Formula (A1-5), n = 3, $R^{A12}$ = CH$_2$CH$_3$ |
| 206 | Br | 2-SEt | 3-S"Pr | Formula (A1-5), n = 3, $R^{A12}$ = CH$_2$CH$_3$ |
| 207 | Br | 2-SEt | 4-S"Bu | Formula (A1-5), n = 3, $R^{A12}$ = CH$_2$CH$_3$ |
| 208 | Br | 3-S"Pr | 3-S"Pr | Formula (A1-5), n = 3, $R^{A12}$ = CH$_2$CH$_3$ |
| 209 | Br | 3-S"Pr | 4-S"Bu | Formula (A1-5), n = 3, $R^{A12}$ = CH$_2$CH$_3$ |
| 210 | Br | 4-S"Bu | 4-S"Bu | Formula (A1-5), n = 3, $R^{A12}$ = CH$_2$CH$_3$ |

TABLE 10

| No. | Q | R¹¹ | R¹² | A¹ |
|---|---|---|---|---|
| 211 | Br | SMe | SMe | Formula (A1-5), n = 4, $R^{A12}$ = CH$_2$CH$_3$ |
| 212 | Br | SMe | 2-SEt | Formula (A1-5), n = 4, $R^{A12}$ = CH$_2$CH$_3$ |
| 213 | Br | SMe | 3-S"Pr | Formula (A1-5), n = 4, $R^{A12}$ = CH$_2$CH$_3$ |
| 214 | Br | SMe | 4-S"Bu | Formula (A1-5), n = 4, $R^{A12}$ = CH$_2$CH$_3$ |
| 215 | Br | 2-SEt | 2-SEt | Formula (A1-5), n = 4, $R^{A12}$ = CH$_2$CH$_3$ |
| 216 | Br | 2-SEt | 3-S"Pr | Formula (A1-5), n = 4, $R^{A12}$ = CH$_2$CH$_3$ |
| 217 | Br | 2-SEt | 4-S"Bu | Formula (A1-5), n = 4, $R^{A12}$ = CH$_2$CH$_3$ |
| 218 | Br | 3-S"Pr | 3-S"Pr | Formula (A1-5), n = 4, $R^{A12}$ = CH$_2$CH$_3$ |
| 219 | Br | 3-S"Pr | 4-S"Bu | Formula (A1-5), n = 4, $R^{A12}$ = CH$_2$CH$_3$ |
| 220 | Br | 4-S"Bu | 4-S"Bu | Formula (A1-5), n = 4, $R^{A12}$ = CH$_2$CH$_3$ |
| 221 | Br | SMe | SMe | Formula (A1-5), n = 5, $R^{A12}$ = CH$_2$CH$_3$ |
| 222 | Br | SMe | 2-SEt | Formula (A1-5), n = 5, $R^{A12}$ = CH$_2$CH$_3$ |
| 223 | Br | SMe | 3-S"Pr | Formula (A1-5), n = 5, $R^{A12}$ = CH$_2$CH$_3$ |
| 224 | Br | SMe | 4-S"Bu | Formula (A1-5), n = 5, $R^{A12}$ = CH$_2$CH$_3$ |
| 225 | Br | 2-SEt | 2-SEt | Formula (A1-5), n = 5, $R^{A12}$ = CH$_2$CH$_3$ |
| 226 | Br | 2-SEt | 3-S"Pr | Formula (A1-5), n = 5, $R^{A12}$ = CH$_2$CH$_3$ |
| 227 | Br | 2-SEt | 4-S"Bu | Formula (A1-5), n = 5, $R^{A12}$ = CH$_2$CH$_3$ |
| 228 | Br | 3-S"Pr | 3-S"Pr | Formula (A1-5), n = 5, $R^{A12}$ = CH$_2$CH$_3$ |
| 229 | Br | 3-S"Pr | 4-S"Bu | Formula (A1-5), n = 5, $R^{A12}$ = CH$_2$CH$_3$ |
| 230 | Br | 4-S"Bu | 4-S"Bu | Formula (A1-5), n = 5, $R^{A12}$ = CH$_2$CH$_3$ |
| 231 | Br | SMe | SMe | Formula (A1-5), n = 6, $R^{A12}$ = CH$_2$CH$_3$ |
| 232 | Br | SMe | 2-SEt | Formula (A1-5), n = 6, $R^{A12}$ = CH$_2$CH$_3$ |
| 233 | Br | SMe | 3-S"Pr | Formula (A1-5), n = 6, $R^{A12}$ = CH$_2$CH$_3$ |
| 234 | Br | SMe | 4-S"Bu | Formula (A1-5), n = 6, $R^{A12}$ = CH$_2$CH$_3$ |
| 235 | Br | 2-SEt | 2-SEt | Formula (A1-5), n = 6, $R^{A12}$ = CH$_2$CH$_3$ |
| 236 | Br | 2-SEt | 3-S"Pr | Formula (A1-5), n = 6, $R^{A12}$ = CH$_2$CH$_3$ |
| 237 | Br | 2-SEt | 4-S"Bu | Formula (A1-5), n = 6, $R^{A12}$ = CH$_2$CH$_3$ |
| 238 | Br | 3-S"Pr | 3-S"Pr | Formula (A1-5), n = 6, $R^{A12}$ = CH$_2$CH$_3$ |
| 239 | Br | 3-S"Pr | 4-S"Bu | Formula (A1-5), n = 6, $R^{A12}$ = CH$_2$CH$_3$ |
| 240 | Br | 4-S"Bu | 4-S"Bu | Formula (A1-5), n = 6, $R^{A12}$ = CH$_2$CH$_3$ |

TABLE 11

| No. | Q | R¹¹ | R¹² | A¹ |
|---|---|---|---|---|
| 241 | F | SMe | SMe | Formula (A1-5), n = 1, $R^{A12}$ = CH$_3$ |
| 242 | F | SMe | 2-SEt | Formula (A1-5), n = 1, $R^{A12}$ = CH$_3$ |
| 243 | F | SMe | 3-S"Pr | Formula (A1-5), n = 1, $R^{A12}$ = CH$_3$ |
| 244 | F | SMe | 4-S"Bu | Formula (A1-5), n = 1, $R^{A12}$ = CH$_3$ |
| 245 | F | 2-SEt | 2-SEt | Formula (A1-5), n = 1, $R^{A12}$ = CH$_3$ |
| 246 | F | 2-SEt | 3-S"Pr | Formula (A1-5), n = 1, $R^{A12}$ = CH$_3$ |
| 247 | F | 2-SEt | 4-S"Bu | Formula (A1-5), n = 1, $R^{A12}$ = CH$_3$ |
| 248 | F | 3-S"Pr | 3-S"Pr | Formula (A1-5), n = 1, $R^{A12}$ = CH$_3$ |
| 249 | F | 3-S"Pr | 4-S"Bu | Formula (A1-5), n = 1, $R^{A12}$ = CH$_3$ |
| 250 | F | 4-S"Bu | 4-S"Bu | Formula (A1-5), n = 1, $R^{A12}$ = CH$_3$ |
| 251 | F | SMe | SMe | Formula (A1-5), n = 2, $R^{A12}$ = CH$_3$ |
| 252 | F | SMe | 2-SEt | Formula (A1-5), n = 2, $R^{A12}$ = CH$_3$ |
| 253 | F | SMe | 3-S"Pr | Formula (A1-5), n = 2, $R^{A12}$ = CH$_3$ |
| 254 | F | SMe | 4-S"Bu | Formula (A1-5), n = 2, $R^{A12}$ = CH$_3$ |
| 255 | F | 2-SEt | 2-SEt | Formula (A1-5), n = 2, $R^{A12}$ = CH$_3$ |
| 256 | F | 2-SEt | 3-S"Pr | Formula (A1-5), n = 2, $R^{A12}$ = CH$_3$ |
| 257 | F | 2-SEt | 4-S"Bu | Formula (A1-5), n = 2, $R^{A12}$ = CH$_3$ |
| 258 | F | 3-S"Pr | 3-S"Pr | Formula (A1-5), n = 2, $R^{A12}$ = CH$_3$ |
| 259 | F | 3-S"Pr | 4-S"Bu | Formula (A1-5), n = 2, $R^{A12}$ = CH$_3$ |
| 260 | F | 4-S"Bu | 4-S"Bu | Formula (A1-5), n = 2, $R^{A12}$ = CH$_3$ |
| 261 | F | SMe | SMe | Formula (A1-5), n = 3, $R^{A12}$ = CH$_3$ |
| 262 | F | SMe | 2-SEt | Formula (A1-5), n = 3, $R^{A12}$ = CH$_3$ |
| 263 | F | SMe | 3-S"Pr | Formula (A1-5), n = 3, $R^{A12}$ = CH$_3$ |
| 264 | F | SMe | 4-S"Bu | Formula (A1-5), n = 3, $R^{A12}$ = CH$_3$ |
| 265 | F | 2-SEt | 2-SEt | Formula (A1-5), n = 3, $R^{A12}$ = CH$_3$ |
| 266 | F | 2-SEt | 3-S"Pr | Formula (A1-5), n = 3, $R^{A12}$ = CH$_3$ |
| 267 | F | 2-SEt | 4-S"Bu | Formula (A1-5), n = 3, $R^{A12}$ = CH$_3$ |
| 268 | F | 3-S"Pr | 3-S"Pr | Formula (A1-5), n = 3, $R^{A12}$ = CH$_3$ |
| 269 | F | 3-S"Pr | 4-S"Bu | Formula (A1-5), n = 3, $R^{A12}$ = CH$_3$ |
| 270 | F | 4-S"Bu | 4-S"Bu | Formula (A1-5), n = 3, $R^{A12}$ = CH$_3$ |

TABLE 12

| No. | Q | R¹¹ | R¹² | A¹ |
|---|---|---|---|---|
| 271 | F | SMe | SMe | Formula (A1-5), n = 4, $R^{A12}$ = CH$_3$ |
| 272 | F | SMe | 2-SEt | Formula (A1-5), n = 4, $R^{A12}$ = CH$_3$ |
| 273 | F | SMe | 3-S"Pr | Formula (A1-5), n = 4, $R^{A12}$ = CH$_3$ |
| 274 | F | SMe | 4-S"Bu | Formula (A1-5), n = 4, $R^{A12}$ = CH$_3$ |
| 275 | F | 2-SEt | 2-SEt | Formula (A1-5), n = 4, $R^{A12}$ = CH$_3$ |
| 276 | F | 2-SEt | 3-S"Pr | Formula (A1-5), n = 4, $R^{A12}$ = CH$_3$ |
| 277 | F | 2-SEt | 4-S"Bu | Formula (A1-5), n = 4, $R^{A12}$ = CH$_3$ |
| 278 | F | 3-S"Pr | 3-S"Pr | Formula (A1-5), n = 4, $R^{A12}$ = CH$_3$ |
| 279 | F | 3-S"Pr | 4-S"Bu | Formula (A1-5), n = 4, $R^{A12}$ = CH$_3$ |
| 280 | F | 4-S"Bu | 4-S"Bu | Formula (A1-5), n = 4, $R^{A12}$ = CH$_3$ |
| 281 | F | SMe | SMe | Formula (A1-5), n = 5, $R^{A12}$ = CH$_3$ |
| 282 | F | SMe | 2-SEt | Formula (A1-5), n = 5, $R^{A12}$ = CH$_3$ |
| 283 | F | SMe | 3-S"Pr | Formula (A1-5), n = 5, $R^{A12}$ = CH$_3$ |
| 284 | F | SMe | 4-S"Bu | Formula (A1-5), n = 5, $R^{A12}$ = CH$_3$ |
| 285 | F | 2-SEt | 2-SEt | Formula (A1-5), n = 5, $R^{A12}$ = CH$_3$ |
| 286 | F | 2-SEt | 3-S"Pr | Formula (A1-5), n = 5, $R^{A12}$ = CH$_3$ |
| 287 | F | 2-SEt | 4-S"Bu | Formula (A1-5), n = 5, $R^{A12}$ = CH$_3$ |
| 288 | F | 3-S"Pr | 3-S"Pr | Formula (A1-5), n = 5, $R^{A12}$ = CH$_3$ |
| 289 | F | 3-S"Pr | 4-S"Bu | Formula (A1-5), n = 5, $R^{A12}$ = CH$_3$ |
| 290 | F | 4-S"Bu | 4-S"Bu | Formula (A1-5), n = 5, $R^{A12}$ = CH$_3$ |
| 291 | F | SMe | SMe | Formula (A1-5), n = 6, $R^{A12}$ = CH$_3$ |
| 292 | F | SMe | 2-SEt | Formula (A1-5), n = 6, $R^{A12}$ = CH$_3$ |
| 293 | F | SMe | 3-S"Pr | Formula (A1-5), n = 6, $R^{A12}$ = CH$_3$ |
| 294 | F | SMe | 4-S"Bu | Formula (A1-5), n = 6, $R^{A12}$ = CH$_3$ |
| 295 | F | 2-SEt | 2-SEt | Formula (A1-5), n = 6, $R^{A12}$ = CH$_3$ |
| 296 | F | 2-SEt | 3-S"Pr | Formula (A1-5), n = 6, $R^{A12}$ = CH$_3$ |
| 297 | F | 2-SEt | 4-S"Bu | Formula (A1-5), n = 6, $R^{A12}$ = CH$_3$ |
| 298 | F | 3-S"Pr | 3-S"Pr | Formula (A1-5), n = 6, $R^{A12}$ = CH$_3$ |
| 299 | F | 3-S"Pr | 4-S"Bu | Formula (A1-5), n = 6, $R^{A12}$ = CH$_3$ |
| 300 | F | 4-S"Bu | 4-S"Bu | Formula (A1-5), n = 6, $R^{A12}$ = CH$_3$ |

TABLE 13

| No. | Q | R¹¹ | R¹² | A¹ |
|---|---|---|---|---|
| 301 | F | SMe | SMe | Formula (A1-5), n = 1, $R^{A12}$ = CH$_2$CH$_3$ |
| 302 | F | SMe | 2-SEt | Formula (A1-5), n = 1, $R^{A12}$ = CH$_2$CH$_3$ |
| 303 | F | SMe | 3-S"Pr | Formula (A1-5), n = 1, $R^{A12}$ = CH$_2$CH$_3$ |
| 304 | F | SMe | 4-S"Bu | Formula (A1-5), n = 1, $R^{A12}$ = CH$_2$CH$_3$ |
| 305 | F | 2-SEt | 2-SEt | Formula (A1-5), n = 1, $R^{A12}$ = CH$_2$CH$_3$ |
| 306 | F | 2-SEt | 3-S"Pr | Formula (A1-5), n = 1, $R^{A12}$ = CH$_2$CH$_3$ |
| 307 | F | 2-SEt | 4-S"Bu | Formula (A1-5), n = 1, $R^{A12}$ = CH$_2$CH$_3$ |
| 308 | F | 3-S"Pr | 3-S"Pr | Formula (A1-5), n = 1, $R^{A12}$ = CH$_2$CH$_3$ |
| 309 | F | 3-S"Pr | 4-S"Bu | Formula (A1-5), n = 1, $R^{A12}$ = CH$_2$CH$_3$ |
| 310 | F | 4-S"Bu | 4-S"Bu | Formula (A1-5), n = 1, $R^{A12}$ = CH$_2$CH$_3$ |
| 311 | F | SMe | SMe | Formula (A1-5), n = 2, $R^{A12}$ = CH$_2$CH$_3$ |
| 312 | F | SMe | 2-SEt | Formula (A1-5), n = 2, $R^{A12}$ = CH$_2$CH$_3$ |
| 313 | F | SMe | 3-S"Pr | Formula (A1-5), n = 2, $R^{A12}$ = CH$_2$CH$_3$ |
| 314 | F | SMe | 4-S"Bu | Formula (A1-5), n = 2, $R^{A12}$ = CH$_2$CH$_3$ |
| 315 | F | 2-SEt | 2-SEt | Formula (A1-5), n = 2, $R^{A12}$ = CH$_2$CH$_3$ |

TABLE 13-continued

| No. | Q | R$^{11}$ | R$^{12}$ | A$^1$ |
|---|---|---|---|---|
| 316 | F | 2-SEt | 3-S"Pr | Formula (A1-5), n = 2, R$^{412}$ = CH$_2$CH$_3$ |
| 317 | F | 2-SEt | 4-S"Bu | Formula (A1-5), n = 2, R$^{412}$ = CH$_2$CH$_3$ |
| 318 | F | 3-S"Pr | 3-S"Pr | Formula (A1-5), n = 2, R$^{412}$ = CH$_2$CH$_3$ |
| 319 | F | 3-S"Pr | 4-S"Bu | Formula (A1-5), n = 2, R$^{412}$ = CH$_2$CH$_3$ |
| 320 | F | 4-S"Bu | 4-S"Bu | Formula (A1-5), n = 2, R$^{412}$ = CH$_2$CH$_3$ |
| 321 | F | SMe | SMe | Formula (A1-5), n = 3, R$^{412}$ = CH$_2$CH$_3$ |
| 322 | F | SMe | 2-SEt | Formula (A1-5), n = 3, R$^{412}$ = CH$_2$CH$_3$ |
| 323 | F | SMe | 3-S"Pr | Formula (A1-5), n = 3, R$^{412}$ = CH$_2$CH$_3$ |
| 324 | F | SMe | 4-S"Bu | Formula (A1-5), n = 3, R$^{412}$ = CH$_2$CH$_3$ |
| 325 | F | 2-SEt | 2-SEt | Formula (A1-5), n = 3, R$^{412}$ = CH$_2$CH$_3$ |
| 326 | F | 2-SEt | 3-S"Pr | Formula (A1-5), n = 3, R$^{412}$ = CH$_2$CH$_3$ |
| 327 | F | 2-SEt | 4-S"Bu | Formula (A1-5), n = 3, R$^{412}$ = CH$_2$CH$_3$ |
| 328 | F | 3-S"Pr | 3-S"Pr | Formula (A1-5), n = 3, R$^{412}$ = CH$_2$CH$_3$ |
| 329 | F | 3-S"Pr | 4-S"Bu | Formula (A1-5), n = 3, R$^{412}$ = CH$_2$CH$_3$ |
| 330 | F | 4-S"Bu | 4-S"Bu | Formula (A1-5), n = 3, R$^{412}$ = CH$_2$CH$_3$ |

TABLE 14

| No. | Q | R$^{11}$ | R$^{12}$ | A$^1$ |
|---|---|---|---|---|
| 331 | F | SMe | SMe | Formula (A1-5), n = 4, R$^{412}$ = CH$_2$CH$_3$ |
| 332 | F | SMe | 2-SEt | Formula (A1-5), n = 4, R$^{412}$ = CH$_2$CH$_3$ |
| 333 | F | SMe | 3-S"Pr | Formula (A1-5), n = 4, R$^{412}$ = CH$_2$CH$_3$ |
| 334 | F | SMe | 4-S"Bu | Formula (A1-5), n = 4, R$^{412}$ = CH$_2$CH$_3$ |
| 335 | F | 2-SEt | 2-SEt | Formula (A1-5), n = 4, R$^{412}$ = CH$_2$CH$_3$ |
| 336 | F | 2-SEt | 3-S"Pr | Formula (A1-5), n = 4, R$^{412}$ = CH$_2$CH$_3$ |
| 337 | F | 2-SEt | 4-S"Bu | Formula (A1-5), n = 4, R$^{412}$ = CH$_2$CH$_3$ |
| 338 | F | 3-S"Pr | 3-S"Pr | Formula (A1-5), n = 4, R$^{412}$ = CH$_2$CH$_3$ |
| 339 | F | 3-S"Pr | 4-S"Bu | Formula (A1-5), n = 4, R$^{412}$ = CH$_2$CH$_3$ |
| 340 | F | 4-S"Bu | 4-S"Bu | Formula (A1-5), n = 4, R$^{412}$ = CH$_2$CH$_3$ |
| 341 | F | SMe | SMe | Formula (A1-5), n = 5, R$^{412}$ = CH$_2$CH$_3$ |
| 342 | F | SMe | 2-SEt | Formula (A1-5), n = 5, R$^{412}$ = CH$_2$CH$_3$ |
| 343 | F | SMe | 3-S"Pr | Formula (A1-5), n = 5, R$^{412}$ = CH$_2$CH$_3$ |
| 344 | F | SMe | 4-S"Bu | Formula (A1-5), n = 5, R$^{412}$ = CH$_2$CH$_3$ |
| 345 | F | 2-SEt | 2-SEt | Formula (A1-5), n = 5, R$^{412}$ = CH$_2$CH$_3$ |
| 346 | F | 2-SEt | 3-S"Pr | Formula (A1-5), n = 5, R$^{412}$ = CH$_2$CH$_3$ |
| 347 | F | 2-SEt | 4-S"Bu | Formula (A1-5), n = 5, R$^{412}$ = CH$_2$CH$_3$ |
| 348 | F | 3-S"Pr | 3-S"Pr | Formula (A1-5), n = 5, R$^{412}$ = CH$_2$CH$_3$ |
| 349 | F | 3-S"Pr | 4-S"Bu | Formula (A1-5), n = 5, R$^{412}$ = CH$_2$CH$_3$ |
| 350 | F | 4-S"Bu | 4-S"Bu | Formula (A1-5), n = 5, R$^{412}$ = CH$_2$CH$_3$ |
| 351 | F | SMe | SMe | Formula (A1-5), n = 6, R$^{412}$ = CH$_2$CH$_3$ |
| 352 | F | SMe | 2-SEt | Formula (A1-5), n = 6, R$^{412}$ = CH$_2$CH$_3$ |
| 353 | F | SMe | 3-S"Pr | Formula (A1-5), n = 6, R$^{412}$ = CH$_2$CH$_3$ |
| 354 | F | SMe | 4-S"Bu | Formula (A1-5), n = 6, R$^{412}$ = CH$_2$CH$_3$ |
| 355 | F | 2-SEt | 2-SEt | Formula (A1-5), n = 6, R$^{412}$ = CH$_2$CH$_3$ |
| 356 | F | 2-SEt | 3-S"Pr | Formula (A1-5), n = 6, R$^{412}$ = CH$_2$CH$_3$ |
| 357 | F | 2-SEt | 4-S"Bu | Formula (A1-5), n = 6, R$^{412}$ = CH$_2$CH$_3$ |
| 358 | F | 3-S"Pr | 3-S"Pr | Formula (A1-5), n = 6, R$^{412}$ = CH$_2$CH$_3$ |
| 359 | F | 3-S"Pr | 4-S"Bu | Formula (A1-5), n = 6, R$^{412}$ = CH$_2$CH$_3$ |
| 360 | F | 4-S"Bu | 4-S"Bu | Formula (A1-5), n = 6, R$^{412}$ = CH$_2$CH$_3$ |

When A$^1$ in the above formula (1) is a C1-C3 alkoxy-substituted alkylamino group, preferred compounds include, for example, one in which in the above formula (1-1), Q is a chlorine atom, x is 3, A$^1$ is a group represented by the above formula (A1-5), and n in the above formula (A1-5) is 3.

(C1-C6 Alkyl-Monosubstituted Amino Group)

Specific examples of a C1-C6 alkyl-monosubstituted amino group include, for example, a monomethylamino group, a monoethylamino group, a mono-n-propylamino group, a monoisopropylamino group, a mono-n-butylamino group, a mono-s-butylamino group, a mono-t-butylamino group, a mono-n-pentylamino group, a mono-n-hexylamino group and the like. Among these, a C1-C4 alkyl-monosubstituted amino group is preferred, and a linear C1-C4 alkyl-monosubstituted amino group is more preferred such as a monomethylamino group, a monoethylamino group, a mono-n-propylamino group, a mono-n-butylamino group.

Specific examples of a compound in which A$^1$ in the above formula (1) is a C1-C6 alkyl-monosubstituted amino group are shown in Tables 15 to 20 below. However, the present invention shall not be limited to these specific examples. Abbreviations in Tables 15 to 20 have the following meanings.

SMe: sulfomethyl (*—CH$_2$—SO$_3$H)
2-SEt: 2-sulfoethyl (*—CH$_2$CH$_2$—SO$_3$H)
3-S"Pr: 3-sulfo-n-propyl (*—CH$_2$CH$_2$CH$_2$—SO$_3$H)
4-S"Bu: 3-sulfo-n-butyl (*—CH$_2$CH$_2$CH$_2$CH$_2$—SO$_3$H)

The symbol "*" in the above formulae indicates a position of attachment to the oxygen atom.

TABLE 15

| No. | Q | R$^{11}$ | R$^{12}$ | A$^1$ |
|---|---|---|---|---|
| 1 | Cl | SMe | SMe | NHCH$_3$ |
| 2 | Cl | SMe | 2-SEt | NHCH$_3$ |
| 3 | Cl | SMe | 3-S"Pr | NHCH$_3$ |
| 4 | Cl | SMe | 4-S"Bu | NHCH$_3$ |
| 5 | Cl | 2-SEt | 2-SEt | NHCH$_3$ |
| 6 | Cl | 2-SEt | 3-S"Pr | NHCH$_3$ |
| 7 | Cl | 2-SEt | 4-S"Bu | NHCH$_3$ |
| 8 | Cl | 3-S"Pr | 3-S"Pr | NHCH$_3$ |
| 9 | Cl | 3-S"Pr | 4-S"Bu | NHCH$_3$ |
| 10 | Cl | 4-S"Bu | 4-S"Bu | NHCH$_3$ |
| 11 | Cl | SMe | SMe | NHC$_2$H$_5$ |
| 12 | Cl | SMe | 2-SEt | NHC$_2$H$_5$ |
| 13 | Cl | SMe | 3-S"Pr | NHC$_2$H$_5$ |
| 14 | Cl | SMe | 4-S"Bu | NHC$_2$H$_5$ |
| 15 | Cl | 2-SEt | 2-SEt | NHC$_2$H$_5$ |
| 16 | Cl | 2-SEt | 3-S"Pr | NHC$_2$H$_5$ |
| 17 | Cl | 2-SEt | 4-S"Bu | NHC$_2$H$_5$ |
| 18 | Cl | 3-S"Pr | 3-S"Pr | NHC$_2$H$_5$ |
| 19 | Cl | 3-S"Pr | 4-S"Bu | NHC$_2$H$_5$ |
| 20 | Cl | 4-S"Bu | 4-S"Bu | NHC$_2$H$_5$ |
| 21 | Cl | SMe | SMe | NHC$_3$H$_7$ |
| 22 | Cl | SMe | 2-SEt | NHC$_3$H$_7$ |
| 23 | Cl | SMe | 3-S"Pr | NHC$_3$H$_7$ |
| 24 | Cl | SMe | 4-S"Bu | NHC$_3$H$_7$ |
| 25 | Cl | 2-SEt | 2-SEt | NHC$_3$H$_7$ |
| 26 | Cl | 2-SEt | 3-S"Pr | NHC$_3$H$_7$ |
| 27 | Cl | 2-SEt | 4-S"Bu | NHC$_3$H$_7$ |
| 28 | Cl | 3-S"Pr | 3-S"Pr | NHC$_3$H$_7$ |
| 29 | Cl | 3-S"Pr | 4-S"Bu | NHC$_3$H$_7$ |
| 30 | Cl | 4-S"Bu | 4-S"Bu | NHC$_3$H$_7$ |

TABLE 16

| No. | Q | R$^{11}$ | R$^{12}$ | A$^1$ |
|---|---|---|---|---|
| 31 | Cl | SMe | SMe | NHC$_4$H$_9$ |
| 32 | Cl | SMe | 2-SEt | NHC$_4$H$_9$ |
| 33 | Cl | SMe | 3-S"Pr | NHC$_4$H$_9$ |
| 34 | Cl | SMe | 4-S"Bu | NHC$_4$H$_9$ |
| 35 | Cl | 2-SEt | 2-SEt | NHC$_4$H$_9$ |
| 36 | Cl | 2-SEt | 3-S"Pr | NHC$_4$H$_9$ |
| 37 | Cl | 2-SEt | 4-S"Bu | NHC$_4$H$_9$ |
| 38 | Cl | 3-S"Pr | 3-S"Pr | NHC$_4$H$_9$ |
| 39 | Cl | 3-S"Pr | 4-S"Bu | NHC$_4$H$_9$ |
| 40 | Cl | 4-S"Bu | 4-S"Bu | NHC$_4$H$_9$ |
| 41 | Cl | SMe | SMe | NHC$_5$H$_{11}$ |
| 42 | Cl | SMe | 2-SEt | NHC$_5$H$_{11}$ |
| 43 | Cl | SMe | 3-S"Pr | NHC$_5$H$_{11}$ |
| 44 | Cl | SMe | 4-S"Bu | NHC$_5$H$_{11}$ |
| 45 | Cl | 2-SEt | 2-SEt | NHC$_5$H$_{11}$ |
| 46 | Cl | 2-SEt | 3-S"Pr | NHC$_5$H$_{11}$ |
| 47 | Cl | 2-SEt | 4-S"Bu | NHC$_5$H$_{11}$ |
| 48 | Cl | 3-S"Pr | 3-S"Pr | NHC$_5$H$_{11}$ |
| 49 | Cl | 3-S"Pr | 4-S"Bu | NHC$_5$H$_{11}$ |
| 50 | Cl | 4-S"Bu | 4-S"Bu | NHC$_5$H$_{11}$ |
| 51 | Cl | SMe | SMe | NHC$_6$H$_{13}$ |
| 52 | Cl | SMe | 2-SEt | NHC$_6$H$_{13}$ |
| 53 | Cl | SMe | 3-S"Pr | NHC$_6$H$_{13}$ |
| 54 | Cl | SMe | 4-S"Bu | NHC$_6$H$_{13}$ |
| 55 | Cl | 2-SEt | 2-SEt | NHC$_6$H$_{13}$ |
| 56 | Cl | 2-SEt | 3-S"Pr | NHC$_6$H$_{13}$ |
| 57 | Cl | 2-SEt | 4-S"Bu | NHC$_6$H$_{13}$ |

TABLE 16-continued

| No. | Q | R11 | R12 | A1 |
|---|---|---|---|---|
| 58 | Cl | 3-S"Pr | 3-S"Pr | NHC6H13 |
| 59 | Cl | 3-S"Pr | 4-S"Bu | NHC6H13 |
| 60 | Cl | 4-S"Bu | 4-S"Bu | NHC6H13 |

TABLE 17

| No. | Q | R11 | R12 | A1 |
|---|---|---|---|---|
| 61 | Br | SMe | SMe | NHCH3 |
| 62 | Br | SMe | 2-SEt | NHCH3 |
| 63 | Br | SMe | 3-S"Pr | NHCH3 |
| 64 | Br | SMe | 4-S"Bu | NHCH3 |
| 65 | Br | 2-SEt | 2-SEt | NHCH3 |
| 66 | Br | 2-SEt | 3-S"Pr | NHCH3 |
| 67 | Br | 2-SEt | 4-S"Bu | NHCH3 |
| 68 | Br | 3-S"Pr | 3-S"Pr | NHCH3 |
| 69 | Br | 3-S"Pr | 4-S"Bu | NHCH3 |
| 70 | Br | 4-S"Bu | 4-S"Bu | NHCH3 |
| 71 | Br | SMe | SMe | NHC2H5 |
| 72 | Br | SMe | 2-SEt | NHC2H5 |
| 73 | Br | SMe | 3-S"Pr | NHC2H5 |
| 74 | Br | SMe | 4-S"Bu | NHC2H5 |
| 75 | Br | 2-SEt | 2-SEt | NHC2H5 |
| 76 | Br | 2-SEt | 3-S"Pr | NHC2H5 |
| 77 | Br | 2-SEt | 4-S"Bu | NHC2H5 |
| 78 | Br | 3-S"Pr | 3-S"Pr | NHC2H5 |
| 79 | Br | 3-S"Pr | 4-S"Bu | NHC2H5 |
| 80 | Br | 4-S"Bu | 4-S"Bu | NHC2H5 |
| 81 | Br | SMe | SMe | NHC3H7 |
| 82 | Br | SMe | 2-SEt | NHC3H7 |
| 83 | Br | SMe | 3-S"Pr | NHC3H7 |
| 84 | Br | SMe | 4-S"Bu | NHC3H7 |
| 85 | Br | 2-SEt | 2-SEt | NHC3H7 |
| 86 | Br | 2-SEt | 3-S"Pr | NHC3H7 |
| 87 | Br | 2-SEt | 4-S"Bu | NHC3H7 |
| 88 | Br | 3-S"Pr | 3-S"Pr | NHC3H7 |
| 89 | Br | 3-S"Pr | 4-S"Bu | NHC3H7 |
| 90 | Br | 4-S"Bu | 4-S"Bu | NHC3H7 |

TABLE 18

| No. | Q | R11 | R12 | A1 |
|---|---|---|---|---|
| 91 | Br | SMe | SMe | NHC4H9 |
| 92 | Br | SMe | 2-SEt | NHC4H9 |
| 93 | Br | SMe | 3-S"Pr | NHC4H9 |
| 94 | Br | SMe | 4-S"Bu | NHC4H9 |
| 95 | Br | 2-SEt | 2-SEt | NHC4H9 |
| 96 | Br | 2-SEt | 3-S"Pr | NHC4H9 |
| 97 | Br | 2-SEt | 4-S"Bu | NHC4H9 |
| 98 | Br | 3-S"Pr | 3-S"Pr | NHC4H9 |
| 99 | Br | 3-S"Pr | 4-S"Bu | NHC4H9 |
| 100 | Br | 4-S"Bu | 4-S"Bu | NHC4H9 |
| 101 | Br | SMe | SMe | NHC5H11 |
| 102 | Br | SMe | 2-SEt | NHC5H11 |
| 103 | Br | SMe | 3-S"Pr | NHC5H11 |
| 104 | Br | SMe | 4-S"Bu | NHC5H11 |
| 105 | Br | 2-SEt | 2-SEt | NHC5H11 |
| 106 | Br | 2-SEt | 3-S"Pr | NHC5H11 |
| 107 | Br | 2-SEt | 4-S"Bu | NHC5H11 |
| 108 | Br | 3-S"Pr | 3-S"Pr | NHC5H11 |
| 109 | Br | 3-S"Pr | 4-S"Bu | NHC5H11 |
| 110 | Br | 4-S"Bu | 4-S"Bu | NHC5H11 |
| 111 | Br | SMe | SMe | NHC6H13 |
| 112 | Br | SMe | 2-SEt | NHC6H13 |
| 113 | Br | SMe | 3-S"Pr | NHC6H13 |
| 114 | Br | SMe | 4-S"Bu | NHC6H13 |
| 115 | Br | 2-SEt | 2-SEt | NHC6H13 |
| 116 | Br | 2-SEt | 3-S"Pr | NHC6H13 |
| 117 | Br | 2-SEt | 4-S"Bu | NHC6H13 |
| 118 | Br | 3-S"Pr | 3-S"Pr | NHC6H13 |
| 119 | Br | 3-S"Pr | 4-S"Bu | NHC6H13 |
| 120 | Br | 4-S"Bu | 4-S"Bu | NHC6H13 |

TABLE 19

| No. | Q | R11 | R12 | A1 |
|---|---|---|---|---|
| 121 | F | SMe | SMe | NHCH3 |
| 122 | F | SMe | 2-SEt | NHCH3 |
| 123 | F | SMe | 3-S"Pr | NHCH3 |
| 124 | F | SMe | 4-S"Bu | NHCH3 |
| 125 | F | 2-SEt | 2-SEt | NHCH3 |
| 126 | F | 2-SEt | 3-S"Pr | NHCH3 |
| 127 | F | 2-SEt | 4-S"Bu | NHCH3 |
| 128 | F | 3-S"Pr | 3-S"Pr | NHCH3 |
| 129 | F | 3-S"Pr | 4-S"Bu | NHCH3 |
| 130 | F | 4-S"Bu | 4-S"Bu | NHCH3 |
| 131 | F | SMe | SMe | NHC2H5 |
| 132 | F | SMe | 2-SEt | NHC2H5 |
| 133 | F | SMe | 3-S"Pr | NHC2H5 |
| 134 | F | SMe | 4-S"Bu | NHC2H5 |
| 135 | F | 2-SEt | 2-SEt | NHC2H5 |
| 136 | F | 2-SEt | 3-S"Pr | NHC2H5 |
| 137 | F | 2-SEt | 4-S"Bu | NHC2H5 |
| 138 | F | 3-S"Pr | 3-S"Pr | NHC2H5 |
| 139 | F | 3-S"Pr | 4-S"Bu | NHC2H5 |
| 140 | F | 4-S"Bu | 4-S"Bu | NHC2H5 |
| 141 | F | SMe | SMe | NHC3H7 |
| 142 | F | SMe | 2-SEt | NHC3H7 |
| 143 | F | SMe | 3-S"Pr | NHC3H7 |
| 144 | F | SMe | 4-S"Bu | NHC3H7 |
| 145 | F | 2-SEt | 2-SEt | NHC3H7 |
| 146 | F | 2-SEt | 3-S"Pr | NHC3H7 |
| 147 | F | 2-SEt | 4-S"Bu | NHC3H7 |
| 148 | F | 3-S"Pr | 3-S"Pr | NHC3H7 |
| 149 | F | 3-S"Pr | 4-S"Bu | NHC3H7 |
| 150 | F | 4-S"Bu | 4-S"Bu | NHC3H7 |

TABLE 20

| No. | Q | R11 | R12 | A1 |
|---|---|---|---|---|
| 151 | F | SMe | SMe | NHC4H9 |
| 152 | F | SMe | 2-SEt | NHC4H9 |
| 153 | F | SMe | 3-S"Pr | NHC4H9 |
| 154 | F | SMe | 4-S"Bu | NHC4H9 |
| 155 | F | 2-SEt | 2-SEt | NHC4H9 |
| 156 | F | 2-SEt | 3-S"Pr | NHC4H9 |
| 157 | F | 2-SEt | 4-S"Bu | NHC4H9 |
| 158 | F | 3-S"Pr | 3-S"Pr | NHC4H9 |
| 159 | F | 3-S"Pr | 4-S"Bu | NHC4H9 |
| 160 | F | 4-S"Bu | 4-S"Bu | NHC4H9 |
| 161 | F | SMe | SMe | NHC5H11 |
| 162 | F | SMe | 2-SEt | NHC5H11 |
| 163 | F | SMe | 3-S"Pr | NHC5H11 |
| 164 | F | SMe | 4-S"Bu | NHC5H11 |
| 165 | F | 2-SEt | 2-SEt | NHC5H11 |
| 166 | F | 2-SEt | 3-S"Pr | NHC5H11 |
| 167 | F | 2-SEt | 4-S"Bu | NHC5H11 |
| 168 | F | 3-S"Pr | 3-S"Pr | NHC5H11 |
| 169 | F | 3-S"Pr | 4-S"Bu | NHC5H11 |
| 170 | F | 4-S"Bu | 4-S"Bu | NHC5H11 |
| 171 | F | SMe | SMe | NHC6H13 |
| 172 | F | SMe | 2-SEt | NHC6H13 |
| 173 | F | SMe | 3-S"Pr | NHC6H13 |
| 174 | F | SMe | 4-S"Bu | NHC6H13 |
| 175 | F | 2-SEt | 2-SEt | NHC6H13 |
| 176 | F | 2-SEt | 3-S"Pr | NHC6H13 |
| 177 | F | 2-SEt | 4-S"Bu | NHC6H13 |
| 178 | F | 3-S"Pr | 3-S"Pr | NHC6H13 |
| 179 | F | 3-S"Pr | 4-S"Bu | NHC6H13 |
| 180 | F | 4-S"Bu | 4-S"Bu | NHC6H13 |

When $A^1$ in the above formula (1) is a C1-C6 alkyl-monosubstituted amino group, preferred compounds include, for example, one in which in the above formula (1-1), Q is a chlorine atom, x is 3, and $A^1$ is a C1-C4 alkyl-monosubstituted amino group. More preferred compounds include, for example, one in which in the above formula (1-1), Q is a chlorine atom, x is 3, and $A^1$ is a linear C1-C4 alky-monosubstituted amino group.

(C2-C6 Alkyl-Monosubstituted Amino Group Having Two or More Hydroxy Groups)

The number of substitutions in a hydroxy group of a C2-C6 alkyl-monosubstituted amino group having two or more hydroxy groups is usually 2 or 3, and preferably 2. The C2-C6 alkyl-monosubstituted amino group having two or more hydroxy groups is preferably a group represented by the above formula (A1-6). In the above formula (A1-6), $R^{413}$ represents a C2-C6 alkyl group having two or more hydroxy groups, preferably a C2-C4 alkyl group having two hydroxy groups.

Specific examples of a C2-C6 alkyl-monosubstituted amino group having two or more hydroxy groups include, for example, a linear C2-C6 alkyl-monosubstituted amino group having two or more hydroxy groups such as a 1,2-dihydroxyethylamino group, a 1,1-dihydroxyethylamino group, a 1,2-dihydroxypropylamino group, a 1,2-dihydroxybutylamino group, a 1,2-dihydroxypentylamino group, a 1,2-dihydroxyhexylamino group, and a 1,2,3-trihydroxyhexylamino group; a branched C2-C6 alkyl-monosubstituted amino group having two or more hydroxy groups such as a 1,1'-dihydroxyisopropylamino group and a 1,1'-dihydroxypentylamino group; and the like. Among these, preferred is a group represented by the above formula (A1-7) or (A1-8).

Specific examples of a compound in which $A^1$ in the above formula (1) is a C2-C6 alkyl-monosubstituted amino group having two or more hydroxy groups are shown in Tables 21 to 25. However, the present invention shall not be limited to these specific examples. Abbreviations in Tables 21 to 25 have the following meanings.

SMe: sulfomethyl (*—$CH_2$—$SO_3H$)

2-SEt: 2-sulfoethyl (*—$CH_2CH_2$—$SO_3H$)

3-S″Pr: 3-sulfo-n-propyl (*—$CH_2CH_2CH_2$—$SO_3H$)

4-S″Bu: 3-sulfo-n-butyl (*—$CH_2CH_2CH_2CH_2$—$SO_3H$)

The symbol "*" in the above formulae indicates a position of attachment to the oxygen atom.

TABLE 21

| No. | Q | $R^{11}$ | $R^{12}$ | $A^1$ |
|---|---|---|---|---|
| 1 | Cl | SMe | SMe | Formula (A1-7) |
| 2 | Cl | SMe | 2-SEt | Formula (A1-7) |
| 3 | Cl | SMe | 3-S″Pr | Formula (A1-7) |
| 4 | Cl | SMe | 4-S″Bu | Formula (A1-7) |
| 5 | Cl | 2-SEt | 2-SEt | Formula (A1-7) |
| 6 | Cl | 2-SEt | 3-S″Pr | Formula (A1-7) |
| 7 | Cl | 2-SEt | 4-S″Bu | Formula (A1-7) |
| 8 | Cl | 3-S″Pr | 3-S″Pr | Formula (A1-7) |
| 9 | Cl | 3-S″Pr | 4-S″Bu | Formula (A1-7) |
| 10 | Cl | 4-S″Bu | 4-S″Bu | Formula (A1-7) |
| 11 | Cl | SMe | SMe | Formula (A1-8) |
| 12 | Cl | SMe | 2-SEt | Formula (A1-8) |
| 13 | Cl | SMe | 3-S″Pr | Formula (A1-8) |
| 14 | Cl | SMe | 4-S″Bu | Formula (A1-8) |
| 15 | Cl | 2-SEt | 2-SEt | Formula (A1-8) |
| 16 | Cl | 2-SEt | 3-S″Pr | Formula (A1-8) |
| 17 | Cl | 2-SEt | 4-S″Bu | Formula (A1-8) |
| 18 | Cl | 3-S″Pr | 3-S″Pr | Formula (A1-8) |
| 19 | Cl | 3-S″Pr | 4-S″Bu | Formula (A1-8) |
| 20 | Cl | 4-S″Bu | 4-S″Bu | Formula (A1-8) |
| 21 | Cl | SMe | SMe | Formula (A1-6), $R^{413}$ = CH(OH)CH$_2$(OH) |
| 22 | Cl | SMe | 2-SEt | Formula (A1-6), $R^{413}$ = CH(OH)CH$_2$(OH) |
| 23 | Cl | SMe | 3-S″Pr | Formula (A1-6), $R^{413}$ = CH(OH)CH$_2$(OH) |
| 24 | Cl | SMe | 4-S″Bu | Formula (A1-6), $R^{413}$ = CH(OH)CH$_2$(OH) |
| 25 | Cl | 2-SEt | 2-SEt | Formula (A1-6), $R^{413}$ = CH(OH)CH$_2$(OH) |
| 26 | Cl | 2-SEt | 3-S″Pr | Formula (A1-6), $R^{413}$ = CH(OH)CH$_2$(OH) |
| 27 | Cl | 2-SEt | 4-S″Bu | Formula (A1-6), $R^{413}$ = CH(OH)CH$_2$(OH) |
| 28 | Cl | 3-S″Pr | 3-S″Pr | Formula (A1-6), $R^{413}$ = CH(OH)CH$_2$(OH) |
| 29 | Cl | 3-S″Pr | 4-S″Bu | Formula (A1-6), $R^{413}$ = CH(OH)CH$_2$(OH) |
| 30 | Cl | 4-S″Bu | 4-S″Bu | Formula (A1-6), $R^{413}$ = CH(OH)CH$_2$(OH) |

TABLE 22

| No. | Q | $R^{11}$ | $R^{12}$ | $A^1$ |
|---|---|---|---|---|
| 31 | Cl | SMe | SMe | Formula (A1-6), $R^{413}$ = CH$_2$CH (OH) CH$_2$CH$_2$OH |
| 32 | Cl | SMe | 2-SEt | Formula (A1-6), $R^{413}$ = CH$_2$CH (OH) CH$_2$CH$_2$OH |
| 33 | Cl | SMe | 3-S″Pr | Formula (A1-6), $R^{413}$ = CH$_2$CH (OH) CH$_2$CH$_2$OH |
| 34 | Cl | SMe | 4-S″Bu | Formula (A1-6), $R^{413}$ = CH$_2$CH (OH) CH$_2$CH$_2$OH |
| 35 | Cl | 2-SEt | 2-SEt | Formula (A1-6), $R^{413}$ = CH$_2$CH (OH) CH$_2$CH$_2$OH |
| 36 | Cl | 2-SEt | 3-S″Pr | Formula (A1-6), $R^{413}$ = CH$_2$CH (OH) CH$_2$CH$_2$OH |
| 37 | Cl | 2-SEt | 4-S″Bu | Formula (A1-6), $R^{413}$ = CH$_2$CH (OH) CH$_2$CH$_2$OH |
| 38 | Cl | 3-S″Pr | 3-S″Pr | Formula (A1-6), $R^{413}$ = CH$_2$CH (OH) CH$_2$CH$_2$OH |
| 39 | Cl | 3-S″Pr | 4-S″Bu | Formula (A1-6), $R^{413}$ = CH$_2$CH (OH) CH$_2$CH$_2$OH |
| 40 | Cl | 4-S″Bu | 4-S″Bu | Formula (A1-6), $R^{413}$ = CH$_2$CH (OH) CH$_2$CH$_2$OH |
| 41 | Cl | SMe | SMe | Formula (A1-6), $R^{413}$ = CH$_2$CH$_2$CH (OH) CH$_2$CH$_2$OH |
| 42 | Cl | SMe | 2-SEt | Formula (A1-6), $R^{413}$ = CH$_2$CH$_2$CH (OH) CH$_2$CH$_2$OH |
| 43 | Cl | SMe | 3-S″Pr | Formula (A1-6), $R^{413}$ = CH$_2$CH$_2$CH (OH) CH$_2$CH$_2$OH |
| 44 | Cl | SMe | 4-S″Bu | Formula (A1-6), $R^{413}$ = CH$_2$CH$_2$CH (OH) CH$_2$CH$_2$OH |
| 45 | Cl | 2-SEt | 2-SEt | Formula (A1-6), $R^{413}$ = CH$_2$CH$_2$CH (OH) CH$_2$CH$_2$OH |
| 46 | Cl | 2-SEt | 3-S″Pr | Formula (A1-6), $R^{413}$ = CH$_2$CH$_2$CH (OH) CH$_2$CH$_2$OH |
| 47 | Cl | 2-SEt | 4-S″Bu | Formula (A1-6), $R^{413}$ = CH$_2$CH$_2$CH (OH) CH$_2$CH$_2$OH |
| 48 | Cl | 3-S″Pr | 3-S″Pr | Formula (A1-6), $R^{413}$ = CH$_2$CH$_2$CH (OH) CH$_2$CH$_2$OH |
| 49 | Cl | 3-S″Pr | 4-S″Bu | Formula (A1-6), $R^{413}$ = CH$_2$CH$_2$CH (OH) CH$_2$CH$_2$OH |
| 50 | Cl | 4-S″Bu | 4-S″Bu | Formula (A1-6), $R^{413}$ = CH$_2$CH$_2$CH (OH) CH$_2$CH$_2$OH |
| 51 | Br | SMe | SMe | Formula (A1-7) |
| 52 | Br | SMe | 2-SEt | Formula (A1-7) |
| 53 | Br | SMe | 3-S″Pr | Formula (A1-7) |
| 54 | Br | SMe | 4-S″Bu | Formula (A1-7) |
| 55 | Br | 2-SEt | 2-SEt | Formula (A1-7) |
| 56 | Br | 2-SEt | 3-S″Pr | Formula (A1-7) |
| 57 | Br | 2-SEt | 4-S″Bu | Formula (A1-7) |
| 58 | Br | 3-S″Pr | 3-S″Pr | Formula (A1-7) |

TABLE 22-continued

| No. | Q  | $R^{11}$ | $R^{12}$ | $A^1$         |
|-----|----|----------|----------|---------------|
| 59  | Br | 3-S"Pr   | 4-S"Bu   | Formula (A1-7)|
| 60  | Br | 4-S"Bu   | 4-S"Bu   | Formula (A1-7)|

TABLE 23

| No. | Q  | $R^{11}$ | $R^{12}$ | $A^1$ |
|-----|----|----------|----------|-------|
| 61 | Br | SMe    | SMe    | Formula (A1-8) |
| 62 | Br | SMe    | 2-SEt  | Formula (A1-8) |
| 63 | Br | SMe    | 3-S"Pr | Formula (A1-8) |
| 64 | Br | SMe    | 4-S"Bu | Formula (A1-8) |
| 65 | Br | 2-SEt  | 2-SEt  | Formula (A1-8) |
| 66 | Br | 2-SEt  | 3-S"Pr | Formula (A1-8) |
| 67 | Br | 2-SEt  | 4-S"Bu | Formula (A1-8) |
| 68 | Br | 3-S"Pr | 3-S"Pr | Formula (A1-8) |
| 69 | Br | 3-S"Pr | 4-S"Bu | Formula (A1-8) |
| 70 | Br | 4-S"Bu | 4-S"Bu | Formula (A1-8) |
| 71 | Br | SMe    | SMe    | Formula (A1-6), $R^{A13}$ = CH(OH)CH$_2$(OH) |
| 72 | Br | SMe    | 2-SEt  | Formula (A1-6), $R^{A13}$ = CH(OH)CH$_2$(OH) |
| 73 | Br | SMe    | 3-S"Pr | Formula (A1-6), $R^{A13}$ = CH(OH)CH$_2$(OH) |
| 74 | Br | SMe    | 4-S"Bu | Formula (A1-6), $R^{A13}$ = CH(OH)CH$_2$(OH) |
| 75 | Br | 2-SEt  | 2-SEt  | Formula (A1-6), $R^{A13}$ = CH(OH)CH$_2$(OH) |
| 76 | Br | 2-SEt  | 3-S"Pr | Formula (A1-6), $R^{A13}$ = CH(OH)CH$_2$(OH) |
| 77 | Br | 2-SEt  | 4-S"Bu | Formula (A1-6), $R^{A13}$ = CH(OH)CH$_2$(OH) |
| 78 | Br | 3-S"Pr | 3-S"Pr | Formula (A1-6), $R^{A13}$ = CH(OH)CH$_2$(OH) |
| 79 | Br | 3-S"Pr | 4-S"Bu | Formula (A1-6), $R^{A13}$ = CH(OH)CH$_2$(OH) |
| 80 | Br | 4-S"Bu | 4-S"Bu | Formula (A1-6), $R^{A13}$ = CH(OH)CH$_2$(OH) |
| 81 | Br | SMe    | SMe    | Formula (A1-6), $R^{A13}$ = CH$_2$CH(OH)CH$_2$CH$_2$OH |
| 82 | Br | SMe    | 2-SEt  | Formula (A1-6), $R^{A13}$ = CH$_2$CH(OH)CH$_2$CH$_2$OH |
| 83 | Br | SMe    | 3-S"Pr | Formula (A1-6), $R^{A13}$ = CH$_2$CH(OH)CH$_2$CH$_2$OH |
| 84 | Br | SMe    | 4-S"Bu | Formula (A1-6), $R^{A13}$ = CH$_2$CH(OH)CH$_2$CH$_2$OH |
| 85 | Br | 2-SEt  | 2-SEt  | Formula (A1-6), $R^{A13}$ = CH$_2$CH(OH)CH$_2$CH$_2$OH |
| 86 | Br | 2-SEt  | 3-S"Pr | Formula (A1-6), $R^{A13}$ = CH$_2$CH(OH)CH$_2$CH$_2$OH |
| 87 | Br | 2-SEt  | 4-S"Bu | Formula (A1-6), $R^{A13}$ = CH$_2$CH(OH)CH$_2$CH$_2$OH |
| 88 | Br | 3-S"Pr | 3-S"Pr | Formula (A1-6), $R^{A13}$ = CH$_2$CH(OH)CH$_2$CH$_2$OH |
| 89 | Br | 3-S"Pr | 4-S"Bu | Formula (A1-6), $R^{A13}$ = CH$_2$CH(OH)CH$_2$CH$_2$OH |
| 90 | Br | 4-S"Bu | 4-S"Bu | Formula (A1-6), $R^{A13}$ = CH$_2$CH(OH)CH$_2$CH$_2$OH |

TABLE 24

| No. | Q  | $R^{11}$ | $R^{12}$ | $A^1$ |
|-----|----|----------|----------|-------|
| 91  | Br | SMe    | SMe    | Formula (A1-6), $R^{A13}$ = CH$_2$CH$_2$CH(OH)CH$_2$CH$_2$OH |
| 92  | Br | SMe    | 2-SEt  | Formula (A1-6), $R^{A13}$ = CH$_2$CH$_2$CH(OH)CH$_2$CH$_2$OH |
| 93  | Br | SMe    | 3-S"Pr | Formula (A1-6), $R^{A13}$ = CH$_2$CH$_2$CH(OH)CH$_2$CH$_2$OH |
| 94  | Br | SMe    | 4-S"Bu | Formula (A1-6), $R^{A13}$ = CH$_2$CH$_2$CH(OH)CH$_2$CH$_2$OH |
| 95  | Br | 2-SEt  | 2-SEt  | Formula (A1-6), $R^{A13}$ = CH$_2$CH$_2$CH(OH)CH$_2$CH$_2$OH |
| 96  | Br | 2-SEt  | 3-S"Pr | Formula (A1-6), $R^{A13}$ = CH$_2$CH$_2$CH(OH)CH$_2$CH$_2$OH |
| 97  | Br | 2-SEt  | 4-S"Bu | Formula (A1-6), $R^{A13}$ = CH$_2$CH$_2$CH(OH)CH$_2$CH$_2$OH |
| 98  | Br | 3-S"Pr | 3-S"Pr | Formula (A1-6), $R^{A13}$ = CH$_2$CH$_2$CH(OH)CH$_2$CH$_2$OH |
| 99  | Br | 3-S"Pr | 4-S"Bu | Formula (A1-6), $R^{A13}$ = CH$_2$CH$_2$CH(OH)CH$_2$CH$_2$OH |
| 100 | Br | 4-S"Bu | 4-S"Bu | Formula (A1-6), $R^{A13}$ = CH$_2$CH$_2$CH(OH)CH$_2$CH$_2$OH |
| 101 | F  | SMe    | SMe    | Formula (A1-7) |
| 102 | F  | SMe    | 2-SEt  | Formula (A1-7) |
| 103 | F  | SMe    | 3-S"Pr | Formula (A1-7) |
| 104 | F  | SMe    | 4-S"Bu | Formula (A1-7) |
| 105 | F  | 2-SEt  | 2-SEt  | Formula (A1-7) |
| 106 | F  | 2-SEt  | 3-S"Pr | Formula (A1-7) |
| 107 | F  | 2-SEt  | 4-S"Bu | Formula (A1-7) |
| 108 | F  | 3-S"Pr | 3-S"Pr | Formula (A1-7) |
| 109 | F  | 3-S"Pr | 4-S"Bu | Formula (A1-7) |
| 110 | F  | 4-S"Bu | 4-S"Bu | Formula (A1-7) |
| 111 | F  | SMe    | SMe    | Formula (A1-8) |
| 112 | F  | SMe    | 2-SEt  | Formula (A1-8) |
| 113 | F  | SMe    | 3-S"Pr | Formula (A1-8) |
| 114 | F  | SMe    | 4-S"Bu | Formula (A1-8) |
| 115 | F  | 2-SEt  | 2-SEt  | Formula (A1-8) |
| 116 | F  | 2-SEt  | 3-S"Pr | Formula (A1-8) |
| 117 | F  | 2-SEt  | 4-S"Bu | Formula (A1-8) |
| 118 | F  | 3-S"Pr | 3-S"Pr | Formula (A1-8) |
| 119 | F  | 3-S"Pr | 4-S"Bu | Formula (A1-8) |
| 120 | F  | 4-S"Bu | 4-S"Bu | Formula (A1-8) |

TABLE 25

| No. | Q | $R^{11}$ | $R^{12}$ | $A^1$ |
|---|---|---|---|---|
| 121 | F | SMe | SMe | Formula (A1-6), $RA^{13}$ = CH(OH)CH$_2$(OH) |
| 122 | F | SMe | 2-SEt | Formula (A1-6), $RA^{13}$ = CH(OH)CH$_2$(OH) |
| 123 | F | SMe | 3-S″Pr | Formula (A1-6), $RA^{13}$ = CH(OH)CH$_2$(OH) |
| 124 | F | SMe | 4-S″Bu | Formula (A1-6), $RA^{13}$ = CH(OH)CH$_2$(OH) |
| 125 | F | 2-SEt | 2-SEt | Formula (A1-6), $RA^{13}$ = CH(OH)CH$_2$(OH) |
| 126 | F | 2-SEt | 3-S″Pr | Formula (A1-6), $RA^{13}$ = CH(OH)CH$_2$(OH) |
| 127 | F | 2-SEt | 4-S″Bu | Formula (A1-6), $RA^{13}$ = CH(OH)CH$_2$(OH) |
| 128 | F | 3-S″Pr | 3-S″Pr | Formula (A1-6), $RA^{13}$ = CH(OH)CH$_2$(OH) |
| 129 | F | 3-S″Pr | 4-S″Bu | Formula (A1-6), $RA^{13}$ = CH(OH)CH$_2$(OH) |
| 130 | F | 4-S″Bu | 4-S″Bu | Formula (A1-6), $RA^{13}$ = CH(OH)CH$_2$(OH) |
| 131 | F | SMe | SMe | Formula (A1-6), $RA^{13}$ = CH$_2$CH(OH)CH$_2$CH$_2$OH |
| 132 | F | SMe | 2-SEt | Formula (A1-6), $RA^{13}$ = CH$_2$CH(OH)CH$_2$CH$_2$OH |
| 133 | F | SMe | 3-S″Pr | Formula (A1-6), $RA^{13}$ = CH$_2$CH(OH)CH$_2$CH$_2$OH |
| 134 | F | SMe | 4-S″Bu | Formula (A1-6), $RA^{13}$ = CH$_2$CH(OH)CH$_2$CH$_2$OH |
| 135 | F | 2-SEt | 2-SEt | Formula (A1-6), $RA^{13}$ = CH$_2$CH(OH)CH$_2$CH$_2$OH |
| 136 | F | 2-SEt | 3-S″Pr | Formula (A1-6), $RA^{13}$ = CH$_2$CH(OH)CH$_2$CH$_2$OH |
| 137 | F | 2-SEt | 4-S″Bu | Formula (A1-6), $RA^{13}$ = CH$_2$CH(OH)CH$_2$CH$_2$OH |
| 138 | F | 3-S″Pr | 3-S″Pr | Formula (A1-6), $RA^{13}$ = CH$_2$CH(OH)CH$_2$CH$_2$OH |
| 139 | F | 3-S″Pr | 4-S″Bu | Formula (A1-6), $RA^{13}$ = CH$_2$CH(OH)CH$_2$CH$_2$OH |
| 140 | F | 4-S″Bu | 4-S″Bu | Formula (A1-6), $RA^{13}$ = CH$_2$CH(OH)CH$_2$CH$_2$OH |
| 141 | F | SMe | SMe | Formula (A1-6), $RA^{13}$ = CH$_2$CH$_2$CH(OH)CH$_2$CH$_2$OH |
| 142 | F | SMe | 2-SEt | Formula (A1-6), $RA^{13}$ = CH$_2$CH$_2$CH(OH)CH$_2$CH$_2$OH |
| 143 | F | SMe | 3-S″Pr | Formula (A1-6), $RA^{13}$ = CH$_2$CH$_2$CH(OH)CH$_2$CH$_2$OH |
| 144 | F | SMe | 4-S″Bu | Formula (A1-6), $RA^{13}$ = CH$_2$CH$_2$CH(OH)CH$_2$CH$_2$OH |
| 145 | F | 2-SEt | 2-SEt | Formula (A1-6), $RA^{13}$ = CH$_2$CH$_2$CH(OH)CH$_2$CH$_2$OH |
| 146 | F | 2-SEt | 3-S″Pr | Formula (A1-6), $RA^{13}$ = CH$_2$CH$_2$CH(OH)CH$_2$CH$_2$OH |
| 147 | F | 2-SEt | 4-S″Bu | Formula (A1-6), $RA^{13}$ = CH$_2$CH$_2$CH(OH)CH$_2$CH$_2$OH |
| 148 | F | 3-S″Pr | 3-S″Pr | Formula (A1-6), $RA^{13}$ = CH$_2$CH$_2$CH(OH)CH$_2$CH$_2$OH |
| 149 | F | 3-S″Pr | 4-S″Bu | Formula (A1-6), $RA^{13}$ = CH$_2$CH$_2$CH(OH)CH$_2$CH$_2$OH |
| 150 | F | 4-S″Bu | 4-S″Bu | Formula (A1-6), $RA^{13}$ = CH$_2$CH$_2$CH(OH)CH$_2$CH$_2$OH |

When $A^1$ in the above formula (1) is a C2-C6 alkyl-monosubstituted amino group having two or more hydroxy groups, preferred compounds include, for example, one in which in the above formula (1-1), Q is a chlorine atom, x is 3, and $A^1$ is a group represented by the above formula (A1-7) or (A1-8).

(Group Represented by Formula (A1-3))

In the above formula (A1-3), m represents an integer of 1 to 6, preferably an integer of 2 to 5, and more preferably 2. n represents an integer of 1 to 5, preferably an integer of 1 to 3.

Specific examples of a compound in which $A^1$ in the above formula (1) is a group represented by the above formula (A1-3) are shown in Tables 26 to 31 below. However, the present invention shall not be limited to these specific examples. Abbreviations in Tables 26 to 31 have the following meanings.

SMe: sulfomethyl (*—CH$_2$—SO$_3$H)
2-SEt: 2-sulfoethyl (*—CH$_2$CH$_2$—SO$_3$H)
3-S″Pr: 3-sulfo-n-propyl (*—CH$_2$CH$_2$CH$_2$—SO$_3$H)
4-S″Bu: 3-sulfo-n-butyl (*—CH$_2$CH$_2$CH$_2$CH$_2$—SO$_3$H)

The symbol "*" in the above formulae indicates a position of attachment to the oxygen atom.

TABLE 26

| No. | Q | $R^{11}$ | $R^{12}$ | $A^1$ |
|---|---|---|---|---|
| 1 | Cl | 3-S″Pr | 3-S″Pr | Formula (A1-3), m = 1, n = 1 |
| 2 | Cl | 3-S″Pr | 3-S″Pr | Formula (A1-3), m = 1, n = 2 |
| 3 | Cl | 3-S″Pr | 3-S″Pr | Formula (A1-3), m = 1, n = 3 |
| 4 | Cl | 3-S″Pr | 3-S″Pr | Formula (A1-3), m = 1, n = 4 |
| 5 | Cl | 3-S″Pr | 3-S″Pr | Formula (A1-3), m = 1, n = 5 |
| 6 | Cl | 3-S″Pr | 3-S″Pr | Formula (A1-3), m = 2, n = 1 |
| 7 | Cl | 3-S″Pr | 3-S″Pr | Formula (A1-3), m = 2, n = 2 |
| 8 | Cl | 3-S″Pr | 3-S″Pr | Formula (A1-3), m = 2, n = 3 |
| 9 | Cl | 3-S″Pr | 3-S″Pr | Formula (A1-3), m = 2, n = 4 |
| 10 | Cl | 3-S″Pr | 3-S″Pr | Formula (A1-3), m = 2, n = 5 |
| 11 | Cl | 3-S″Pr | 3-S″Pr | Formula (A1-3), m = 3, n = 1 |

TABLE 26-continued

| No. | Q | $R^{11}$ | $R^{12}$ | $A^1$ |
|---|---|---|---|---|
| 12 | Cl | 3-S″Pr | 3-S″Pr | Formula (A1-3), m = 3, n = 2 |
| 13 | Cl | 3-S″Pr | 3-S″Pr | Formula (A1-3), m = 3, n = 3 |
| 14 | Cl | 3-S″Pr | 3-S″Pr | Formula (A1-3), m = 3, n = 4 |
| 15 | Cl | 3-S″Pr | 3-S″Pr | Formula (A1-3), m = 3, n = 5 |
| 16 | Cl | 3-S″Pr | 3-S″Pr | Formula (A1-3), m = 4, n = 1 |
| 17 | Cl | 3-S″Pr | 3-S″Pr | Formula (A1-3), m = 4, n = 2 |
| 18 | Cl | 3-S″Pr | 3-S″Pr | Formula (A1-3), m = 4, n = 3 |
| 19 | Cl | 3-S″Pr | 3-S″Pr | Formula (A1-3), m = 4, n = 4 |
| 20 | Cl | 3-S″Pr | 3-S″Pr | Formula (A1-3), m = 4, n = 5 |
| 21 | Cl | 3-S″Pr | 3-S″Pr | Formula (A1-3), m = 5, n = 1 |
| 22 | Cl | 3-S″Pr | 3-S″Pr | Formula (A1-3), m = 5, n = 2 |
| 23 | Cl | 3-S″Pr | 3-S″Pr | Formula (A1-3), m = 5, n = 3 |
| 24 | Cl | 3-S″Pr | 3-S″Pr | Formula (A1-3), m = 5, n = 4 |
| 25 | Cl | 3-S″Pr | 3-S″Pr | Formula (A1-3), m = 5, n = 5 |
| 26 | Cl | 3-S″Pr | 3-S″Pr | Formula (A1-3), m = 6, n = 1 |
| 27 | Cl | 3-S″Pr | 3-S″Pr | Formula (A1-3), m = 6, n = 2 |
| 28 | Cl | 3-S″Pr | 3-S″Pr | Formula (A1-3), m = 6, n = 3 |
| 29 | Cl | 3-S″Pr | 3-S″Pr | Formula (A1-3), m = 6, n = 4 |
| 30 | Cl | 3-S″Pr | 3-S″Pr | Formula (A1-3), m = 6, n = 5 |

TABLE 27

| No. | Q | $R^{11}$ | $R^{12}$ | $A^1$ |
|---|---|---|---|---|
| 31 | Cl | SMe | SMe | Formula (A1-3), m = 2, n = 1 |
| 32 | Cl | SMe | SMe | Formula (A1-3), m = 2, n = 2 |
| 33 | Cl | SMe | SMe | Formula (A1-3), m = 2, n = 3 |
| 34 | Cl | SMe | 2-SEt | Formula (A1-3), m = 2, n = 1 |
| 35 | Cl | SMe | 2-SEt | Formula (A1-3), m = 2, n = 2 |
| 36 | Cl | SMe | 2-SEt | Formula (A1-3), m = 2, n = 3 |
| 37 | Cl | SMe | 3-S″Pr | Formula (A1-3), m = 2, n = 1 |
| 38 | Cl | SMe | 3-S″Pr | Formula (A1-3), m = 2, n = 2 |
| 39 | Cl | SMe | 3-S″Pr | Formula (A1-3), m = 2, n = 3 |
| 40 | Cl | SMe | 4-S″Bu | Formula (A1-3), m = 2, n = 1 |

TABLE 27-continued

| No. | Q | $R^{11}$ | $R^{12}$ | $A^1$ |
|---|---|---|---|---|
| 41 | Cl | SMe | 4-S"Bu | Formula (A1-3), m = 2, n = 2 |
| 42 | Cl | SMe | 4-S"Bu | Formula (A1-3), m = 2, n = 3 |
| 43 | Cl | 2-SEt | 2-SEt | Formula (A1-3), m = 2, n = 1 |
| 44 | Cl | 2-SEt | 2-SEt | Formula (A1-3), m = 2, n = 2 |
| 45 | Cl | 2-SEt | 2-SEt | Formula (A1-3), m = 2, n = 3 |
| 46 | Cl | 2-SEt | 3-S"Pr | Formula (A1-3), m = 2, n = 1 |
| 47 | Cl | 2-SEt | 3-S"Pr | Formula (A1-3), m = 2, n = 2 |
| 48 | Cl | 2-SEt | 3-S"Pr | Formula (A1-3), m = 2, n = 3 |
| 49 | Cl | 2-SEt | 4-S"Bu | Formula (A1-3), m = 2, n = 1 |
| 50 | Cl | 2-SEt | 4-S"Bu | Formula (A1-3), m = 2, n = 2 |
| 51 | Cl | 2-SEt | 4-S"Bu | Formula (A1-3), m = 2, n = 3 |
| 52 | Cl | 3-S"Pr | 4-S"Bu | Formula (A1-3), m = 2, n = 1 |
| 53 | Cl | 3-S"Pr | 4-S"Bu | Formula (A1-3), m = 2, n = 2 |
| 54 | Cl | 3-S"Pr | 4-S"Bu | Formula (A1-3), m = 2, n = 3 |
| 55 | Cl | 4-S"Bu | 4-S"Bu | Formula (A1-3), m = 2, n = 1 |
| 56 | Cl | 4-S"Bu | 4-S"Bu | Formula (A1-3), m = 2, n = 2 |
| 57 | Cl | 4-S"Bu | 4-S"Bu | Formula (A1-3), m = 2, n = 3 |
| 58 | Br | 3-S"Pr | 3-S"Pr | Formula (A1-3), m = 1, n = 1 |
| 59 | Br | 3-S"Pr | 3-S"Pr | Formula (A1-3), m = 1, n = 2 |
| 60 | Br | 3-S"Pr | 3-S"Pr | Formula (A1-3), m = 1, n = 3 |

TABLE 28

| No. | Q | $R^{11}$ | $R^{12}$ | $A^1$ |
|---|---|---|---|---|
| 61 | Br | 3-S"Pr | 3-S"Pr | Formula (A1-3), m = 1, n = 4 |
| 62 | Br | 3-S"Pr | 3-S"Pr | Formula (A1-3), m = 1, n = 5 |
| 63 | Br | 3-S"Pr | 3-S"Pr | Formula (A1-3), m = 2, n = 1 |
| 64 | Br | 3-S"Pr | 3-S"Pr | Formula (A1-3), m = 2, n = 2 |
| 65 | Br | 3-S"Pr | 3-S"Pr | Formula (A1-3), m = 2, n = 3 |
| 66 | Br | 3-S"Pr | 3-S"Pr | Formula (A1-3), m = 2, n = 4 |
| 67 | Br | 3-S"Pr | 3-S"Pr | Formula (A1-3), m = 2, n = 5 |
| 68 | Br | 3-S"Pr | 3-S"Pr | Formula (A1-3), m = 3, n = 1 |
| 69 | Br | 3-S"Pr | 3-S"Pr | Formula (A1-3), m = 3, n = 2 |
| 70 | Br | 3-S"Pr | 3-S"Pr | Formula (A1-3), m = 3, n = 3 |
| 71 | Br | 3-S"Pr | 3-S"Pr | Formula (A1-3), m = 3, n = 4 |
| 72 | Br | 3-S"Pr | 3-S"Pr | Formula (A1-3), m = 3, n = 5 |
| 73 | Br | 3-S"Pr | 3-S"Pr | Formula (A1-3), m = 4, n = 1 |
| 74 | Br | 3-S"Pr | 3-S"Pr | Formula (A1-3), m = 4, n = 2 |
| 75 | Br | 3-S"Pr | 3-S"Pr | Formula (A1-3), m = 4, n = 3 |
| 76 | Br | 3-S"Pr | 3-S"Pr | Formula (A1-3), m = 4, n = 4 |
| 77 | Br | 3-S"Pr | 3-S"Pr | Formula (A1-3), m = 4, n = 5 |
| 78 | Br | 3-S"Pr | 3-S"Pr | Formula (A1-3), m = 5, n = 1 |
| 79 | Br | 3-S"Pr | 3-S"Pr | Formula (A1-3), m = 5, n = 2 |
| 80 | Br | 3-S"Pr | 3-S"Pr | Formula (A1-3), m = 5, n = 3 |
| 81 | Br | 3-S"Pr | 3-S"Pr | Formula (A1-3), m = 5, n = 4 |
| 82 | Br | 3-S"Pr | 3-S"Pr | Formula (A1-3), m = 5, n = 5 |
| 83 | Br | 3-S"Pr | 3-S"Pr | Formula (A1-3), m = 6, n = 1 |
| 84 | Br | 3-S"Pr | 3-S"Pr | Formula (A1-3), m = 6, n = 2 |
| 85 | Br | 3-S"Pr | 3-S"Pr | Formula (A1-3), m = 6, n = 3 |
| 86 | Br | 3-S"Pr | 3-S"Pr | Formula (A1-3), m = 6, n = 4 |
| 87 | Br | 3-S"Pr | 3-S"Pr | Formula (A1-3), m = 6, n = 5 |
| 88 | Br | SMe | SMe | Formula (A1-3), m = 2, n = 1 |
| 89 | Br | SMe | SMe | Formula (A1-3), m = 2, n = 2 |
| 90 | Br | SMe | SMe | Formula (A1-3), m = 2, n = 3 |

TABLE 29

| No. | Q | $R^{11}$ | $R^{12}$ | $A^1$ |
|---|---|---|---|---|
| 91 | Br | SMe | 2-SEt | Formula (A1-3), m = 2, n = 1 |
| 92 | Br | SMe | 2-SEt | Formula (A1-3), m = 2, n = 2 |
| 93 | Br | SMe | 2-SEt | Formula (A1-3), m = 2, n = 3 |
| 94 | Br | SMe | 3-S"Pr | Formula (A1-3), m = 2, n = 1 |
| 95 | Br | SMe | 3-S"Pr | Formula (A1-3), m = 2, n = 2 |
| 96 | Br | SMe | 3-S"Pr | Formula (A1-3), m = 2, n = 3 |
| 97 | Br | SMe | 4-S"Bu | Formula (A1-3), m = 2, n = 1 |
| 98 | Br | SMe | 4-S"Bu | Formula (A1-3), m = 2, n = 2 |
| 99 | Br | SMe | 4-S"Bu | Formula (A1-3), m = 2, n = 3 |
| 100 | Br | 2-SEt | 2-SEt | Formula (A1-3), m = 2, n = 1 |
| 101 | Br | 2-SEt | 2-SEt | Formula (A1-3), m = 2, n = 2 |
| 102 | Br | 2-SEt | 2-SEt | Formula (A1-3), m = 2, n = 3 |
| 103 | Br | 2-SEt | 3-S"Pr | Formula (A1-3), m = 2, n = 1 |

TABLE 29-continued

| No. | Q | $R^{11}$ | $R^{12}$ | $A^1$ |
|---|---|---|---|---|
| 104 | Br | 2-SEt | 3-S"Pr | Formula (A1-3), m = 2, n = 2 |
| 105 | Br | 2-SEt | 3-S"Pr | Formula (A1-3), m = 2, n = 3 |
| 106 | Br | 2-SEt | 4-S"Bu | Formula (A1-3), m = 2, n = 1 |
| 107 | Br | 2-SEt | 4-S"Bu | Formula (A1-3), m = 2, n = 2 |
| 108 | Br | 2-SEt | 4-S"Bu | Formula (A1-3), m = 2, n = 3 |
| 109 | Br | 3-S"Pr | 4-S"Bu | Formula (A1-3), m = 2, n = 1 |
| 110 | Br | 3-S"Pr | 4-S"Bu | Formula (A1-3), m = 2, n = 2 |
| 111 | Br | 3-S"Pr | 4-S"Bu | Formula (A1-3), m = 2, n = 3 |
| 112 | Br | 4-S"Bu | 4-S"Bu | Formula (A1-3), m = 2, n = 1 |
| 113 | Br | 4-S"Bu | 4-S"Bu | Formula (A1-3), m = 2, n = 2 |
| 114 | Br | 4-S"Bu | 4-S"Bu | Formula (A1-3), m = 2, n = 3 |
| 115 | F | 3-S"Pr | 3-S"Pr | Formula (A1-3), m = 1, n = 1 |
| 116 | F | 3-S"Pr | 3-S"Pr | Formula (A1-3), m = 1, n = 2 |
| 117 | F | 3-S"Pr | 3-S"Pr | Formula (A1-3), m = 1, n = 3 |
| 118 | F | 3-S"Pr | 3-S"Pr | Formula (A1-3), m = 1, n = 4 |
| 119 | F | 3-S"Pr | 3-S"Pr | Formula (A1-3), m = 1, n = 5 |
| 120 | F | 3-S"Pr | 3-S"Pr | Formula (A1-3), m = 2, n = 1 |

TABLE 30

| No. | Q | $R^{11}$ | $R^{12}$ | $A^1$ |
|---|---|---|---|---|
| 121 | F | 3-S"Pr | 3-S"Pr | Formula (A1-3), m = 2, n = 2 |
| 122 | F | 3-S"Pr | 3-S"Pr | Formula (A1-3), m = 2, n = 3 |
| 123 | F | 3-S"Pr | 3-S"Pr | Formula (A1-3), m = 2, n = 4 |
| 124 | F | 3-S"Pr | 3-S"Pr | Formula (A1-3), m = 2, n = 5 |
| 125 | F | 3-S"Pr | 3-S"Pr | Formula (A1-3), m = 3, n = 1 |
| 126 | F | 3-S"Pr | 3-S"Pr | Formula (A1-3), m = 3, n = 2 |
| 127 | F | 3-S"Pr | 3-S"Pr | Formula (A1-3), m = 3, n = 3 |
| 128 | F | 3-S"Pr | 3-S"Pr | Formula (A1-3), m = 3, n = 4 |
| 129 | F | 3-S"Pr | 3-S"Pr | Formula (A1-3), m = 3, n = 5 |
| 130 | F | 3-S"Pr | 3-S"Pr | Formula (A1-3), m = 4, n = 1 |
| 131 | F | 3-S"Pr | 3-S"Pr | Formula (A1-3), m = 4, n = 2 |
| 132 | F | 3-S"Pr | 3-S"Pr | Formula (A1-3), m = 4, n = 3 |
| 133 | F | 3-S"Pr | 3-S"Pr | Formula (A1-3), m = 4, n = 4 |
| 134 | F | 3-S"Pr | 3-S"Pr | Formula (A1-3), m = 4, n = 5 |
| 135 | F | 3-S"Pr | 3-S"Pr | Formula (A1-3), m = 5, n = 1 |
| 136 | F | 3-S"Pr | 3-S"Pr | Formula (A1-3), m = 5, n = 2 |
| 137 | F | 3-S"Pr | 3-S"Pr | Formula (A1-3), m = 5, n = 3 |
| 138 | F | 3-S"Pr | 3-S"Pr | Formula (A1-3), m = 5, n = 4 |
| 139 | F | 3-S"Pr | 3-S"Pr | Formula (A1-3), m = 5, n = 5 |
| 140 | F | 3-S"Pr | 3-S"Pr | Formula (A1-3), m = 6, n = 1 |
| 141 | F | 3-S"Pr | 3-S"Pr | Formula (A1-3), m = 6, n = 2 |
| 142 | F | 3-S"Pr | 3-S"Pr | Formula (A1-3), m = 6, n = 3 |
| 143 | F | 3-S"Pr | 3-S"Pr | Formula (A1-3), m = 6, n = 4 |
| 144 | F | 3-S"Pr | 3-S"Pr | Formula (A1-3), m = 6, n = 5 |
| 145 | F | SMe | SMe | Formula (A1-3), m = 2, n = 1 |
| 146 | F | SMe | SMe | Formula (A1-3), m = 2, n = 2 |
| 147 | F | SMe | SMe | Formula (A1-3), m = 2, n = 3 |
| 148 | F | SMe | 2-SEt | Formula (A1-3), m = 2, n = 1 |
| 149 | F | SMe | 2-SEt | Formula (A1-3), m = 2, n = 2 |
| 150 | F | SMe | 2-SEt | Formula (A1-3), m = 2, n = 3 |

TABLE 31

| No. | Q | $R^{11}$ | $R^{12}$ | $A^1$ |
|---|---|---|---|---|
| 151 | F | SMe | 3-S"Pr | Formula (A1-3), m = 2, n = 1 |
| 152 | F | SMe | 3-S"Pr | Formula (A1-3), m = 2, n = 2 |
| 153 | F | SMe | 3-S"Pr | Formula (A1-3), m = 2, n = 3 |
| 154 | F | SMe | 4-S"Bu | Formula (A1-3), m = 2, n = 1 |
| 155 | F | SMe | 4-S"Bu | Formula (A1-3), m = 2, n = 2 |
| 156 | F | SMe | 4-S"Bu | Formula (A1-3), m = 2, n = 3 |
| 157 | F | 2-SEt | 2-SEt | Formula (A1-3), m = 2, n = 1 |
| 158 | F | 2-SEt | 2-SEt | Formula (A1-3), m = 2, n = 2 |
| 159 | F | 2-SEt | 2-SEt | Formula (A1-3), m = 2, n = 3 |
| 160 | F | 2-SEt | 3-S"Pr | Formula (A1-3), m = 2, n = 1 |
| 161 | F | 2-SEt | 3-S"Pr | Formula (A1-3), m = 2, n = 2 |
| 162 | F | 2-SEt | 3-S"Pr | Formula (A1-3), m = 2, n = 3 |
| 163 | F | 2-SEt | 4-S"Bu | Formula (A1-3), m = 2, n = 1 |
| 164 | F | 2-SEt | 4-S"Bu | Formula (A1-3), m = 2, n = 2 |
| 165 | F | 2-SEt | 4-S"Bu | Formula (A1-3), m = 2, n = 3 |
| 166 | F | 3-S"Pr | 4-S"Bu | Formula (A1-3), m = 2, n = 1 |

TABLE 31-continued

| No. | Q | $R^{11}$ | $R^{12}$ | $A^1$ |
|---|---|---|---|---|
| 167 | F | 3-S″Pr | 4-S″Bu | Formula (A1-3), m = 2, n = 2 |
| 168 | F | 3-S″Pr | 4-S″Bu | Formula (A1-3), m = 2, n = 3 |
| 169 | F | 4-S″Bu | 4-S″Bu | Formula (A1-3), m = 2, n = 1 |
| 170 | F | 4-S″Bu | 4-S″Bu | Formula (A1-3), m = 2, n = 2 |
| 171 | F | 4-S″Bu | 4-S″Bu | Formula (A1-3), m = 2, n = 3 |

When $A^1$ in the above formula (1) is a group represented by the above formula (A1-3), preferred compounds include, for example, one represented by the above formula (1-17) or (1-18).
(Group Represented by Formula (A1-4))

In the above formula (A1-4), n represents an integer of 2 to 6, preferably 3.

Specific examples of a compound in which $A^1$ in the above formula (1) is a group represented by the above formula (A1-4) are shown in Tables 32 to 37 below. However, the present invention shall not be limited to these specific examples. Abbreviations in Tables 32 to 37 have the following meanings.

SMe: sulfomethyl (*—CH$_2$—SO$_3$H)
2-SEt: 2-sulfoethyl (*—CH$_2$CH$_2$—SO$_3$H)
3-S″Pr: 3-sulfo-n-propyl (*—CH$_2$CH$_2$CH$_2$—SO$_3$H)
4-S″Bu: 3-sulfo-n-butyl (*—CH$_2$CH$_2$CH$_2$CH$_2$—SO$_3$H)

The symbol "*" in the above formulae indicates a position of attachment to the oxygen atom.

TABLE 32

| No. | Q | $R^{11}$ | $R^{12}$ | $A^1$ |
|---|---|---|---|---|
| 1 | Cl | SMe | SMe | Formula (A1-4), n = 1 |
| 2 | Cl | SMe | 2-SEt | Formula (A1-4), n = 1 |
| 3 | Cl | SMe | 3-S″Pr | Formula (A1-4), n = 1 |
| 4 | Cl | SMe | 4-S″Bu | Formula (A1-4), n = 1 |
| 5 | Cl | 2-SEt | 2-SEt | Formula (A1-4), n = 1 |
| 6 | Cl | 2-SEt | 3-S″Pr | Formula (A1-4), n = 1 |
| 7 | Cl | 2-SEt | 4-S″Bu | Formula (A1-4), n = 1 |
| 8 | Cl | 3-S″Pr | 3-S″Pr | Formula (A1-4), n = 1 |
| 9 | Cl | 3-S″Pr | 4-S″Bu | Formula (A1-4), n = 1 |
| 10 | Cl | 4-S″Bu | 4-S″Bu | Formula (A1-4), n = 1 |
| 11 | Cl | SMe | SMe | Formula (A1-4), n = 2 |
| 12 | Cl | SMe | 2-SEt | Formula (A1-4), n = 2 |
| 13 | Cl | SMe | 3-S″Pr | Formula (A1-4), n = 2 |
| 14 | Cl | SMe | 4-S″Bu | Formula (A1-4), n = 2 |
| 15 | Cl | 2-SEt | 2-SEt | Formula (A1-4), n = 2 |
| 16 | Cl | 2-SEt | 3-S″Pr | Formula (A1-4), n = 2 |
| 17 | Cl | 2-SEt | 4-S″Bu | Formula (A1-4), n = 2 |
| 18 | Cl | 3-S″Pr | 3-S″Pr | Formula (A1-4), n = 2 |
| 19 | Cl | 3-S″Pr | 4-S″Bu | Formula (A1-4), n = 2 |
| 20 | Cl | 4-S″Bu | 4-S″Bu | Formula (A1-4), n = 2 |
| 21 | Cl | SMe | SMe | Formula (A1-4), n = 3 |
| 22 | Cl | SMe | 2-SEt | Formula (A1-4), n = 3 |
| 23 | Cl | SMe | 3-S″Pr | Formula (A1-4), n = 3 |
| 24 | Cl | SMe | 4-S″Bu | Formula (A1-4), n = 3 |
| 25 | Cl | 2-SEt | 2-SEt | Formula (A1-4), n = 3 |
| 26 | Cl | 2-SEt | 3-S″Pr | Formula (A1-4), n = 3 |
| 27 | Cl | 2-SEt | 4-S″Bu | Formula (A1-4), n = 3 |
| 28 | Cl | 3-S″Pr | 3-S″Pr | Formula (A1-4), n = 3 |
| 29 | Cl | 3-S″Pr | 4-S″Bu | Formula (A1-4), n = 3 |
| 30 | Cl | 4-S″Bu | 4-S″Bu | Formula (A1-4), n = 3 |

TABLE 33

| No. | Q | $R^{11}$ | $R^{12}$ | $A^1$ |
|---|---|---|---|---|
| 31 | Cl | SMe | SMe | Formula (A1-4), n = 4 |
| 32 | Cl | SMe | 2-SEt | Formula (A1-4), n = 4 |
| 33 | Cl | SMe | 3-S″Pr | Formula (A1-4), n = 4 |
| 34 | Cl | SMe | 4-S″Bu | Formula (A1-4), n = 4 |

TABLE 33-continued

| No. | Q | $R^{11}$ | $R^{12}$ | $A^1$ |
|---|---|---|---|---|
| 35 | Cl | 2-SEt | 2-SEt | Formula (A1-4), n = 4 |
| 36 | Cl | 2-SEt | 3-S″Pr | Formula (A1-4), n = 4 |
| 37 | Cl | 2-SEt | 4-S″Bu | Formula (A1-4), n = 4 |
| 38 | Cl | 3-S″Pr | 3-S″Pr | Formula (A1-4), n = 4 |
| 39 | Cl | 3-S″Pr | 4-S″Bu | Formula (A1-4), n = 4 |
| 40 | Cl | 4-S″Bu | 4-S″Bu | Formula (A1-4), n = 4 |
| 41 | Cl | SMe | SMe | Formula (A1-4), n = 5 |
| 42 | Cl | SMe | 2-SEt | Formula (A1-4), n = 5 |
| 43 | Cl | SMe | 3-S″Pr | Formula (A1-4), n = 5 |
| 44 | Cl | SMe | 4-S″Bu | Formula (A1-4), n = 5 |
| 45 | Cl | 2-SEt | 2-SEt | Formula (A1-4), n = 5 |
| 46 | Cl | 2-SEt | 3-S″Pr | Formula (A1-4), n = 5 |
| 47 | Cl | 2-SEt | 4-S″Bu | Formula (A1-4), n = 5 |
| 48 | Cl | 3-S″Pr | 3-S″Pr | Formula (A1-4), n = 5 |
| 49 | Cl | 3-S″Pr | 4-S″Bu | Formula (A1-4), n = 5 |
| 50 | Cl | 4-S″Bu | 4-S″Bu | Formula (A1-4), n = 5 |
| 51 | Cl | SMe | SMe | Formula (A1-4), n = 6 |
| 52 | Cl | SMe | 2-SEt | Formula (A1-4), n = 6 |
| 53 | Cl | SMe | 3-S″Pr | Formula (A1-4), n = 6 |
| 54 | Cl | SMe | 4-S″Bu | Formula (A1-4), n = 6 |
| 55 | Cl | 2-SEt | 2-SEt | Formula (A1-4), n = 6 |
| 56 | Cl | 2-SEt | 3-S″Pr | Formula (A1-4), n = 6 |
| 57 | Cl | 2-SEt | 4-S″Bu | Formula (A1-4), n = 6 |
| 58 | Cl | 3-S″Pr | 3-S″Pr | Formula (A1-4), n = 6 |
| 59 | Cl | 3-S″Pr | 4-S″Bu | Formula (A1-4), n = 6 |
| 60 | Cl | 4-S″Bu | 4-S″Bu | Formula (A1-4), n = 6 |

TABLE 34

| No. | Q | $R^{11}$ | $R^{12}$ | $A^1$ |
|---|---|---|---|---|
| 61 | Br | SMe | SMe | Formula (A1-4), n = 1 |
| 62 | Br | SMe | 2-SEt | Formula (A1-4), n = 1 |
| 63 | Br | SMe | 3-S″Pr | Formula (A1-4), n = 1 |
| 64 | Br | SMe | 4-S″Bu | Formula (A1-4), n = 1 |
| 65 | Br | 2-SEt | 2-SEt | Formula (A1-4), n = 1 |
| 66 | Br | 2-SEt | 3-S″Pr | Formula (A1-4), n = 1 |
| 67 | Br | 2-SEt | 4-S″Bu | Formula (A1-4), n = 1 |
| 68 | Br | 3-S″Pr | 3-S″Pr | Formula (A1-4), n = 1 |
| 69 | Br | 3-S″Pr | 4-S″Bu | Formula (A1-4), n = 1 |
| 70 | Br | 4-S″Bu | 4-S″Bu | Formula (A1-4), n = 1 |
| 71 | Br | SMe | SMe | Formula (A1-4), n = 2 |
| 72 | Br | SMe | 2-SEt | Formula (A1-4), n = 2 |
| 73 | Br | SMe | 3-S″Pr | Formula (A1-4), n = 2 |
| 74 | Br | SMe | 4-S″Bu | Formula (A1-4), n = 2 |
| 75 | Br | 2-SEt | 2-SEt | Formula (A1-4), n = 2 |
| 76 | Br | 2-SEt | 3-S″Pr | Formula (A1-4), n = 2 |
| 77 | Br | 2-SEt | 4-S″Bu | Formula (A1-4), n = 2 |
| 78 | Br | 3-S″Pr | 3-S″Pr | Formula (A1-4), n = 2 |
| 79 | Br | 3-S″Pr | 4-S″Bu | Formula (A1-4), n = 2 |
| 80 | Br | 4-S″Bu | 4-S″Bu | Formula (A1-4), n = 2 |
| 81 | Br | SMe | SMe | Formula (A1-4), n = 3 |
| 82 | Br | SMe | 2-SEt | Formula (A1-4), n = 3 |
| 83 | Br | SMe | 3-S″Pr | Formula (A1-4), n = 3 |
| 84 | Br | SMe | 4-S″Bu | Formula (A1-4), n = 3 |
| 85 | Br | 2-SEt | 2-SEt | Formula (A1-4), n = 3 |
| 86 | Br | 2-SEt | 3-S″Pr | Formula (A1-4), n = 3 |
| 87 | Br | 2-SEt | 4-S″Bu | Formula (A1-4), n = 3 |
| 88 | Br | 3-S″Pr | 3-S″Pr | Formula (A1-4), n = 3 |
| 89 | Br | 3-S″Pr | 4-S″Bu | Formula (A1-4), n = 3 |
| 90 | Br | 4-S″Bu | 4-S″Bu | Formula (A1-4), n = 3 |

TABLE 35

| No. | Q | $R^{11}$ | $R^{12}$ | $A^1$ |
|---|---|---|---|---|
| 91 | Br | SMe | SMe | Formula (A1-4), n = 4 |
| 92 | Br | SMe | 2-SEt | Formula (A1-4), n = 4 |
| 93 | Br | SMe | 3-S″Pr | Formula (A1-4), n = 4 |
| 94 | Br | SMe | 4-S″Bu | Formula (A1-4), n = 4 |
| 95 | Br | 2-SEt | 2-SEt | Formula (A1-4), n = 4 |
| 96 | Br | 2-SEt | 3-S″Pr | Formula (A1-4), n = 4 |
| 97 | Br | 2-SEt | 4-S″Bu | Formula (A1-4), n = 4 |

TABLE 35-continued

| No. | Q | $R^{11}$ | $R^{12}$ | $A^1$ |
|---|---|---|---|---|
| 98 | Br | 3-S″Pr | 3-S″Pr | Formula (A1-4), n = 4 |
| 99 | Br | 3-S″Pr | 4-S″Bu | Formula (A1-4), n = 4 |
| 100 | Br | 4-S″Bu | 4-S″Bu | Formula (A1-4), n = 4 |
| 101 | Br | SMe | SMe | Formula (A1-4), n = 5 |
| 102 | Br | SMe | 2-SEt | Formula (A1-4), n = 5 |
| 103 | Br | SMe | 3-S″Pr | Formula (A1-4), n = 5 |
| 104 | Br | SMe | 4-S″Bu | Formula (A1-4), n = 5 |
| 105 | Br | 2-SEt | 2-SEt | Formula (A1-4), n = 5 |
| 106 | Br | 2-SEt | 3-S″Pr | Formula (A1-4), n = 5 |
| 107 | Br | 2-SEt | 4-S″Bu | Formula (A1-4), n = 5 |
| 108 | Br | 3-S″Pr | 3-S″Pr | Formula (A1-4), n = 5 |
| 109 | Br | 3-S″Pr | 4-S″Bu | Formula (A1-4), n = 5 |
| 110 | Br | 4-S″Bu | 4-S″Bu | Formula (A1-4), n = 5 |
| 111 | Br | SMe | SMe | Formula (A1-4), n = 6 |
| 112 | Br | SMe | 2-SEt | Formula (A1-4), n = 6 |
| 113 | Br | SMe | 3-S″Pr | Formula (A1-4), n = 6 |
| 114 | Br | SMe | 4-S″Bu | Formula (A1-4), n = 6 |
| 115 | Br | 2-SEt | 2-SEt | Formula (A1-4), n = 6 |
| 116 | Br | 2-SEt | 3-S″Pr | Formula (A1-4), n = 6 |
| 117 | Br | 2-SEt | 4-S″Bu | Formula (A1-4), n = 6 |
| 118 | Br | 3-S″Pr | 3-S″Pr | Formula (A1-4), n = 6 |
| 119 | Br | 3-S″Pr | 4-S″Bu | Formula (A1-4), n = 6 |
| 120 | Br | 4-S″Bu | 4-S″Bu | Formula (A1-4), n = 6 |

TABLE 36

| No. | Q | $R^{11}$ | $R^{12}$ | $A^1$ |
|---|---|---|---|---|
| 121 | F | SMe | SMe | Formula (A1-4), n = 1 |
| 122 | F | SMe | 2-SEt | Formula (A1-4), n = 1 |
| 123 | F | SMe | 3-S″Pr | Formula (A1-4), n = 1 |
| 124 | F | SMe | 4-S″Bu | Formula (A1-4), n = 1 |
| 125 | F | 2-SEt | 2-SEt | Formula (A1-4), n = 1 |
| 126 | F | 2-SEt | 3-S″Pr | Formula (A1-4), n = 1 |
| 127 | F | 2-SEt | 4-S″Bu | Formula (A1-4), n = 1 |
| 128 | F | 3-S″Pr | 3-S″Pr | Formula (A1-4), n = 1 |
| 129 | F | 3-S″Pr | 4-S″Bu | Formula (A1-4), n = 1 |
| 130 | F | 4-S″Bu | 4-S″Bu | Formula (A1-4), n = 1 |
| 131 | F | SMe | SMe | Formula (A1-4), n = 2 |
| 132 | F | SMe | 2-SEt | Formula (A1-4), n = 2 |
| 133 | F | SMe | 3-S″Pr | Formula (A1-4), n = 2 |
| 134 | F | SMe | 4-S″Bu | Formula (A1-4), n = 2 |
| 135 | F | 2-SEt | 2-SEt | Formula (A1-4), n = 2 |
| 136 | F | 2-SEt | 3-S″Pr | Formula (A1-4), n = 2 |
| 137 | F | 2-SEt | 4-S″Bu | Formula (A1-4), n = 2 |
| 138 | F | 3-S″Pr | 3-S″Pr | Formula (A1-4), n = 2 |
| 139 | F | 3-S″Pr | 4-S″Bu | Formula (A1-4), n = 2 |
| 140 | F | 4-S″Bu | 4-S″Bu | Formula (A1-4), n = 2 |
| 141 | F | SMe | SMe | Formula (A1-4), n = 3 |
| 142 | F | SMe | 2-SEt | Formula (A1-4), n = 3 |
| 143 | F | SMe | 3-S″Pr | Formula (A1-4), n = 3 |
| 144 | F | SMe | 4-S″Bu | Formula (A1-4), n = 3 |
| 145 | F | 2-SEt | 2-SEt | Formula (A1-4), n = 3 |
| 146 | F | 2-SEt | 3-S″Pr | Formula (A1-4), n = 3 |
| 147 | F | 2-SEt | 4-S″Bu | Formula (A1-4), n = 3 |
| 148 | F | 3-S″Pr | 3-S″Pr | Formula (A1-4), n = 3 |
| 149 | F | 3-S″Pr | 4-S″Bu | Formula (A1-4), n = 3 |
| 150 | F | 4-S″Bu | 4-S″Bu | Formula (A1-4), n = 3 |

TABLE 37

| No. | Q | $R^{11}$ | $R^{12}$ | $A^1$ |
|---|---|---|---|---|
| 151 | F | SMe | SMe | Formula (A1-4), n = 4 |
| 152 | F | SMe | 2-SEt | Formula (A1-4), n = 4 |
| 153 | F | SMe | 3-S″Pr | Formula (A1-4), n = 4 |
| 154 | F | SMe | 4-S″Bu | Formula (A1-4), n = 4 |
| 155 | F | 2-SEt | 2-SEt | Formula (A1-4), n = 4 |
| 156 | F | 2-SEt | 3-S″Pr | Formula (A1-4), n = 4 |
| 157 | F | 2-SEt | 4-S″Bu | Formula (A1-4), n = 4 |
| 158 | F | 3-S″Pr | 3-S″Pr | Formula (A1-4), n = 4 |
| 159 | F | 3-S″Pr | 4-S″Bu | Formula (A1-4), n = 4 |
| 160 | F | 4-S″Bu | 4-S″Bu | Formula (A1-4), n = 4 |

TABLE 37-continued

| No. | Q | $R^{11}$ | $R^{12}$ | $A^1$ |
|---|---|---|---|---|
| 161 | F | SMe | SMe | Formula (A1-4), n = 5 |
| 162 | F | SMe | 2-SEt | Formula (A1-4), n = 5 |
| 163 | F | SMe | 3-S″Pr | Formula (A1-4), n = 5 |
| 164 | F | SMe | 4-S″Bu | Formula (A1-4), n = 5 |
| 165 | F | 2-SEt | 2-SEt | Formula (A1-4), n = 5 |
| 166 | F | 2-SEt | 3-S″Pr | Formula (A1-4), n = 5 |
| 167 | F | 2-SEt | 4-S″Bu | Formula (A1-4), n = 5 |
| 168 | F | 3-S″Pr | 3-S″Pr | Formula (A1-4), n = 5 |
| 169 | F | 3-S″Pr | 4-S″Bu | Formula (A1-4), n = 5 |
| 170 | F | 4-S″Bu | 4-S″Bu | Formula (A1-4), n = 5 |
| 171 | F | SMe | SMe | Formula (A1-4), n = 6 |
| 172 | F | SMe | 2-SEt | Formula (A1-4), n = 6 |
| 173 | F | SMe | 3-S″Pr | Formula (A1-4), n = 6 |
| 174 | F | SMe | 4-S″Bu | Formula (A1-4), n = 6 |
| 175 | F | 2-SEt | 2-SEt | Formula (A1-4), n = 6 |
| 176 | F | 2-SEt | 3-S″Pr | Formula (A1-4), n = 6 |
| 177 | F | 2-SEt | 4-S″Bu | Formula (A1-4), n = 6 |
| 178 | F | 3-S″Pr | 3-S″Pr | Formula (A1-4), n = 6 |
| 179 | F | 3-S″Pr | 4-S″Bu | Formula (A1-4), n = 6 |
| 180 | F | 4-S″Bu | 4-S″Bu | Formula (A1-4), n = 6 |

When $A^1$ in the above formula (1) is a group represented by an above formula (A1-4), preferred compounds include, for example, one in which in the above formula (1-1), Q is a chlorine atom, x is 3, and $A^1$ is represented by the above formula (A1-4) wherein n is 3.

(Cyclic Amine Group)

As a cyclic amine group, preferred is a 3- to 5-membered ring group having one nitrogen atom as a ring atom. More preferred is a 5-membered ring group having one nitrogen atom. Examples of the 3- to 5-membered ring having one nitrogen atom include an aziridine ring, an azetidine ring, a pyrrolidine ring and the like. Among cyclic amine groups, preferred is one represented by the above formula (A1-9).

In the above formula (A1-9), each $R^{414}$ to $R^{421}$ independently represents a hydrogen atom or a substituent. There is no particular limitation for the substituent, but examples include a hydroxy group, a substituted or unsubstituted C1-C4 alkyl group, a halogen atom, a sulfo group, a carboxy group, a phospho group, a substituted or unsubstituted amino group, a nitro group, a cyano group, an alkoxy group, a phenyl group, a naphthyl group and the like.

C1-C4 alkyl groups include, for example, a methyl group, an ethyl group, an n-propyl group, an isopropyl group, an n-butyl group, an s-butyl group, a t-butyl group and the like. There is no particular limitation for a substituent that may be present in a C1-C4 alkyl group, but examples include a halogen atom, a sulfo group, a carboxy group, a phospho group, a substituted or unsubstituted amino group, a nitro group, a cyano group, an alkoxy group, a phenyl group, a naphthyl group and the like.

Halogen atoms include a fluorine atom, a chlorine atom, a bromine atom, and an iodine atom.

Substituted amino groups include, for example, a mono-(C1-C4 alkyl)amino group, a dimethylamino group, an ethylmethylamino group and the like.

Alkoxy groups include, for example, C1-C4 alkoxy groups such as a methoxy group, an ethoxy group, and a propoxy group.

In the above formula (A1-9), each $R^{414}$ to $R^{421}$ is preferably a hydrogen atom.

Specific examples of a compound in which $A^1$ in the above formula (1) is a cyclic amine group are shown in Tables 38 and 39 below. However, the present invention shall not be limited to these specific examples. Abbreviations in Tables 38 and 39 have the following meanings.

SMe: sulfomethyl (*—CH$_2$—SO$_3$H)
2-SEt: 2-sulfoethyl (*—CH$_2$CH$_2$—SO$_3$H)
3-S″Pr: 3-sulfo-n-propyl (*—CH$_2$CH$_2$CH$_2$—SO$_3$H)
4-S″Bu: 3-sulfo-n-butyl (*—CH$_2$CH$_2$CH$_2$CH$_2$—SO$_3$H)

The symbol "*" in the above formulae indicates a position of attachment to the oxygen atom.

TABLE 38

| No. | Q | R$^{11}$ | R$^{12}$ | A$^1$ |
|---|---|---|---|---|
| 1 | Cl | SMe | SMe | Formula (A1-9), R$^{414}$-R$^{421}$ = H |
| 2 | Cl | SMe | 2-SEt | Formula (A1-9), R$^{414}$-R$^{421}$ = H |
| 3 | Cl | SMe | 3-S″Pr | Formula (A1-9), R$^{414}$-R$^{421}$ = H |
| 4 | Cl | SMe | 4-S″Bu | Formula (A1-9), R$^{414}$-R$^{421}$ = H |
| 5 | Cl | 2-SEt | 2-SEt | Formula (A1-9), R$^{414}$-R$^{421}$ = H |
| 6 | Cl | 2-SEt | 3-S″Pr | Formula (A1-9), R$^{414}$-R$^{421}$ = H |
| 7 | Cl | 2-SEt | 4-S″Bu | Formula (A1-9), R$^{414}$-R$^{421}$ = H |
| 8 | Cl | 3-S″Pr | 3-S″Pr | Formula (A1-9), R$^{414}$-R$^{421}$ = H |
| 9 | Cl | 3-S″Pr | 4-S″Bu | Formula (A1-9), R$^{414}$-R$^{421}$ = H |
| 10 | Cl | 4-S″Bu | 4-S″Bu | Formula (A1-9), R$^{414}$-R$^{421}$ = H |
| 11 | Cl | 3-S″Pr | 3-S″Pr | Formula (A1-9), R$^{414}$-R$^{421}$ = Cl |
| 12 | Cl | 3-S″Pr | 3-S″Pr | Formula (A1-9), R$^{414}$-R$^{421}$ = CH$_3$ |
| 13 | Cl | 3-S″Pr | 3-S″Pr | Formula (A1-9), R$^{414}$, R$^{416}$, R$^{418}$, R$^{420}$ = H, R$^{415}$, R$^{417}$, R$^{419}$, R$^{421}$ = Cl |
| 14 | Cl | 3-S″Pr | 3-S″Pr | Formula (A1-9), R$^{414}$ = OH, R$^{415}$-R$^{421}$ = H |
| 15 | Cl | 3-S″Pr | 3-S″Pr | Formula (A1-9), R$^{414}$ = CH$_2$OH, R$^{415}$-R$^{421}$ = H |
| 16 | Br | SMe | SMe | Formula (A1-9), R$^{414}$-R$^{421}$ = H |
| 17 | Br | SMe | 2-SEt | Formula (A1-9), R$^{414}$-R$^{421}$ = H |
| 18 | Br | SMe | 3-S″Pr | Formula (A1-9), R$^{414}$-R$^{421}$ = H |
| 19 | Br | SMe | 4-S″Bu | Formula (A1-9), R$^{414}$-R$^{421}$ = H |
| 20 | Br | 2-SEt | 2-SEt | Formula (A1-9), R$^{414}$-R$^{421}$ = H |
| 21 | Br | 2-SEt | 3-S″Pr | Formula (A1-9), R$^{414}$-R$^{421}$ = H |
| 22 | Br | 2-SEt | 4-S″Bu | Formula (A1-9), R$^{414}$-R$^{421}$ = H |
| 23 | Br | 3-S″Pr | 3-S″Pr | Formula (A1-9), R$^{414}$-R$^{421}$ = H |
| 24 | Br | 3-S″Pr | 4-S″Bu | Formula (A1-9), R$^{414}$-R$^{421}$ = H |
| 25 | Br | 4-S″Bu | 4-S″Bu | Formula (A1-9), R$^{414}$-R$^{421}$ = H |
| 26 | Br | 3-S″Pr | 3-S″Pr | Formula (A1-9), R$^{414}$-R$^{421}$ = H |
| 27 | Br | 3-S″Pr | 3-S″Pr | Formula (A1-9), R$^{414}$-R$^{421}$ = CH$_3$ |
| 28 | Br | 3-S″Pr | 3-S″Pr | Formula (A1-9), R$^{414}$, R$^{416}$, R$^{418}$, R$^{420}$ = H, R$^{415}$, R$^{417}$, R$^{419}$, R$^{421}$ = Cl |
| 29 | Br | 3-S″Pr | 3-S″Pr | Formula (A1-9), R$^{414}$ = OH, R$^{415}$-R$^{421}$ = H |
| 30 | Br | 3-S″Pr | 3-S″Pr | Formula (A1-9), R$^{414}$ = CH$_2$OH, R$^{415}$-R$^{421}$ = H |

TABLE 39

| No. | Q | R$^{11}$ | R$^{12}$ | A$^1$ |
|---|---|---|---|---|
| 31 | F | SMe | SMe | Formula (A1-9), R$^{414}$-R$^{421}$ = H |
| 32 | F | SMe | 2-SEt | Formula (A1-9), R$^{414}$-R$^{421}$ = H |
| 33 | F | SMe | 3-S″Pr | Formula (A1-9), R$^{414}$-R$^{421}$ = H |
| 34 | F | SMe | 4-S″Bu | Formula (A1-9), R$^{414}$-R$^{421}$ = H |
| 35 | F | 2-SEt | 2-SEt | Formula (A1-9), R$^{414}$-R$^{421}$ = H |
| 36 | F | 2-SEt | 3-S″Pr | Formula (A1-9), R$^{414}$-R$^{421}$ = H |
| 37 | F | 2-SEt | 4-S″Bu | Formula (A1-9), R$^{414}$-R$^{421}$ = H |
| 38 | F | 3-S″Pr | 3-S″Pr | Formula (A1-9), R$^{414}$-R$^{421}$ = H |
| 39 | F | 3-S″Pr | 4-S″Bu | Formula (A1-9), R$^{414}$-R$^{421}$ = H |
| 40 | F | 4-S″Bu | 4-S″Bu | Formula (A1-9), R$^{414}$-R$^{421}$ = H |
| 41 | F | 3-S″Pr | 3-S″Pr | Formula (A1-9), R$^{414}$-R$^{421}$ = Cl |
| 42 | F | 3-S″Pr | 3-S″Pr | Formula (A1-9), R$^{414}$-R$^{421}$ = CH$_3$ |
| 43 | F | 3-S″Pr | 3-S″Pr | Formula (A1-9), R$^{414}$, R$^{416}$, R$^{418}$, R$^{420}$ = H, R$^{415}$, R$^{417}$, R$^{419}$, R$^{421}$ = Cl |
| 44 | F | 3-S″Pr | 3-S″Pr | Formula (A1-9), R$^{414}$ = OH, R$^{415}$-R$^{421}$ = H |
| 45 | F | 3-S″Pr | 3-S″Pr | Formula (A1-9), R$^{414}$ = CH$_2$OH, R$^{415}$-R$^{421}$ = H |

When A$^1$ in the above formula (1) is a cyclic amine group, preferred compounds include, for example, one in which in the above formula (1-1), Q is a chlorine atom, x is 3, and A$^1$ is a group represented by the above formula (A1-9), and R$^{414}$ to R$^{421}$ in the above formula (A1-9) are each a hydrogen atom.

With regard to all components and items, combinations of those preferred are more preferred, and combinations of those more preferred are even more preferred. The same applies to combinations of those preferred and those more preferred and the like.

The compound represented by the above formula (1) can be manufactured as follows. It should be noted that Q, x, R$^{11}$, and R$^{12}$, which are appropriately used in the following formulae (10-1) to (14), each have the same meaning as defined in the formula (1).

First, a compound represented by the following formula (10-1) obtained in accordance with the method described in Japanese Unexamined Patent Application Publication No. 2004-75719 by using 2-amino-4-halogenophenol as a raw material is converted into a methyl-ω-sulfonic acid derivative represented by the following formula (11) using sodium bisulfite and formalin. Then, the resulting methyl-ω-sulfonic acid derivative represented by the following formula (11) and a compound represented by the following formula (12) diazotized according to the conventional method are subjected to a coupling reaction at a reaction temperature of 0 to 15° C. and at pH 4 to 6. Subsequently, a hydrolysis reaction is performed at a reaction temperature of 80 to 95° C. and at pH 10.5 to 11.5 to obtain a compound represented by the following formula (13-1). Moreover, a compound represented by the following formula (13-2) is obtained as described above except that a compound represented by the following formula (10-2) is used instead of the compound represented by the following formula (10-1).

(10-1)

(10-2)

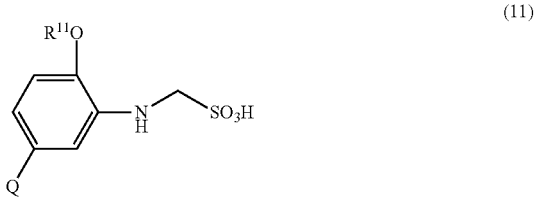

(11)

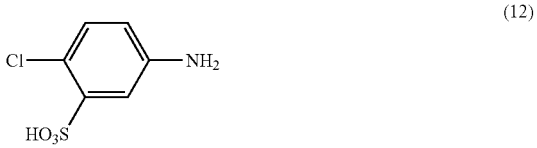

(12)

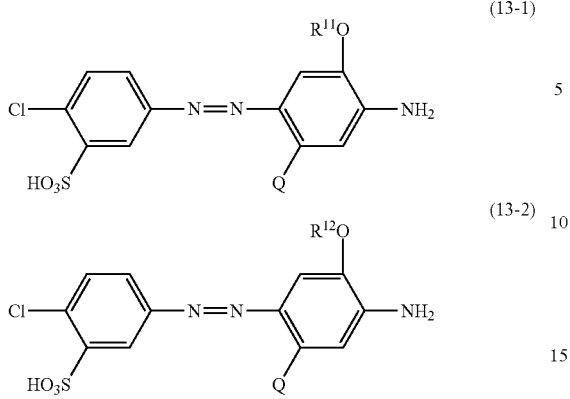

(13-1)

(13-2)

Subsequently, the compound (1 equivalent) represented by the above formula (13-1), the compound (1 equivalent) represented by the above formula (13-2), and a cyanuric halide (such as cyanuric chloride, 1 equivalent) are condensed at a reaction temperature of 15 to 45° C. and at pH 5 to 8 to obtain a compound represented by the following formula (14). It should be noted that one of the compounds (1 equivalent) represented by the above formula (13-1) and the compound (1 equivalent) represented by the above formula (13-2) may be reacted with a cyanuric halide (1 equivalent), and then the resulting reaction product may further be reacted with the other compound.

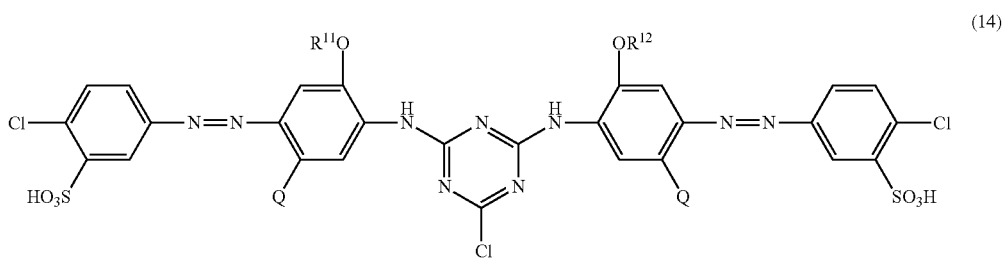

(14)

Subsequently, the compound represented by the above formula (14) and a compound represented by a formula H-A$^1$ are reacted at a reaction temperature of 55 to 95° C. and at pH 6 to 9 to cause a de-HCl reaction. This can lead to production of the compound represented by the above formula (1).

[Compound Represented by Formula (2)]

In the above formula (2), each $Q^{21}$ to $Q^{24}$ independently represents a halogen atom. Halogen atoms include a fluorine atom, a chlorine atom, a bromine atom, and an iodine atom. Among these, a fluorine atom or a chlorine atom is preferred, and a chlorine atom is more preferred.

In the above formula (2), each $R^{21}$ to $R^{24}$ independently represents an alkyl group substituted with an ionic hydrophilic group. The carbon number of an alkyl group moiety is usually 1 to 4, preferably 1 to 3, and more preferably 3. Ionic hydrophilic groups include a group selected from a sulfo group, a carboxy group, a phospho group, and a quaternary ammonium group. Among these, preferred is a group selected from a sulfo group, a carboxy group, and a phospho group. More preferred is a group selected from a sulfo group and a carboxy group. Even more preferred is a sulfo group. There is no particular limitation for the number of substitutions in an ionic hydrophilic group, but it is usually 1 to 5, preferably 1 to 4, more preferably 1 to 3, even more preferably 1 or 2, and in particular preferably 1.

Specific examples of an alkyl group substituted with an ionic hydrophilic group include, for example, a sulfomethyl group, a sulfoethyl group, a 2,3-disulfopropyl group, a 3-sulfopropyl group, a 4-sulfobutyl group, a 5-sulfopentyl group, a 6-sulfohexyl group, a 7-sulfoheptyl group, an 8-sulfooctyl group, a carboxymethyl group, a carboxyethyl group, a 3-carboxypropyl group, a 4-carboxybutyl group, a 5-carboxypentyl group, a 6-carboxyhexyl group, a 7-carboxyheptyl group, an 8-carboxyoctyl group, a phosphomethyl group, a phosphoethyl group, a 3-phosphopropyl group, a 4-phosphobutyl group, a 5-phosphopentyl group, a 6-phosphohexyl group, a 7-phosphoheptyl group, an 8-phosphooctyl group, a trimethylammoniummethyl group, a trimethylammoniumethyl group, a 3-trimethylammoniumpropyl group, a 4-trimethylammoniumbutyl group, a 5-trimethylammoniumpentyl group, a 6-trimethylammoniumhexyl group, a 7-trimethylammoniumheptyl group, an 8-trimethylammoniumoctyl group, a 2-methyl-3-sulfopropyl group, a 2,2-dimethyl-3-sulfopropyl group, a 4-sulfocyclohexyl group, a 2,5-disulfocyclohexylmethyl group and the like. Preferred is a 3-sulfopropyl group.

In the above formula (2), $A^2$ represents a divalent group. Divalent groups include, for example, an alkylenediamino group, a nitrogen-containing heterocyclic group, an arylenediamino group, an aminoalkylthio group, and an aminoarylthio group. Among these, preferred are an alkylenediamino group and a nitrogen-containing heterocyclic group. More preferred is a nitrogen-containing heterocyclic group.

Alkylenediamino groups include a group having a linear, branched, or cyclic alkylene moiety. The alkylene moiety is preferably linear or branched, more preferably linear. The carbon number of the alkylene moiety is usually 2 to 12, preferably 2 to 8, more preferably 2 to 6, and even more preferably 2 to 4. Specific examples of the alkylenediamino group include, for example, 1,2-ethylenediamino, 1,2-propylenediamino, 1,3-propylenediamino, 1,2-butylenediamino, 1,4-butylenediamino, 1,2-pentylenediamino, 1,5-pentylenediamino, 1,2-hexylenediamino, 1,6-hexylenediamino, 2-methyl-1,3-propylenediamino, 1,2-cyclopentylenediamino, 1,2-cyclohexylenediamine, 1,4-piperazinyl and the like. Among these, 1,4-piperazinyl is preferred.

Nitrogen-containing heterocyclic groups include a nitrogen-containing heterocyclic group of a 4- to 9-membered ring (preferably a 5- to 7-membered ring, more preferably a 5- or 6-membered ring, and even more preferably a 6-membered ring) having two nitrogen atoms as ring atoms. Specific examples of the nitrogen-containing heterocyclic group include, for example, 1,2-diazetidine, pyrazolidine, hexahydropyridazine, hexahydropyrimidine, piperazine, 1,2-diazepane, 1,3-diazepane, 1,4-diazepane, 1,2-diazocane, 1,4-diazocane, and 1,4-diazonane. Among these, piperazine (in particular 1,4-piperazinediyl) is preferred.

Arylenediamino groups include an arylenediamino group usually having 6 to 14 carbon atoms, preferably 6 to 10 carbon atoms, and more preferably 6 carbon atoms. Specific examples of the arylenediamino group include, for example, 1,2-phenylenediamino, 1,3-phenylenediamino, 1,4-phenylenediamino, 1,8-naphthylenediamino, 2,8-naphthylenediamino and the like.

Aminoalkylthio groups include a group having a linear, branched, or cyclic alkyl moiety. The carbon number of the alkyl moiety is usually 2 to 12, preferably 2 to 8, more preferably 2 to 6, and even more preferably 2 to 4. Specific examples of the aminoalkylthio group include, for example, aminoethylthio, aminopropylthio, aminobutylthio, aminopentylthio, aminohexylthio, 3-amino-2-methylpropane-1-thio, 2-aminocyclohexane-1-thio and the like.

Aminoarylthio groups include an aminoarylthio group usually having 6 to 14 carbon atoms, preferably 6 to 10 carbon atoms, more preferably 6 carbon atoms. Specific examples of the aminoarylthio group include, for example, 2-aminophenylthio, 4-aminophenylthio, 8-aminonaphthyl-2-thio and the like.

Further, $A^2$ may usually have 1 to 5 substituents, preferably 1 to 4 substituents, more preferably 1 to 3 substituents, even more preferably 1 or 2 substituents, and in particular preferably 1 substituent. There is no particular limitation for the substituents, but examples include a halogen atom, an alkyl group, an aralkyl group, an alkenyl group, an alkynyl group, an alkoxy group, an aryl group, a heterocyclic group, a cyano group, a hydroxy group, a nitro group, an aryloxy group, a silyloxy group, and a heterocyclic oxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, an alkyl- or arylsulfinyl group, an alkyl- or arylsulfonyl group, an acyl group, an aryloxycarbonyl group, an alkoxycarbonyl group, a carbamoyl group and the like.

A preferred compound among the compounds represented by the above formula (2) is one represented by the above formula (2-1). In the above formula (2-1), $Q^{21}$ to $Q^{24}$ and $A^2$ have the same meanings as defined in the above formula (2), including those preferred and the like. In the above formula (2-1), each x independently represents an integer of 2 to 4, and preferably 3.

Specific examples of the compound represented by the above formula (2) are shown in Tables 40 to 46 below. However, the present invention shall not be limited to these specific examples. Abbreviations in Tables 40 to 46 have the following meanings.

SMe: sulfomethyl (*—$CH_2$—$SO_3H$)
2-SEt: 2-sulfoethyl (*—$CH_2CH_2$—$SO_3H$)
3-S″Pr: 3-sulfo-n-propyl (*—$CH_2CH_2CH_2$—$SO_3H$)
4-S″Bu: 3-sulfo-n-butyl (*—$CH_2CH_2CH_2CH_2$—$SO_3H$)

The symbol "*" in the above formulae indicates a position of attachment to the oxygen atom.

Further, the formulae (A2-1) to (A2-5) indicated in the "$A^2$" columns in Tables 40 to 46 are represented by the following formulae, respectively. The symbol "*" in the following formulae indicates a position of attachment to the triazine ring.

(A2-1)

(A2-2)

(A2-3)

(A2-4)

-continued

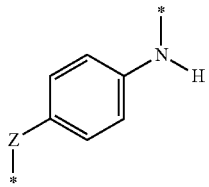

(A2-5)

TABLE 40

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 1 | Cl | Cl | Cl | Cl | SMe | SMe | SMe | SMe | Formula (A2-1) n = 2, Z = NH |
| 2 | Cl | Cl | Cl | Cl | SMe | 2-SEt | SMe | 2-SEt | Formula (A2-1) n = 2, Z = NH |
| 3 | Cl | Cl | Cl | Cl | SMe | 3-S"Pr | SMe | 3-S"Pr | Formula (A2-1) n = 2, Z = NH |
| 4 | Cl | Cl | Cl | Cl | SMe | 4-S"Bu | SMe | 4-S"Bu | Formula (A2-1) n = 2, Z = NH |
| 5 | Cl | Cl | Cl | Cl | 2-SEt | 2-SEt | 2-SEt | 2-SEt | Formula (A2-1) n = 2, Z = NH |
| 6 | Cl | Cl | Cl | Cl | 2-SEt | 3-S"Pr | 2-SEt | 3-S"Pr | Formula (A2-1) n = 2, Z = NH |
| 7 | Cl | Cl | Cl | Cl | 2-SEt | 4-S"Bu | 2-SEt | 4-S"Bu | Formula (A2-1) n = 2, Z = NH |
| 8 | Cl | Cl | Cl | Cl | 3-S"Pr | 3-S"Pr | 3-S"Pr | 3-S"Pr | Formula (A2-1) n = 2, Z = NH |
| 9 | Cl | Cl | Cl | Cl | 3-S"Pr | 4-S"Bu | 3-S"Pr | 4-S"Bu | Formula (A2-1) n = 2, Z = NH |
| 10 | Cl | Cl | Cl | Cl | 4-S"Bu | 4-S"Bu | 4-S"Bu | 4-S"Bu | Formula (A2-1) n = 2, Z = NH |
| 11 | Cl | Cl | Cl | Cl | SMe | SMe | SMe | SMe | Formula (A2-1), n = 2, Z = S |
| 12 | Cl | Cl | Cl | Cl | SMe | 2-SEt | SMe | 2-SEt | Formula (A2-1), n = 2, Z = S |
| 13 | Cl | Cl | Cl | Cl | SMe | 3-S"Pr | SMe | 3-S"Pr | Formula (A2-1), n = 2, Z = S |
| 14 | Cl | Cl | Cl | Cl | SMe | 4-S"Bu | SMe | 4-S"Bu | Formula (A2-1), n = 2, Z = S |
| 15 | Cl | Cl | Cl | Cl | 2-SEt | 2-SEt | 2-SEt | 2-SEt | Formula (A2-1), n = 2, Z = S |
| 16 | Cl | Cl | Cl | Cl | 2-SEt | 3-S"Pr | 2-SEt | 3-S"Pr | Formula (A2-1), n = 2, Z = S |
| 17 | Cl | Cl | Cl | Cl | 2-SEt | 4-S"Bu | 2-SEt | 4-S"Bu | Formula (A2-1), n = 2, Z = S |
| 18 | Cl | Cl | Cl | Cl | 3-S"Pr | 3-S"Pr | 3-S"Pr | 3-S"Pr | Formula (A2-1), n = 2, Z = S |
| 19 | Cl | Cl | Cl | Cl | 3-S"Pr | 4-S"Bu | 3-S"Pr | 4-S"Bu | Formula (A2-1), n = 2, Z = S |
| 20 | Cl | Cl | Cl | Cl | 4-S"Bu | 4-S"Bu | 4-S"Bu | 4-S"Bu | Formula (A2-1), n = 2, Z = S |
| 21 | Cl | Cl | Cl | Cl | SMe | SMe | SMe | SMe | Formula (A2-1), n = 3, Z = NH |
| 22 | Cl | Cl | Cl | Cl | SMe | 2-SEt | SMe | 2-SEt | Formula (A2-1), n = 3, Z = NH |
| 23 | Cl | Cl | Cl | Cl | SMe | 3-S"Pr | SMe | 3-S"Pr | Formula (A2-1) n = 3, Z = NH |
| 24 | Cl | Cl | Cl | Cl | SMe | 4-S"Bu | SMe | 4-S"Bu | Formula (A2-1) n = 3, Z = NH |
| 25 | Cl | Cl | Cl | Cl | 2-SEt | 2-SEt | 2-SEt | 2-SEt | Formula (A2-1) n = 3, Z = NH |
| 26 | Cl | Cl | Cl | Cl | 2-SEt | 3-S"pr | 2-SEt | 3-S"Pr | Formula (A2-1) n = 3, Z = NH |
| 27 | Cl | Cl | Cl | Cl | 2-SEt | 4-S"Bu | 2-SEt | 4-S"Bu | Formula (A2-1) n = 3, Z = NH |
| 28 | Cl | Cl | Cl | Cl | 3-S"Pr | 3-S"Pr | 3-S"Pr | 3-S"Pr | Formula (A2-1) n = 3, Z = NH |
| 29 | Cl | Cl | Cl | Cl | 3-S"Pr | 4-S"Bu | 3-S"Pr | 4-S"Bu | Formula (A2-1) n = 3, Z = NH |
| 30 | Cl | Cl | Cl | Cl | 4-S"Bu | 4-S"Bu | 4-S"Bu | 4-S"Bu | Formula (A2-1) n = 3, Z = NH |

TABLE 41

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 31 | Cl | Cl | Cl | Cl | SMe | SMe | SMe | SMe | Formula (A2-1) n = 3, Z = S |
| 32 | Cl | Cl | Cl | Cl | SMe | 2-SEt | SMe | 2-SEt | Formula (A2-1) n = 3, Z = S |
| 33 | Cl | Cl | Cl | Cl | SMe | 3-S"Pr | SMe | 3-S"Pr | Formula (A2-1) n = 3, Z = S |
| 34 | Cl | Cl | Cl | Cl | SMe | 4-S"Bu | SMe | 4-S"Bu | Formula (A2-1) n = 3, Z = S |
| 35 | Cl | Cl | Cl | Cl | 2-SEt | 2-SEt | 2-SEt | 2-SEt | Formula (A2-1) n = 3, Z = S |
| 36 | Cl | Cl | Cl | Cl | 2-SEt | 3-S"Pr | 2-SEt | 3-S"Pr | Formula (A2-1) n = 3, Z = S |
| 37 | Cl | Cl | Cl | Cl | 2-SEt | 4-S"Bu | 2-SEt | 4-S"Bu | Formula (A2-1) n = 3, Z = S |
| 38 | Cl | Cl | Cl | Cl | 3-S"Pr | 3-S"Pr | 3-S"Pr | 3-S"Pr | Formula (A2-1) n = 3, Z = S |
| 39 | Cl | Cl | Cl | Cl | 3-S"Pr | 4-S"Bu | 3-S"Pr | 4-S"Bu | Formula (A2-1) n = 3, Z = S |
| 40 | Cl | Cl | Cl | Cl | 4-S"Bu | 4-S"Bu | 4-S"Bu | 4-S"Bu | Formula (A2-1) n = 3, Z = S |
| 41 | Cl | Cl | Cl | Cl | SMe | SMe | SMe | SMe | Formula (A2-2) |
| 42 | Cl | Cl | Cl | Cl | SMe | 2-SEt | SMe | 2-SEt | Formula (A2-2) |
| 43 | Cl | Cl | Cl | Cl | SMe | 3-S"Pr | SMe | 3-S"Pr | Formula (A2-2) |
| 44 | Cl | Cl | Cl | Cl | SMe | 4-S"Bu | SMe | 4-S"Bu | Formula (A2-2) |
| 45 | Cl | Cl | Cl | Cl | 2-SEt | 2-SEt | 2-SEt | 2-SEt | Formula (A2-2) |
| 46 | Cl | Cl | Cl | Cl | 2-SEt | 3-S"Pr | 2-SEt | 3-S"Pr | Formula (A2-2) |
| 47 | Cl | Cl | Cl | Cl | 2-SEt | 4-S"Bu | 2-SEt | 4-S"Bu | Formula (A2-2) |
| 48 | Cl | Cl | Cl | Cl | 3-S"Pr | 3-S"Pr | 3-S"Pr | 3-S"Pr | Formula (A2-2) |
| 49 | Cl | Cl | Cl | Cl | 3-S"Pr | 4-S"Bu | 3-S"Pr | 4-S"Bu | Formula (A2-2) |
| 50 | Cl | Cl | Cl | Cl | 4-S"Bu | 4-S"Bu | 4-S"Bu | 4-S"Bu | Formula (A2-2) |
| 51 | Cl | Cl | Cl | Cl | SMe | SMe | SMe | SMe | Formula (A2-3), Z = NH |
| 52 | Cl | Cl | Cl | Cl | SMe | 2-SEt | SMe | 2-SEt | Formula (A2-3), Z = NH |
| 53 | Cl | Cl | Cl | Cl | SMe | 3-S"Pr | SMe | 3-S"Pr | Formula (A2-3), Z = NH |
| 54 | Cl | Cl | Cl | Cl | SMe | 4-S"Bu | SMe | 4-S"Bu | Formula (A2-3), Z = NH |
| 55 | Cl | Cl | Cl | Cl | 2-SEt | 2-SEt | 2-SEt | 2-SEt | Formula (A2-3), Z = NH |

TABLE 41-continued

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 56 | Cl | Cl | Cl | Cl | 2-SEt | 3-S"Pr | 2-SEt | 3-S"Pr | Formula (A2-3), Z = NH |
| 57 | Cl | Cl | Cl | Cl | 2-SEt | 4-S"Bu | 2-SEt | 4-S"Bu | Formula (A2-3), Z = NH |
| 58 | Cl | Cl | Cl | Cl | 3-S"Pr | 3-S"Pr | 3-S"Pr | 3-S"Pr | Formula (A2-3), Z = NH |
| 59 | Cl | Cl | Cl | Cl | 3-S"Pr | 4-S"Bu | 3-S"Pr | 4-S"Bu | Formula (A2-3), Z = NH |
| 60 | Cl | Cl | Cl | Cl | 4-S"Bu | 4-S"Bu | 4-S"Bu | 4-S"Bu | Formula (A2-3), Z = NH |

TABLE 42

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 61 | Cl | Cl | Cl | Cl | SMe | SMe | SMe | SMe | Formula (A2-3), Z = S |
| 62 | Cl | Cl | Cl | Cl | SMe | 2-SEt | SMe | 2-SEt | Formula (A2-3), Z = S |
| 63 | Cl | Cl | Cl | Cl | SMe | 3-S"Pr | SMe | 3-S"Pr | Formula (A2-3), Z = S |
| 64 | Cl | Cl | Cl | Cl | SMe | 4-S"Bu | SMe | 4-S"Bu | Formula (A2-3), Z = S |
| 65 | Cl | Cl | Cl | Cl | 2-SEt | 2-SEt | 2-SEt | 2-SEt | Formula (A2-3), Z = S |
| 66 | Cl | Cl | Cl | Cl | 2-SEt | 3-S"Pr | 2-SEt | 3-S"Pr | Formula (A2-3), Z = S |
| 67 | Cl | Cl | Cl | Cl | 2-SEt | 4-S"Bu | 2-SEt | 4-S"Bu | Formula (A2-3), Z = S |
| 68 | Cl | Cl | Cl | Cl | 3-S"Pr | 3-S"Pr | 3-S"Pr | 3-S"Pr | Formula (A2-3), Z = S |
| 69 | Cl | Cl | Cl | Cl | 3-S"Pr | 4-S"Bu | 3-S"Pr | 4-S"Bu | Formula (A2-3), Z = S |
| 70 | Cl | Cl | Cl | Cl | 4-S"Bu | 4-S"Bu | 4-S"Bu | 4-S"Bu | Formula (A2-3), Z = S |
| 71 | Cl | Cl | Cl | Cl | SMe | SMe | SMe | SMe | Formula (A2-4), Z = NH |
| 72 | Cl | Cl | Cl | Cl | SMe | 2-SEt | SMe | 2-SEt | Formula (A2-4), Z = NH |
| 73 | Cl | Cl | Cl | Cl | SMe | 3-S"Pr | SMe | 3-S"Pr | Formula (A2-4), Z = NH |
| 74 | Cl | Cl | Cl | Cl | SMe | 4-S"Bu | SMe | 4-S"Bu | Formula (A2-4), Z = NH |
| 75 | Cl | Cl | Cl | Cl | 2-SEt | 2-SEt | 2-SEt | 2-SEt | Formula (A2-4), Z = NH |
| 76 | Cl | Cl | Cl | Cl | 2-SEt | 3-S"Pr | 2-SEt | 3-S"Pr | Formula (A2-4), Z = NH |
| 77 | Cl | Cl | Cl | Cl | 2-SEt | 4-S"Bu | 2-SEt | 4-S"Bu | Formula (A2-4), Z = NH |
| 78 | Cl | Cl | Cl | Cl | 3-S"Pr | 3-S"Pr | 3-S"Pr | 3-S"Pr | Formula (A2-4), Z = NH |
| 79 | Cl | Cl | Cl | Cl | 3-S"Pr | 4-S"Bu | 3-S"Pr | 4-S"Bu | Formula (A2-4), Z = NH |
| 80 | Cl | Cl | Cl | Cl | 4-S"Bu | 4-S"Bu | 4-S"Bu | 4-S"Bu | Formula (A2-4), Z = NH |
| 81 | Cl | Cl | Cl | Cl | SMe | SMe | SMe | SMe | Formula (A2-4), Z = S |
| 82 | Cl | Cl | Cl | Cl | SMe | 2-SEt | SMe | 2-SEt | Formula (A2-4), Z = S |
| 83 | Cl | Cl | Cl | Cl | SMe | 3-S"Pr | SMe | 3-S"Pr | Formula (A2-4), Z = S |
| 84 | Cl | Cl | Cl | Cl | SMe | 4-S"Bu | SMe | 4-S"Bu | Formula (A2-4), Z = S |
| 85 | Cl | Cl | Cl | Cl | 2-SEt | 2-SEt | 2-SEt | 2-SEt | Formula (A2-4), Z = S |
| 86 | Cl | Cl | Cl | Cl | 2-SEt | 3-S"Pr | 2-SEt | 3-S"Pr | Formula (A2-4), Z = S |
| 87 | Cl | Cl | Cl | Cl | 2-SEt | 4-S"Bu | 2-SEt | 4-S"Bu | Formula (A2-4), Z = S |
| 88 | Cl | Cl | Cl | Cl | 3-S"Pr | 3-S"Pr | 3-S"Pr | 3-S"Pr | Formula (A2-4), Z = S |
| 89 | Cl | Cl | Cl | Cl | 3-S"Pr | 4-S"Bu | 3-S"Pr | 4-S"Bu | Formula (A2-4), Z = S |
| 90 | Cl | Cl | Cl | Cl | 4-S"Bu | 4-S"Bu | 4-S"Bu | 4-S"Bu | Formula (A2-4), Z = S |

TABLE 43

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 91 | Cl | Cl | Cl | Cl | SMe | SMe | SMe | SMe | Formula (A2-5), Z = NH |
| 92 | Cl | Cl | Cl | Cl | SMe | 2-SEt | SMe | 2-SEt | Formula (A2-5), Z = NH |
| 93 | Cl | Cl | Cl | Cl | SMe | 3-S"Pr | SMe | 3-S"Pr | Formula (A2-5), Z = NH |
| 94 | Cl | Cl | Cl | Cl | SMe | 4-S"Bu | SMe | 4-S"Bu | Formula (A2-5), Z = NH |
| 95 | Cl | Cl | Cl | Cl | 2-SEt | 2-SEt | 2-SEt | 2-SEt | Formula (A2-5), Z = NH |
| 96 | Cl | Cl | Cl | Cl | 2-SEt | 3-S"Pr | 2-SEt | 3-S"Pr | Formula (A2-5), Z = NH |
| 97 | Cl | Cl | Cl | Cl | 2-SEt | 4-S"Bu | 2-SEt | 4-S"Bu | Formula (A2-5), Z = NH |
| 98 | Cl | Cl | Cl | Cl | 3-S"Pr | 3-S"Pr | 3-S"Pr | 3-S"Pr | Formula (A2-5), Z = NH |
| 99 | Cl | Cl | Cl | Cl | 3-S"Pr | 4-S"Bu | 3-S"Pr | 4-S"Bu | Formula (A2-5), Z = NH |
| 100 | Cl | Cl | Cl | Cl | 4-S"Bu | 4-S"Bu | 4-S"Bu | 4-S"Bu | Formula (A2-5), Z = NH |
| 101 | Cl | Cl | Cl | Cl | SMe | SMe | SMe | SMe | Formula (A2-5), Z = S |
| 102 | Cl | Cl | Cl | Cl | SMe | 2-SEt | SMe | 2-SEt | Formula (A2-5), Z = S |
| 103 | Cl | Cl | Cl | Cl | SMe | 3-S"Pr | SMe | 3-S"Pr | Formula (A2-5), Z = S |
| 104 | Cl | Cl | Cl | Cl | SMe | 4-S"Bu | SMe | 4-S"Bu | Formula (A2-5), Z = S |
| 105 | Cl | Cl | Cl | Cl | 2-SEt | 2-SEt | 2-SEt | 2-SEt | Formula (A2-5), Z = S |
| 106 | Cl | Cl | Cl | Cl | 2-SEt | 3-S"Pr | 2-SEt | 3-S"Pr | Formula (A2-5), Z = S |
| 107 | Cl | Cl | Cl | Cl | 2-SEt | 4-S"Bu | 2-SEt | 4-S"Bu | Formula (A2-5), Z = S |
| 108 | Cl | Cl | Cl | Cl | 3-S"Pr | 3-S"Pr | 3-S"Pr | 3-S"Pr | Formula (A2-5), Z = S |
| 109 | Cl | Cl | Cl | Cl | 3-S"Pr | 4-S"Bu | 3-S"Pr | 4-S"Bu | Formula (A2-5), Z = S |
| 110 | Cl | Cl | Cl | Cl | 4-S"Bu | 4-S"Bu | 4-S"Bu | 4-S"Bu | Formula (A2-5), Z = S |
| 111 | Cl | Cl | F | F | SMe | SMe | SMe | SMe | Formula (A2-2) |
| 112 | Cl | Cl | F | F | SMe | 2-SEt | SMe | 2-SEt | Formula (A2-2) |
| 113 | Cl | Cl | F | F | SMe | 3-S"Pr | SMe | 3-S"Pr | Formula (A2-2) |
| 114 | Cl | Cl | F | F | SMe | 4-S'Bu | SMe | 4-S'Bu | Formula (A2-2) |

TABLE 43-continued

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 115 | Cl | Cl | F | F | 2-SEt | 2-SEt | 2-SEt | 2-SEt | Formula (A2-2) |
| 116 | Cl | Cl | F | F | 2-SEt | 3-S"Pr | 2-SEt | 3-S"Pr | Formula (A2-2) |
| 117 | Cl | Cl | F | F | 2-SEt | 4-S"Bu | 2-SEt | 4-S"Bu | Formula (A2-2) |
| 118 | Cl | Cl | F | F | 3-S"Pr | 3-S"Pr | 3-S"Pr | 3-S"Pr | Formula (A2-2) |
| 119 | Cl | Cl | F | F | 3-S"Pr | 4-S"Bu | 3-S"Pr | 4-S"Bu | Formula (A2-2) |
| 120 | Cl | Cl | F | F | 4-S"Bu | 4-S"Bu | 4-S"Bu | 4-S"Bu | Formula (A2-2) |

TABLE 44

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 121 | Cl | F | Cl | F | SMe | SMe | SMe | SMe | Formula (A2-2) |
| 122 | Cl | F | Cl | F | SMe | 2-SEt | SMe | 2-SEt | Formula (A2-2) |
| 123 | Cl | F | Cl | F | SMe | 3-S"Pr | SMe | 3-S"Pr | Formula (A2-2) |
| 124 | Cl | F | Cl | F | SMe | 4-S"Bu | SMe | 4-S"Bu | Formula (A2-2) |
| 125 | Cl | F | Cl | F | 2-SEt | 2-SEt | 2-SEt | 2-SEt | Formula (A2-2) |
| 126 | Cl | F | Cl | F | 2-SEt | 3-S"Pr | 2-SEt | 3-S"Pr | Formula (A2-2) |
| 127 | Cl | F | Cl | F | 2-SEt | 4-S"Bu | 2-SEt | 4-S"Bu | Formula (A2-2) |
| 128 | Cl | F | Cl | F | 3-S"Pr | 3-S"Pr | 3-S"Pr | 3-S"Pr | Formula (A2-2) |
| 129 | Cl | F | Cl | F | 3-S"Pr | 4-S"Bu | 3-S"Pr | 4-S"Bu | Formula (A2-2) |
| 130 | Cl | F | Cl | F | 4-S"Bu | 4-S"Bu | 4-S"Bu | 4-S"Bu | Formula (A2-2) |
| 131 | Cl | Cl | Br | Br | SMe | SMe | SMe | SMe | Formula (A2-2) |
| 132 | Cl | Cl | Br | Br | SMe | 2-SEt | SMe | 2-SEt | Formula (A2-2) |
| 133 | Cl | Cl | Br | Br | SMe | 3-S"Pr | SMe | 3-S"Pr | Formula (A2-2) |
| 134 | Cl | Cl | Br | Br | SMe | 4-S"Bu | SMe | 4-S"Bu | Formula (A2-2) |
| 135 | Cl | Cl | Br | Br | 2-SEt | 2-SEt | 2-SEt | 2-SEt | Formula (A2-2) |
| 136 | Cl | Cl | Br | Br | 2-SEt | 3-S"Pr | 2-SEt | 3-S"Pr | Formula (A2-2) |
| 137 | Cl | Cl | Br | Br | 2-SEt | 4-S"Bu | 2-SEt | 4-S"Bu | Formula (A2-2) |
| 138 | Cl | Cl | Br | Br | 3-S"Pr | 3-S"Pr | 3-S"Pr | 3-S"Pr | Formula (A2-2) |
| 139 | Cl | Cl | Br | Br | 3-S"Pr | 4-S"Bu | 3-S"Pr | 4-S"Bu | Formula (A2-2) |
| 140 | Cl | Cl | Br | Br | 4-S"Bu | 4-S"Bu | 4-S"Bu | 4-S"Bu | Formula (A2-2) |
| 141 | Cl | Br | Cl | Br | SMe | SMe | SMe | SMe | Formula (A2-2) |
| 142 | Cl | Br | Cl | Br | SMe | 2-SEt | SMe | 2-SEt | Formula (A2-2) |
| 143 | Cl | Br | Cl | Br | SMe | 3-S"Pr | SMe | 3-S"Pr | Formula (A2-2) |
| 144 | Cl | Br | Cl | Br | SMe | 4-S"Bu | SMe | 4-S"Bu | Formula (A2-2) |
| 145 | Cl | Br | Cl | Br | 2-SEt | 2-SEt | 2-SEt | 2-SEt | Formula (A2-2) |
| 146 | Cl | Br | Cl | Br | 2-SEt | 3-S"Pr | 2-SEt | 3-S"Pr | Formula (A2-2) |
| 147 | Cl | Br | Cl | Br | 2-SEt | 4-S"Bu | 2-SEt | 4-S"Bu | Formula (A2-2) |
| 148 | Cl | Br | Cl | Br | 3-S"Pr | 3-S"Pr | 3-S"Pr | 3-S"Pr | Formula (A2-2) |
| 149 | Cl | Br | Cl | Br | 3-S"Pr | 4-S"Bu | 3-S"Pr | 4-S"Bu | Formula (A2-2) |
| 150 | Cl | Br | Cl | Br | 4-S"Bu | 4-S"Bu | 4-S"Bu | 4-S"Bu | Formula (A2-2) |

TABLE 45

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 151 | F | F | Br | Br | SMe | SMe | SMe | SMe | Formula (A2-2) |
| 152 | F | F | Br | Br | SMe | 2-SEt | SMe | 2-SEt | Formula (A2-2) |
| 153 | F | F | Br | Br | SMe | 3-S"Pr | SMe | 3-S"Pr | Formula (A2-2) |
| 154 | F | F | Br | Br | SMe | 4-S"Bu | SMe | 4-S"Bu | Formula (A2-2) |
| 155 | F | F | Br | Br | 2-SEt | 2-SEt | 2-SEt | 2-SEt | Formula (A2-2) |
| 156 | F | F | Br | Br | 2-SEt | 3-S"Pr | 2-SEt | 3-S"Pr | Formula (A2-2) |
| 157 | F | F | Br | Br | 2-SEt | 4-S"Bu | 2-SEt | 4-S"Bu | Formula (A2-2) |
| 158 | F | F | Br | Br | 3-S"Pr | 3-S"Pr | 3-S"Pr | 3-S"Pr | Formula (A2-2) |
| 159 | F | F | Br | Br | 3-S"Pr | 4-S"Bu | 3-S"Pr | 4-S"Bu | Formula (A2-2) |
| 160 | F | F | Br | Br | 4-S"Bu | 4-S"Bu | 4-S"Bu | 4-S"Bu | Formula (A2-2) |
| 161 | F | Br | F | Br | SMe | SMe | SMe | SMe | Formula (A2-2) |
| 162 | F | Br | F | Br | SMe | 2-SEt | SMe | 2-SEt | Formula (A2-2) |
| 163 | F | Br | F | Br | SMe | 3-S"Pr | SMe | 3-S"Pr | Formula (A2-2) |
| 164 | F | Br | F | Br | SMe | 4-S"Bu | SMe | 4-S"Bu | Formula (A2-2) |
| 165 | F | Br | F | Br | 2-SEt | 2-SEt | 2-SEt | 2-SEt | Formula (A2-2) |
| 166 | F | Br | F | Br | 2-SEt | 3-S"Pr | 2-SEt | 3-S"Pr | Formula (A2-2) |
| 167 | F | Br | F | Br | 2-SEt | 4-S"Bu | 2-SEt | 4-S"Bu | Formula (A2-2) |
| 168 | F | Br | F | Br | 3-S"Pr | 3-S"Pr | 3-S"Pr | 3-S"Pr | Formula (A2-2) |
| 169 | F | Br | F | Br | 3-S"Pr | 4-S"Bu | 3-S"Pr | 4-S"Bu | Formula (A2-2) |
| 170 | F | Br | F | Br | 4-S"Bu | 4-S"Bu | 4-S"Bu | 4-S"Bu | Formula (A2-2) |
| 171 | F | F | F | F | SMe | SMe | SMe | SMe | Formula (A2-2) |
| 172 | F | F | F | F | SMe | 2-SEt | SMe | 2-SEt | Formula (A2-2) |
| 173 | F | F | F | F | SMe | 3-S"Pr | SMe | 3-S"Pr | Formula (A2-2) |

TABLE 45-continued

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 174 | F | F | F | F | SMe | 4-S"Bu | SMe | 4-S"Bu | Formula (A2-2) |
| 175 | F | F | F | F | 2-SEt | 2-SEt | 2-SEt | 2-SEt | Formula (A2-2) |
| 176 | F | F | F | F | 2-SEt | 3-S"Pr | 2-SEt | 3-S"Pr | Formula (A2-2) |
| 177 | F | F | F | F | 2-SEt | 4-S"Bu | 2-SEt | 4-S"Bu | Formula (A2-2) |
| 178 | F | F | F | F | 3-S"Pr | 3-S"Pr | 3-S"Pr | 3-S"Pr | Formula (A2-2) |
| 179 | F | F | F | F | 3-S"Pr | 4-S"Bu | 3-S"Pr | 4-S"Bu | Formula (A2-2) |
| 180 | F | F | F | F | 4-S"Bu | 4-S"Bu | 4-S"Bu | 4-S"Bu | Formula (A2-2) |

TABLE 46

| No. | $Q^{21}$ | $Q^{22}$ | $Q^{23}$ | $Q^{24}$ | $R^{21}$ | $R^{22}$ | $R^{23}$ | $R^{24}$ | $A^2$ |
|---|---|---|---|---|---|---|---|---|---|
| 181 | Br | Br | Br | Br | SMe | SMe | SMe | SMe | Formula (A2-2) |
| 182 | Br | Br | Br | Br | SMe | 2-SEt | SMe | 2-SEt | Formula (A2-2) |
| 183 | Br | Br | Br | Br | SMe | 3-S"Pr | SMe | 3-S"Pr | Formula (A2-2) |
| 184 | Br | Br | Br | Br | SMe | 4-S"Bu | SMe | 4-S"Bu | Formula (A2-2) |
| 185 | Br | Br | Br | Br | 2-SEt | 2-SEt | 2-SEt | 2-SEt | Formula (A2-2) |
| 186 | Br | Br | Br | Br | 2-SEt | 3-S"Pr | 2-SEt | 3-S"Pr | Formula (A2-2) |
| 187 | Br | Br | Br | Br | 2-SEt | 4-S"Bu | 2-SEt | 4-S"Bu | Formula (A2-2) |
| 188 | Br | Br | Br | Br | 3-S"Pr | 3-S"Pr | 3-S"Pr | 3-S"Pr | Formula (A2-2) |
| 189 | Br | Br | Br | Br | 3-S"Pr | 4-S"Bu | 3-S"Pr | 4-S"Bu | Formula (A2-2) |
| 190 | Br | Br | Br | Br | 4-S"Bu | 4-S"Bu | 4-S"Bu | 4-S"Bu | Formula (A2-2) |
| 191 | F | F | Cl | Cl | 3-S"Pr | 3-S"Pr | 3-S"Pr | 3-S"Pr | Formula (A2-1), n = 2, Z = NH |
| 192 | F | F | Cl | Cl | 3-S"Pr | 3-S"Pr | 3-S"Pr | 3-S"Pr | Formula (A2-1), n = 2, Z = S |
| 193 | F | F | Cl | Cl | 3-S"Pr | 3-S"Pr | 3-S"Pr | 3-S"Pr | Formula (A2-1), n = 3, Z = NH |
| 194 | F | F | Cl | Cl | 3-S"Pr | 3-S"Pr | 3-S"Pr | 3-S"Pr | Formula (A2-1), n = 3, Z = S |
| 195 | F | F | Cl | Cl | 3-S"Pr | 3-S"Pr | 3-S"Pr | 3-S"Pr | Formula (A2-3), Z = NH |
| 196 | F | F | Cl | Cl | 3-S"Pr | 3-S"Pr | 3-S"Pr | 3-S"Pr | Formula (A2-3), Z = S |
| 197 | F | F | Cl | Cl | 3-S"Pr | 3-S"Pr | 3-S"Pr | 3-S"Pr | Formula (A2-4), Z = NH |
| 198 | F | F | Cl | Cl | 3-S"Pr | 3-S"Pr | 3-S"Pr | 3-S"Pr | Formula (A2-4), Z = S |
| 199 | F | F | Cl | Cl | 3-S"Pr | 3-S"Pr | 3-S"Pr | 3-S"Pr | Formula (A2-5), Z = NH |
| 200 | F | F | Cl | Cl | 3-S"Pr | 3-S"Pr | 3-S"Pr | 3-S"Pr | Formula (A2-5), Z = S |

Preferred compounds represented by the above formula (2) include, for example, one in which in the above formula (2-1), $Q^{21}$ to $Q^{24}$ are chlorine atoms, x is 3, and $A^2$ is a 1,4-piperazinediyl group.

With regard to all components and items described above, combinations of those preferred are more preferred, and combinations of those more preferred are even more preferred. The same applies to combinations of those preferred and those more preferred and the like.

The compound represented by the above formula (2) can be manufactured as follows. It should be noted that $Q^{21}$ to $Q^{24}$, $R^{21}$ to $R^{24}$, and $A^2$ which may be used appropriately in the following formulae (20-1) to (24) each have the same meanings as defined in the above formula (2).

First, a compound represented by the following formula (20-1) obtained in accordance with the method described in Japanese Unexamined Patent Application Publication No. 2004-75719 by using 2-amino-4-halogenophenol as a raw material is converted into a methyl-ω-sulfonic acid derivative represented by the following formula (21) using sodium bisulfite and formalin. Then, the resulting methyl-ω-sulfonic acid derivative represented by the following formula (21) and a compound represented by the following formula (22) diazotized according to the conventional method are subjected to a coupling reaction at a reaction temperature of 0 to 15° C. and at pH 4 to 6. Subsequently, a hydrolysis reaction is performed at a reaction temperature of 80 to 95° C. and at pH 10.5 to 11.5 to obtain a compound represented by the following formula (23-1). Further, compounds represented by the following formulae (23-2) to (23-4) are obtained as described above except that compounds represented by the following formulae (20-2) to (20-4) are used instead of the compound represented by the following formula (20-1).

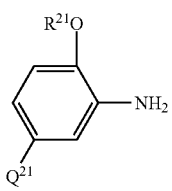

(20-1)

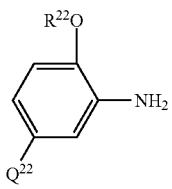

(20-2)

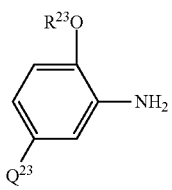

(20-3)

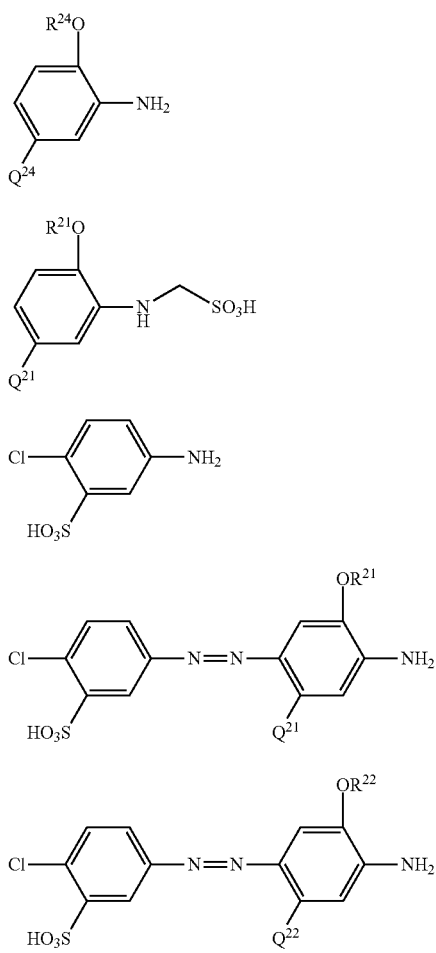

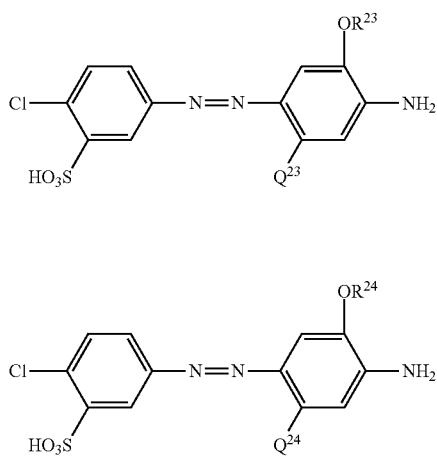

Subsequently, the compound (1 equivalent) represented by the above formula (23-1), the compound (1 equivalent) represented by the above formula (23-2), and a cyanuric halide (such as cyanuric chloride, 1 equivalent) are condensed at a reaction temperature of 15 to 45° C. and at pH 5 to 8 to obtain a compound represented by the following formula (24-1). It should be noted that one of the compounds (1 equivalent) represented by the above formula (23-1) and the compound (1 equivalent) represented by the above formula (23-2) may be reacted with a cyanuric halide (1 equivalent), and then the resulting reaction product may further be reacted with the other compound. Further, a compound represented by the following formula (24-2) is obtained as described above except that compounds represented by the above formulae (23-3) and (23-4) are used instead of the compounds represented by the above formulae (23-1) and (23-2).

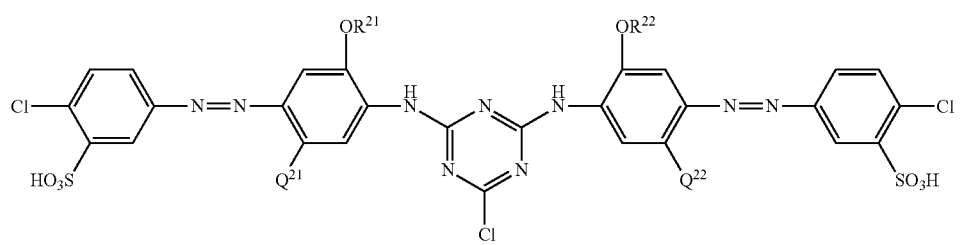

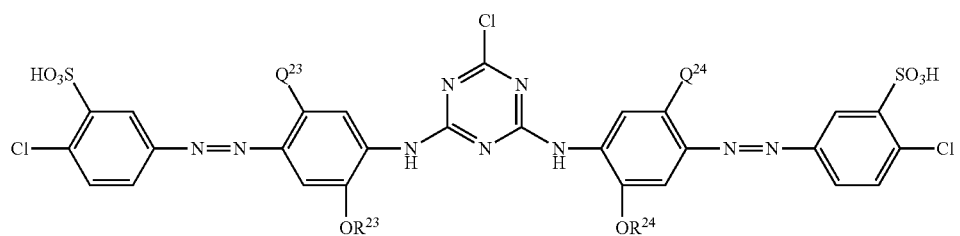

Subsequently, the compound (1 equivalent) represented by the above formula (24-1), the compound (1 equivalent) represented by the above formula (24-2), and a compound represented by a formula H-A²-H may be reacted at a reaction temperature of 55 to 95° C. and at pH 6 to 9 to cause a de-HCl reaction. This can lead to production of the compound represented by the above formula (2). It should be noted that one of the compounds (1 equivalent) represented by the above formula (24-1) and the compound (1 equivalent) represented by the above formula (24-2) may be reacted with the compound represented by the formula H-A²-H, and then the resulting reaction product may further be reacted with the other compound.

[Salt and the Like of Compound Represented by Formula (1) or (2)]

Salts of the compound represented by the above formula (1) or (2) include salts with inorganic or organic cations. Specific examples of salts with inorganic cations include alkali metal salts such as lithium salts, sodium salts, and potassium salts; ammonium salts; and the like. Specific examples of organic cations include, but are not limited to, for example, quaternary ammonium represented by the following formula (3)

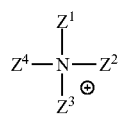

(3)

In the above formula (3), each $Z^1$ to $Z^4$ independently represents a hydrogen atom, a C1-C4 alkyl group, a hydroxy C1-C4 alkyl group, or a hydroxy C1-C4 alkoxy C1-C4 alkyl group, and at least one of $Z^1$ to $Z^4$ is a group other than a hydrogen atom.

Specific examples of the C1-C4 alkyl group in $Z^1$ to $Z^4$ include a methyl group, an ethyl group and the like. Similarly, specific examples of the hydroxy C1-C4 alkyl group include a hydroxymethyl group, a hydroxyethyl group, a 3-hydroxypropyl group, a 2-hydroxypropyl group, a 4-hydroxybutyl group, a 3-hydroxybutyl group, a 2-hydroxybutyl group and the like. Similarly, specific examples of the hydroxy C1-C4 alkoxy C1-C4 alkyl group include a hydroxyethoxymethyl group, a 2-hydroxyethoxyethyl group, a 3-(hydroxyethoxy)propyl group, a 3-(hydroxyethoxy)butyl group, a 2-(hydroxyethoxy)butyl group and the like.

Among the above salts, preferred are alkali metal salts such as sodium salts, potassium salts, lithium salts; organic quaternary ammonium salts such as monoethanolamine salts, diethanolamine salts, triethanolamine salts, monoisopropanolamine salts, diisopropanolamine salts, triisopropanolamine salts; ammonium salts; and the like. More preferred are lithium salts, sodium salts, and ammonium salts. It is generally known that a salt of a compound may be responsible for varied physical properties such as solubility and/or varied ink performances when used in an ink, depending on the type of the salt. Therefore, the type of a salt may also be preferably selected according to the target ink performance and the like. A salt of the compound represented by the above formula (1) or (2) may be any of a single salt; a mixture of a plurality of salts; a mixture of a free acid and a single or a plurality of salts; and the like.

The compound represented by the above formula (1) or (2) may be able to take various isomeric structures such as tautomers, geometrical isomers, optical isomers, and structural isomers. If that is the case, the compound represented by the above formula (1) or (2) can be used in any of these structures or under a condition where two or more of these structures are co-presented. The term "tautomer" refers to one of a set of two or more generally known isomers for one compound which can readily undergo interconversion from one to another. The term "geometrical isomer" refers to, for example, a type of generally known stereoisomers, and refers to cis-trans isomers in the case of an organic compound. The term "optical isomer" refers to, for example, a type of generally known stereoisomers, and refers to a substance having different orientations of a rotatory polarization, including a left-handed enantiomer, a right-handed enantiomer, and a racemic compound. The term "structural isomer" refers to, for example, a type of generally known isomers, and refers to a molecule having the same composition formula but a different inter-atomic bonding pattern.

[Ink]

The ink according to the present invention contains the compound represented by the above formula (1) or (2). The above ink can be prepared by dissolving the compound represented by the above formula (1) or (2) in an aqueous medium (water or a solution mixture of water and a water-soluble organic solvent), and adding an ink preparation agent, if desired.

The ink may further include a known yellow coloring matter other than the compound represented by the above formula (1) or (2) for a purpose of finely adjusting the hue thereof in a range where the effects of the present invention are not impaired. The compound represented by the above formula (1) or (2) may also be used, for example, in combination with known coloring matters of magenta, cyan and the like for a purpose of preparing various color inks such as black, red, and green.

When used as an ink-jet ink, the ink preferably has a smaller content of inorganic impurities. Inorganic impurities may be, for example, chlorides of metal cations (sodium chloride and the like), sulfates (sodium sulfate and the like) and the like. The total content of inorganic impurities may usually be 1% by mass or less relative to the total mass of the compound represented by the above formula (1) or (2), and the lower limit may be 0% by mass, i.e., less than or equal to the detection limit of a detector. Methods of reducing the content of inorganic impurities in a coloring matter include, for example, those involving purification of a coloring matter with reverse osmotic membrane, by crystallization, by suspension purification and the like.

A water-soluble organic solvent may have the following effects of: dissolving a coloring matter; preventing a composition from drying (maintaining a wet condition); adjusting the viscosity of a composition; promoting permeation of a coloring matter into a recording medium; adjusting the surface tension of a compound; defoaming a compound; and the like. Therefore, the above ink preferably contains a water-soluble organic solvent.

Examples of the above water-soluble organic solvent include, for example, C1-C4 alcohols such as methanol, ethanol, n-propanol, isopropanol, n-butanol, isobutanol, secondary butanol, tertiary butanol; amides such as N,N-dimethylformamide, N,N-dimethylacetamide; heterocyclic ketones such as 2-pyrrolidone, N-methyl-2-pyrrolidone, hydroxyethyl-2-pyrrolidone, 1,3-dimethylimidazolidin-2-one, 1,3-dimethylhexahydropyrimid-2-one; ketones or keto alcohols such as acetone, methyl ethyl ketone, 2-methyl-2-hydroxypentan-4-one; cyclic ethers such as tetrahydrofuran, dioxane; mono-, oligo- or polyalkylene glycol or thioglycol having a C2-C6 alkylene unit such as ethylene glycol, 1,2-propanediol, 1,3-propanediol, 2-methyl-1,3-propanediol, 1,2-butanediol, 1,4-butanediol, 1,2-pentanediol, 1,5-pentanediol, 1,2-hexanediol, 1,6-hexylene glycol, diethylene glycol, triethylene glycol, tetraethylene glycol, dipropylene glycol, polyethylene glycol, polypropylene glycol, thiodiglycol; polyols (preferably triols) such as trimethylolpropane, glycerin, hexane-1,2,6-triol; C1-C4 monoalkyl ethers of polyhydric alcohols such as ethylene glycol monomethyl ether, ethylene glycol monoethyl ether, diethylene glycol monomethyl ether, diethylene glycol monoethyl ether, diethylene glycol monobutyl ether (butylcarbitol), triethylene glycol monomethyl ether, triethylene glycol monoethyl ether; γ-butyrolactone; dimethyl sulfoxide; and the like.

It should be noted that a substance, for example, trimethylolpropane and the like that is solid at ambient temperature is also contained in the above water-soluble organic solvent. That is, when an aqueous solution containing a substance that is solid at ambient temperature but is water soluble has similar characteristics to those of the water-soluble organic solvents, and therefore can be used with expectation of the same effects, that substance shall fall within the category of the water-soluble organic solvents.

Such substances include, for example, solid polyhydric alcohols, saccharides, amino acids and the like.

Ink preparation agents include, for example, known additives such as antiseptic and antifungal agents, pH adjusting agents, chelating reagents, rust-preventive agents, ultraviolet absorbing agents, viscosity adjusting agents, dye-dissolving agents, anti-fading agents, surface tension adjusting agents, defoaming agents and the like.

Examples of the aforementioned antiseptic and antifungal agents include, for example, organic sulfur-based, organic nitrogen sulfur-based, organic halogen-based, haloallylsulfone-based, iodopropargyl-based, N-haloalkylthio-based, benzothiazole-based, nitrile-based, pyridine-based, 8-oxyquinoline-based, isothiazoline-based, dithiol-based, pyridinoxide-based, nitropropane-based, organic tin-based, phenol-based, quaternary ammonium salt-based, triazine-based, thiadiazine-based, anilide-based, adamantane-based, dithiocarbamate-based, brominated indanon-based, benzyl bromoacetate-based, inorganic salt-based compounds and the like. Examples of the organic halogen-based compound include, for example, sodium pentachlorophenol. Examples of the pyridinoxide-based compound include, for example, sodium 2-pyridinethiol-1-oxide. Examples of the isothiazoline-based compound include, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like. Other antiseptic and antifungal agents include sodium acetate, sodium sorbate, sodium benzoate, and Proxel™ series (Proxel™ GXL (S), Proxel™ XL-2 (S) and the like), which are product names and available from Arch Chemicals, Inc.

Any substance can be used as a pH adjusting agent as long as it can control the pH of an ink within the range between 6.0 and 11.0 for the purpose of improving the storage stability of the ink. Examples include alkanolamines such as diethanolamine, triethanolamine; hydroxides of alkali metals such as lithium hydroxide, sodium hydroxide, potassium hydroxide; ammonium hydroxide; carbonates of alkali metals such as lithium carbonate, sodium carbonate, potassium carbonate; aminosulfonic acid such as taurine; and the like.

Examples of the chelating reagent include, for example, disodium ethylenediaminetetraacetate, sodium nitrilotriacetate, sodium hydroxyethylethylenediaminetriacetate, sodium diethylenetriaminepentaacetate, sodium uracildiacetate and the like.

Examples of the rust preventive agent include, for example, hydrogen sulfite salt, sodium thiosulfate, ammonium thioglycolate, diisopropylammonium nitrite, pentaerythritol tetranitrate, dicyclohexylammonium nitrite and the like.

Examples of the ultraviolet absorbing agent include, for example, benzophenone-based compounds, benzotriazole-based compounds, cinnamic acid-based compounds, triazine-based compounds, stilbene-based compounds and the like. In addition, a compound which absorbs ultraviolet light and emits fluorescence, so-called fluorescent whitening agents, represented by benzoxazole-based compounds, can also be used.

Examples of the viscosity adjusting agent include, in addition to water-soluble organic solvents, water-soluble polymer compounds such as, polyvinyl alcohol, cellulose derivatives, polyamine, polyimine and the like.

Examples of the dye-dissolving agents include, for example, urea, s-caprolactam, ethylene carbonate and the like.

An anti-fading agent is used for the purpose of improving the preserving property of images. As the anti-fading agent, various organic and metal complex-based anti-fading agents can be used. Examples of the organic anti-fading agent include, for example, hydroquinones, alkoxyphenols, dialkoxyphenols, phenols, anilines, amines, indans, chromans, alkoxyanilines, heterocycles and the like. Examples of the metal complex-based anti-fading agent include, for example, nickel complexes, zinc complexes and the like.

Examples of the surface tension adjusting agent include surfactants. Surfactants include, for example, anionic surfactants, amphoteric surfactants, cationic surfactants, nonionic surfactants and the like.

Examples of the anionic surfactant include, for example, alkylsulfocarboxylate, α-olefin sulfonate, polyoxyethylene alkyl ether acetate, N-acylamino acid and a salt thereof, N-acylmethyltaurine salt, alkylsulfate polyoxyalkyl ether sulfate, alkylsulfate polyoxyethylene alkyl ether phosphate, rosin acid soap, castor oil sulfate ester salt, lauryl alcohol sulfate ester salt, alkylphenol-type phosphate ester, alkyl-type phosphate ester, alkylallylsulfonate, diethyl sulfosuccinate, diethylhexyl sulfosuccinate, dioctyl sulfosuccinate and the like.

Examples of the cationic surfactant include, for example, 2-vinylpyridine derivatives, poly 4-vinylpyridine derivatives and the like.

Examples of the amphoteric surfactant include, for example, lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, and in addition, imidazoline derivatives and the like.

Examples of the nonionic surfactant include, for example, those based on ether such as polyoxyethylene nonylphenyl ether, polyoxyethylene octylphenyl ether, polyoxyethylene dodecylphenyl ether, polyoxyethylene oleyl ether, polyoxyethylene lauryl ether, polyoxyethylene alkyl ether; those based on ester such as polyoxyethylene oleate ester, polyoxyethylene distearate ester, sorbitan laurate, sorbitan monostearate, sorbitan monooleate, sorbitan sesquioleate, polyoxyethylene monooleate, polyoxyethylene stearate; those based on acetylene glycols (alcohols) such as 2,4,7,9-tetramethyl-5-decyne-4,7-diol, 3,6-dimethyl-4-octyne-3,6-diol, 3,5-dimethyl-1-hexyn-3-ol; Surfynol® 104, 82, 465, Olfine® STG, which are product names and available from Nissin Chemical Industry Co., Ltd.; Tergitol® 15-S-7, which is a product name and available from SIGMA-ALDRICH; and the like.

Examples of the defoaming agent include, for example, highly oxidized oil-based compounds, glycerine fatty acid ester-based compounds, fluorine-based compounds, silicone-based compounds and the like.

The total content of the compound represented by the above formula (1) or (2) in an ink is usually 0.1 to 20% by mass relative to the total mass of the ink, preferably 1 to 10% by mass, and more preferably 2 to 8% by mass. Similarly, the content of a water-soluble organic solvent is usually 0 to 60% by mass, preferably 10 to 50% by mass. Similarly, the content of an ink preparation agent is usually 0 to 20% by mass, preferably 0 to 15% by mass. The present ink contains the compound represented by the above formula (1) or (2), and, if desired, a water-soluble organic solvent and an ink preparation agent, the remainder other than these being water.

The surface tension of the present ink is usually 25 to 70 mN/m, preferably 25 to 60 mN/m. The viscosity of the present ink is preferably 30 mPa·s or less, more preferably 20 mPa·s or less.

The present ink can be prepared by mixing each of the above components as required. There is no particular limitation for the order of adding each component. Water with little impurities such as ion exchange water, distilled water is preferably used for preparing the present ink. Further, the present ink after preparation may be subjected to precision filtration through a membrane filter and the like. When the present ink is used as an ink-jet ink, precision filtration is preferably performed for a purpose of preventing clogging of a nozzle and the like. The pore diameter of a filter used for precision filtration is usually 1 to 0.1 μm, preferably 0.8 to 0.1 μm.

The present ink may be used for various applications such as textile printing, copying, marking, writing, drawing, stamping, and recording. Among these applications, it is suitably used for ink-jet recording.

[Ink-Jet Recording Method, Ink-Jet Printer, and Recording Medium]

The ink-jet recording method according to the present invention includes discharging a droplet of the ink according to the present invention in response to a recording signal to allow for attachment to a recording medium. Ink-jet systems include, for example, piezo systems, thermal ink-jet systems and the like. The ink according to the present invention can be used as an ink-jet ink for any system.

In the ink-jet recording method according to the present invention, the ink according to the present invention may be used alone or in combination with another ink. For example, one or two or more of inks selected from magenta, cyan, green, blue (or violet), red, black and the like can also be used along with the ink according to the present invention in order to obtain full-color recorded images.

Recording media may be classified broadly into those having ink receiving layers and those having no ink receiving layers. Either of them may be preferred as recording media for use in the ink-jet recording method. Specific examples of the recording medium include, for example, paper, film, fiber or cloth (cellulose, nylon, wool and the like), leather, a substrate for a color filter and the like.

An ink receiving layer may be provided on a recording medium in order to achieve an effect of absorbing an ink for accelerated drying of the ink. An ink receiving layer may be provided, for example, by a method in which a cation-based polymer is impregnated or applied on the above recording medium; a method in which inorganic particles capable of absorbing a coloring matter in an ink is applied on a surface of a recording medium along with a hydrophilic polymer such as polyvinyl alcohol and polyvinylpyrrolidone; and the like. Inorganic particles capable of absorbing a coloring matter in an ink include porous silica, alumina sol, special ceramics and the like. A recording medium having such an ink receiving layer is commonly called an ink-jet paper, an ink-jet film, a glossy paper, a glossy film and the like. Examples of typical commercial products of recording media having ink receiving layers include: Professional photograph paper, Canon photograph paper Glossy Pro [platinum grade], and Glossy Gold, which are product names and available from Canon, Inc.; Photograph paper Crispia (high-glossy), Photograph paper (glossy), which are product names and available from Seiko Epson Corporation; Advanced photograph paper (glossy), which is a product name and available from Hewlett Packard Japan Inc.; Gasai Photo-finishing Pro, which is a product name and available from FUJIFILM Corporation; Photograph glossy Paper BP71G from Brother Industries, Ltd.; and the like.

Examples of paper having no ink receiving layer include plain paper and the like. Among the commercially available plain paper, those for ink-jet recording include Double-sided high quality plain paper (Seiko Epson Corporation); PB PAPER GF-500 (Canon, Inc.); Multipurpose Paper, All-in-one Printing Paper (Hewlett Packard); and the like. Plain paper copier (PPC) paper and the like also fall within the category of the plain paper.

Among these, a recording medium to which either
(a) the compound represented by the above formula (1) or (2) and
(b) an ink containing the compound represented by the above formula (1) or (2) is attached falls within the scope of the present invention. Further, an ink-jet printer loaded with a container containing an ink including the compound represented by the above formula (1) or (2) falls within the scope of the present invention.

With regard to all components and items described above, combinations of those preferred are more preferred, and combinations of those more preferred are even more preferred. The same applies to combinations of those preferred and those more preferred and the like.

The compound represented by the above formula (1) or (2) according to the present invention has excellent solubility in water and a solution mixture of water and a water-soluble organic solvent. Further, the ink according to the present invention is characterized by, for example, good filterability through a membrane filter. The ink according to the present invention can create extremely vivid recorded images having high color saturation and printing density with the ideal hue of yellow color when recorded on various recording media. Therefore, full-color images with photographic quality can be faithfully reproduced on a recording medium. The ink according to the present invention does not show solid precipitation, changes in physical properties, changes in a hue and the like after prolonged storage, demonstrating very good storage stability. The ink according to the present invention rarely shows solid precipitation upon drying. Therefore, the ink according to the present invention less likely causes clogging of a jetting unit (recording head) of an ink-jet printer. The ink according to the present invention does not change its physical properties even when used in a continuous ink-jet printer that uses a recirculated ink for relatively prolonged time intervals or even when used intermittently with an on-demand ink-jet printer. An image recorded on a recording medium having an ink receiving layer using the ink according to the present invention shows various aspects of roughness such as water resistance, moisture resistance, ozone gas resistance, abrasion resistance, and light resistance. In particular, it has good light resistance. This can also lead to an image recorded with photographic quality having excellent long-term storage stability. An image recorded on a recording medium having no ink receiving layer using the ink according to the present invention also shows excellent color saturation, brightness, and color-developing properties such as printing density.

EXAMPLES

Below, the present invention will be described more specifically with reference to Examples, but the present invention shall not be limited to these Examples. In Examples, the term "reaction temperature" refers to a temperature inside a reaction system. Unless otherwise specifically stated, various operations such as a reaction were all performed with stirring. Further, the term "λmax (maximal absorption wavelength)" refers to a value measured in an aqueous solution at pH 7 to 8, and was reported after being rounded off to one decimal place. It should be noted that the solubilities of the compounds according to the present invention obtained from Examples were 100 g/L or more in water at room temperature.

Example 1

(Step 1)
First, 20.8 parts of 5-amino-2-chlorobenzenesulfonic acid was dissolved in 200 parts of water while adjusting pH to 6 with sodium hydroxide, and 7.2 parts of sodium nitrite was then added. The solution was added dropwise to 200 parts of 5% hydrochloric acid over 30 minutes at 0 to 10° C., a diazotization reaction was performed with stirring at 10° C. or below for 1 hour to prepare a diazo reaction liquid.

Meanwhile, 26.6 parts of 2-(sulfopropoxy)-5-chloroaniline was dissolved in 130 parts of water while adjusting pH to 7 with sodium hydroxide, and a methyl-ω-sulfonic acid derivative was obtained by the conventional method using 10.4 parts of sodium bisulfite and 8.6 parts of 35% formalin. The resulting methyl-ω-sulfonic acid derivative was added to the diazo reaction liquid prepared above, and stirred for 24 hours under the conditions of 0 to 15° C. and pH 2 to 4. After adjusting pH to 11 with sodium hydroxide, the reaction liquid was stirred for 5 hours at 80 to 95° C. while maintaining that pH, and 100 parts of sodium chloride was added to perform salt precipitation. The resulting precipitated solid was then filtered and separated to obtain 100 parts of a compound represented by the following formula (100) as a wet cake.

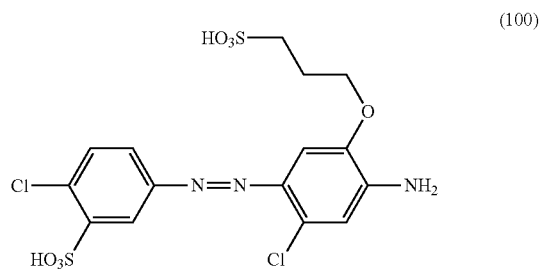 [SMILES: Nc1cc(Cl)c(N=Nc2ccc(Cl)c(S(=O)(=O)O)c2)cc1OCCCS(=O)(=O)O]

(100)

(Step 2)
To 250 parts of ice water, 0.10 parts of Leocol® TD90 (surfactant), which is a product name and available from Lion Corporation, was added and vigorously stirred. 3.6 parts of cyanuric chloride was added thereto and stirred for 30 minutes at 0 to 5° C. to obtain a suspension liquid. Subsequently, 100 parts of the wet cake of the compound represented by the above formula (100) was dissolved in 200 parts of water to obtain a solution, to which the above suspension liquid was added dropwise over 30 minutes. After the completion of the dropwise addition, it was stirred for 6 hours under the conditions of pH 6 to 8 and 25 to 45° C. To the resulting liquid, 6.2 parts of 4-amino-2-methyl-1-butanol was added, and stirred for 4 hours under the conditions of pH 7 to 9 and 75 to 90° C. After cooling the resulting reaction liquid to 20 to 25° C., 2000 parts of 2-propanol was added to this reaction liquid, and stirred for 2 hours at 20 to 25° C. The resulting precipitated solid was filtered and separated to obtain 50.0 parts of a wet cake. By drying this wet cake with an 80° C. hot-air dryer, 11.5 parts of a sodium salt of a compound according to the present invention represented by the following formula (101) (λmax: 416.6 nm) was obtained.

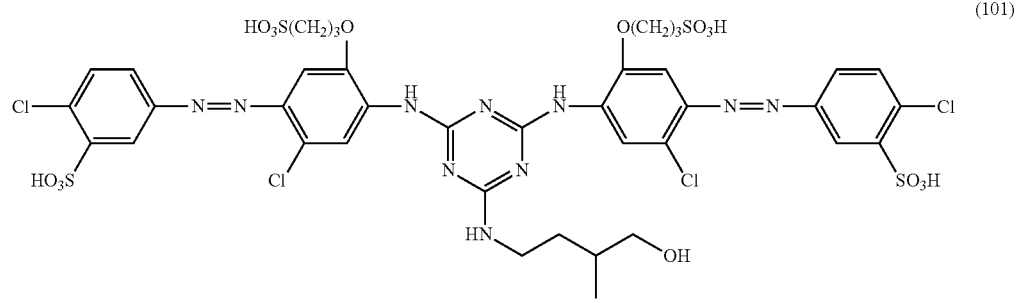

(101)

Example 2

A sodium salt of a compound according to the present invention represented by the following formula (103) (λmax: 418.4 nm) in an amount of 11.3 parts was obtained as in Example 1 except that 5.3 parts of DL-2-amino-1-butanol was used instead of 6.2 parts of 4-amino-2-methyl-1-butanol in Example 1 (Step 2).

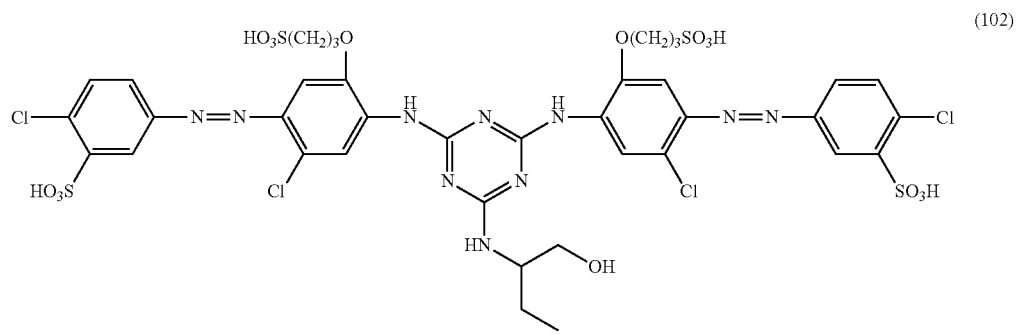

(102)

[Preparation of Ink]

Components shown in Table 47 below were mixed to obtain solutions, which were then subjected to precision filtration through 0.45 μm membrane filters to prepare inks of Examples 1, 2 and Comparative Examples 1, 2. The numerical values in the table are in terms of "parts," and the symbol "-" means that that component is not included. In Table 47 below, the component "aq. NaOH" is indicated as "remainder". This means that 25% aqueous sodium hydroxide and water were added to a liquid mixture of each component so that the resulting liquid had a total amount of 100 parts and a pH of 8.0 to 9.5.

Abbreviations in Tables 47 have the following meanings.
Formula (101): a compound represented by the above formula (101)
Formula (102): a compound represented by the above formula (102)
Formula (300): a compound represented by the following formula (300)
DY132: C.I. Direct Yellow 132
EDTA2Na: disodium ethylenediaminetetraacetate
104PG50: Surfynol 104PG50 (Air Products and Chemicals, Japan, Inc.)

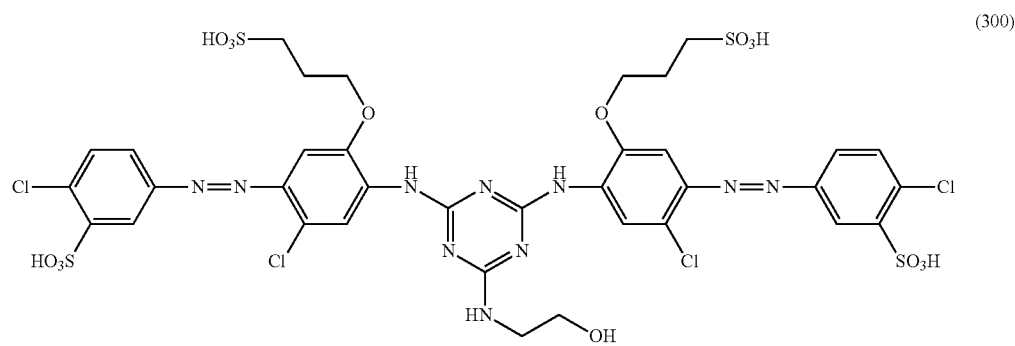 [SMILES: O=S(=O)(O)CCCOc1cc(N=Nc2ccc(Cl)c(S(=O)(=O)O)c2)c(Cl)cc1Nc1nc(NCCO)nc(Nc2cc(Cl)c(N=Nc3ccc(Cl)c(S(=O)(=O)O)c3)cc2OCCCS(=O)(=O)O)n1]

(300)

TABLE 47

| Component | Example 1 | Example 2 | Comparative Example 1 | Comparative Example 2 |
|---|---|---|---|---|
| Formula (101) | 3 | — | — | — |
| Formula (102) | — | 3 | — | — |
| Formula (300) | — | — | 3 | — |
| DY132 | — | — | — | 3 |
| Glycerin | 5 | 5 | 5 | 5 |
| Urea | 5 | 5 | 5 | 5 |
| N-methyl-2-pyrrolidone | 4 | 4 | 4 | 4 |
| Isopropyl alcohol | 3 | 3 | 3 | 3 |
| Butylcarbitol | 2 | 2 | 2 | 2 |
| Taurine | 0.3 | 0.3 | 0.3 | 0.3 |
| EDTA2Na | 0.1 | 0.1 | 0.1 | 0.1 |
| 104PG50 | 0.1 | 0.1 | 0.1 | 0.1 |
| aq. NAOH | Remainder | Remainder | Remainder | Remainder |
| Total | 100 | 100 | 100 | 100 |

[Ink-Jet Recording]

Ink-jet recording was performed with an ink-jet printer (Canon, Inc., Product name: PIXUS ip7230) to allow each of the inks from Examples 1, 2 and Comparative Examples 1, 2 to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)
Glossy paper 2: Seiko Epson Corporation, Product name: Photograph paper Crispia
Glossy paper 3: Brother Industries, Ltd., Product name: BP71G
Glossy paper 4: FUJIFILM Corporation, Product name: Gasai Photo-finishing Pro

[Color Measurements of Recorded Image]

When required, color measurements were performed for a recorded image using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 55% of each test piece was subjected to color measurements of reflection densities before and after the test. A coloring matter persistence rate was computed from the reflection densities obtained, and evaluation was performed using the following 3-grade criteria. A larger numerical value indicates a superior coloring matter persistence rate. Evaluation results are shown in Table 48 below.
(Evaluation Criteria of Light Resistance)
A coloring matter persistence rate of 85% or more: A A coloring matter persistence rate of 81% or more and less than 85%: B
A coloring matter persistence rate of less than 81%: C
(Formula for Computing Coloring Matter Persistence Rate)

Coloring matter persistence rate (%)=(reflection density after test/reflection density before test)×100

TABLE 48

| Results from light resistance tests | | Glossy paper 1 | 2 | 3 | 4 |
|---|---|---|---|---|---|
| Example | 1 | A | B | A | A |
|  | 2 | B | A | A | B |
| Comparative | 1 | B | B | B | C |
| Example | 2 | B | C | B | B |

As clearly seen in Table 48, Examples 1, 2 showed better results than Comparative Examples 1, 2 for each glossy paper in the light resistance tests.

Example 3

A sodium salt of a compound according to the present invention represented by the following formula (103) (λmax: 418.5 nm) was obtained in an amount of 11.2 parts as in Example 1 except that 4.5 parts of 2-(methylamino)ethanol was used instead of 6.2 parts of 4-amino-2-methyl-1-butanol in Example 1 (Step 2).

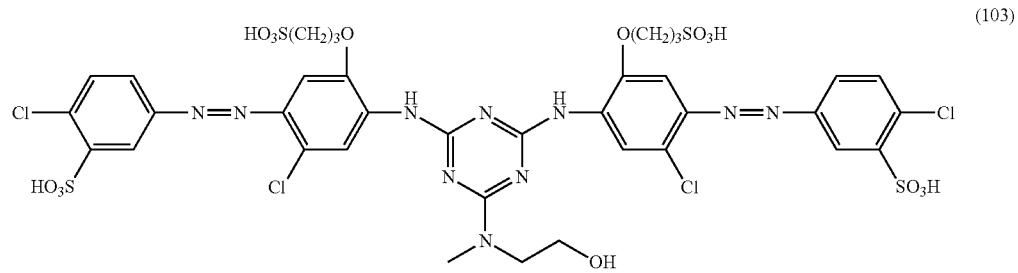

(103)

[Preparation of Ink]

An ink of Example 3 was prepared as in Example 1 except that the compound represented by the above formula (103) was used instead of the compound represented by the above formula (101).

[Ink-Jet Recording]

Ink-jet recording was performed with an ink-jet printer (Canon, Inc., Product name: PIXUS ip7230) to allow each of the inks from Example 3 and Comparative Examples 1, 2 above to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)

Glossy paper 2: Seiko Epson Corporation, Product name: Photograph paper Crispia

Glossy paper 3: Brother Industries, Ltd., Product name: BP71G

Glossy paper 4: FUJIFILM Corporation, Product name: Gasai Photo-finishing Pro

[Color Measurements of Recorded Image]

When required, color measurements were performed for a recorded image using a colorimeter (Product name SpectroEye from X-rite, Inc.). Color measurements were performed under the conditions of a density standard of DIN NB, a wide viewing angle of 2 degrees, a light source of D65.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 70% of each test piece was subjected to color measurements of reflection densities before and after the test. A coloring matter persistence rate was computed from the reflection densities obtained, and evaluation was performed using the following 4-grade criteria. A larger numerical value indicates a superior coloring matter persistence rate. Evaluation results are shown in Table 49 below.

(Evaluation Criteria of Light Resistance)

A coloring matter persistence rate of 90% or more: A

A coloring matter persistence rate of 85% or more and less than 90%: B

A coloring matter persistence rate of 81% or more and less than 85%: C

A coloring matter persistence rate of less than 81%: D (Formula for Computing Coloring Matter Persistence Rate)

Coloring matter persistence rate (%)=(reflection density after test/reflection density before test)×100

TABLE 49

| Results from light resistance tests | | Glossy paper | | | |
|---|---|---|---|---|---|
| | | 1 | 2 | 3 | 4 |
| Example | 3 | A | A | A | A |
| Comparative Example | 1 | C | B | D | B |
| | 2 | C | D | D | D |

As clearly seen in Table 49, Examples 3 showed better results than Comparative Examples 1, 2 for each glossy paper in the light resistance tests.

Example 4

(Step 1)

While adjusting pH to 7 with sodium hydroxide, 17.3 parts of 5-amino-2-chlorobenzenesulfonic acid was dissolved in 200 parts of water, and 7.2 parts of sodium nitrite was then added. This solution was added dropwise to 200 parts of 5% hydrochloric acid over 30 minutes at 0 to 10° C., a diazotization reaction was performed with stirring for 1 hour at 10° C. or below to prepare a diazo reaction liquid.

Meanwhile, 26.6 parts of 2-(sulfopropoxy)-5-chloroaniline was dissolved in 130 parts of water while adjusting pH to 7 with sodium hydroxide, and a methyl-ω-sulfonic acid derivative was obtained by the conventional method using 10.4 parts of sodium bisulfite and 8.6 parts of 35% formalin. The resulting methyl-ω-sulfonic acid derivative was added to the diazo reaction liquid prepared above, and stirred for 24 hours under the conditions of 0 to 15° C. and pH 4 to 6. After adjusting pH to 11 with sodium hydroxide, the reaction liquid was stirred for 5 hours at 80 to 95° C. while maintaining that pH, and 100 parts of sodium chloride was added to perform salt precipitation. The resulting precipitated solid was then filtered and separated to obtain 100 parts of the compound represented by the above formula (100) as a wet cake.

(Step 2)

To 250 parts of ice water, 0.10 parts of Leocol® TD90 (surfactant), which is a product name and available from Lion Corporation, was added and vigorously stirred. 3.6 parts of cyanuric chloride was added thereto and stirred for 30 minutes at 0 to 5° C. to obtain a suspension liquid. Subsequently, 100 parts of the wet cake of the compound represented by the above formula (100) was dissolved in 200 parts of water to obtain a solution, to which the above suspension liquid was added dropwise over 30 minutes. After the completion of the dropwise addition, it was stirred for 6 hours under the conditions of pH 6 to 8 and 25 to 45° C. To the resulting liquid, 3.4 parts of 3-methoxypropylamine was added, and stirred for 2 hours under the conditions of pH 7 to 9 and 75 to 90° C. After cooling the resulting reaction liquid to 20 to 25° C., 2000 parts of 2-propanol was added to this reaction liquid, and stirred for 2 hours at 20 to 25° C. The resulting precipitated solid was filtered and separated to obtain 103.3 parts of a wet cake. By drying this wet cake with an 80° C. hot-air dryer, 13.3 parts of a sodium salt of a compound according to the present invention represented by the following formula (104) (λmax: 408.0 nm) was obtained.

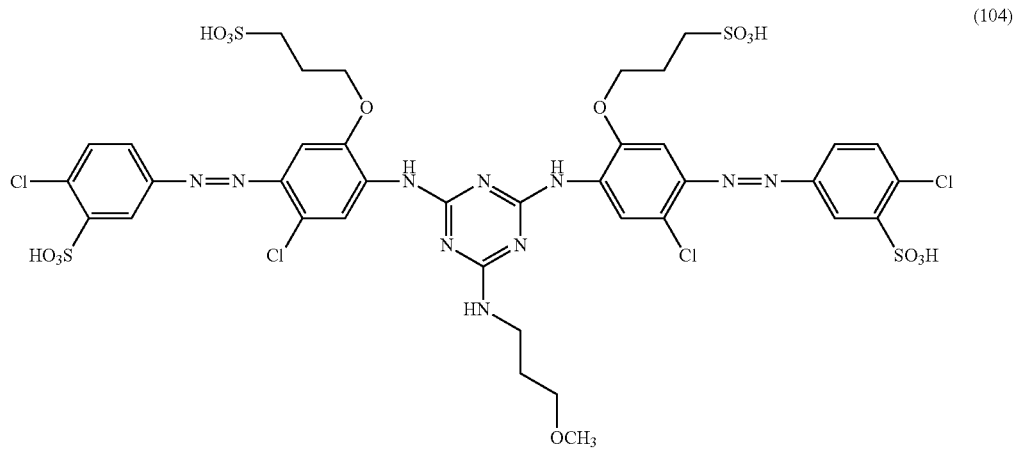 [SMILES: COCCCNc1nc(Nc2cc(Cl)c(N=Nc3ccc(Cl)c(S(=O)(=O)O)c3)cc2OCCCS(=O)(=O)O)nc(Nc2cc(Cl)c(N=Nc3ccc(Cl)c(S(=O)(=O)O)c3)cc2OCCCS(=O)(=O)O)n1]

(104)

[Preparation of Ink]

An ink of Example 4 was prepared as in Example 1 except that the compound represented by the above formula (104) was used instead of the compound represented by the above formula (101).

[Ink-Jet Recording]

Ink-jet recording was performed with an ink-jet printer (Canon, Inc., Product name: PIXUS ip7230) to allow each of the inks from Examples 4 and Comparative Examples 1, 2 above to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)
Glossy paper 2: Seiko Epson Corporation, Product name: Photograph paper Crispia
Glossy paper 3: Brother Industries, Ltd., Product name: BP71G
Glossy paper 4: FUJIFILM Corporation, Product name: Gasai Photo-finishing Pro

[Color Measurements of Recorded Image]

When required, color measurements of a recorded image were performed using a colorimeter (Product name SpectroEye from X-rite, Inc.). Color measurements were performed under the conditions of a density standard of DIN NB, a wide viewing angle of 2 degrees, a light source of D65.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 55% of each test piece was subjected to color measurements of reflection densities before and after the test. A coloring matter persistence rate was computed from the reflection densities obtained, and evaluation was performed using the following 3-grade criteria. A larger numerical value indicates a superior coloring matter persistence rate. Evaluation results are shown in Table 50 below.

(Evaluation Criteria of Light Resistance)

A coloring matter persistence rate of 85% or more: A

A coloring matter persistence rate of 81% or more and less than 85%: B

A coloring matter persistence rate of less than 81%: C (Formula for Computing Coloring Matter Persistence Rate)

Coloring matter persistence rate (%)=(reflection density after test/reflection density before test)×100

TABLE 50

| Results from light | | Glossy paper | | | |
|---|---|---|---|---|---|
| resistance tests | | 1 | 2 | 3 | 4 |
| Example | 4 | A | A | A | A |
| Comparative | 1 | B | B | B | C |
| Example | 2 | B | C | C | C |

As clearly seen in Table 50, Examples 4 showed better results than Comparative Examples 1, 2 for each glossy paper in the light resistance tests.

Example 5

A sodium salt of a compound according to the present invention represented by the following formula (105) (λmax: 419.0 nm) was obtained in an amount of 10.5 parts as in Example 1 except that 6.0 parts of 1-amino-2-propanol was used instead of 6.2 parts of 4-amino-2-methyl-1-butanol in Example 1 (Step 2).

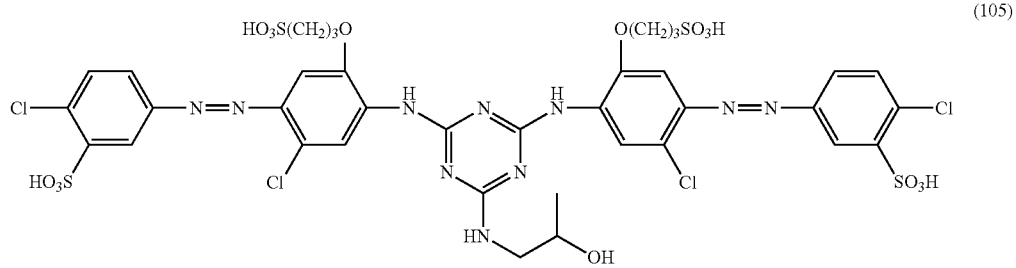

(105)

Example 6

A sodium salt of a compound according to the present invention represented by the following formula (106) (λmax: 418.0 nm) was obtained in an amount of 10.2 parts as in Example 1 except that 6.0 parts of 2-amino-1-propanol was used instead of 6.2 parts of 4-amino-2-methyl-1-butanol in Example 1 (Step 2).

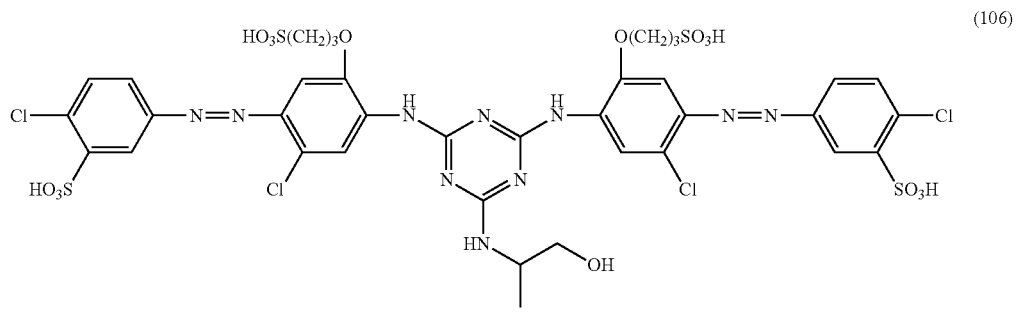

(106)

Example 7

A sodium salt of a compound according to the present invention represented by the following formula (107) (λmax: 418.5 nm) was obtained in an amount of 5.6 parts as in Example 1 except that 6.2 parts of 2-amino-2-methyl-1-propanol was used instead of 6.2 parts of 4-amino-2-methyl-1-butanol in Example 1 (Step 2).

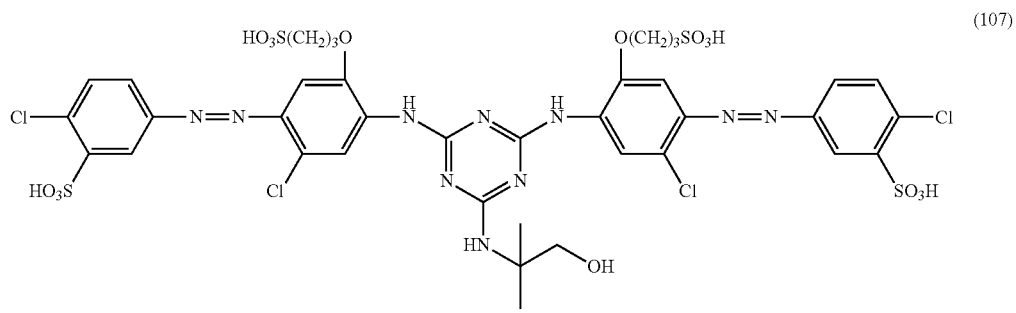

(107)

Example 8

A sodium salt of a compound according to the present invention represented by the following formula (108) (λmax: 418.5 nm) was obtained in an amount of 11.2 parts as in Example 1 except that 6.2 parts of ethoxypropylamine was used instead of 6.2 parts of 4-amino-2-methyl-1-butanol in Example 1 (Step 2).

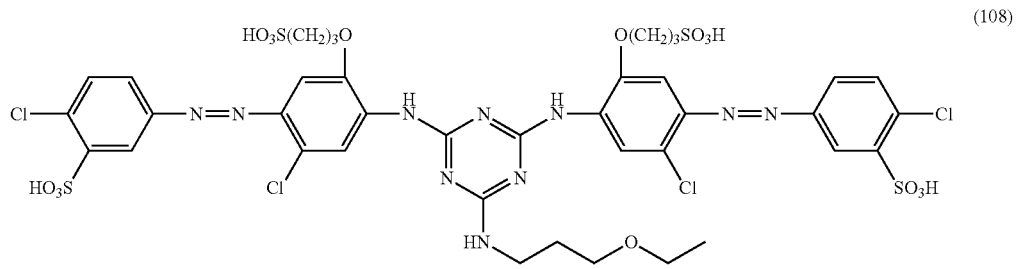

[Preparation of Ink]

Inks of Examples 5 to 8 were prepared as in Example 1 except that the compounds represented by the above formulae (105) to (108) were used, respectively, instead of the compound represented by the above formula (101).

[Ink-Jet Recording]

Ink-jet recording was performed with an ink-jet printer (Canon, Inc., Product name: PIXUS ip7230) to allow each of the inks from Examples 5 to 8 and Comparative Examples 1, 2 above to be attached on the following glossy papers 1 to 6. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)
Glossy paper 2: Canon, Inc., Product name: Canon Photograph paper, gold grade (GL-101)
Glossy paper 3: Seiko Epson Corporation, Product name: Photograph paper Crispia
Glossy paper 4: Seiko Epson Corporation, Product name: Photograph paper <glossy>
Glossy paper 5: Brother Industries, Ltd., Product name: BP71G
Glossy paper 6: FUJIFILM Corporation, Product name: Gasai Photo-finishing Pro

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 70% of each test piece was subjected to color measurements of reflection densities before and after the test. A coloring matter persistence rate was computed from the reflection densities obtained, and evaluation was performed using the following 4-grade criteria. A larger numerical value indicates a superior coloring matter persistence rate. Evaluation results are shown in Table 51 below.

(Evaluation Criteria of Light Resistance)
A coloring matter persistence rate of 90% or more: A
A coloring matter persistence rate of 85% or more and less than 90%: B
A coloring matter persistence rate of 81% or more and less than 85%: C
A coloring matter persistence rate of less than 81%: D
(Formula for Computing Coloring Matter Persistence Rate)

Coloring matter persistence rate (%)=(reflection density after test/reflection density before test)×100

TABLE 51

| Results from light resistance tests | | Glossy paper | | | | | |
|---|---|---|---|---|---|---|---|
| | | 1 | 2 | 3 | 4 | 5 | 6 |
| Example | 5 | C | B | C | B | B | B |
| | 6 | B | A | B | A | A | B |
| | 7 | C | B | B | B | C | B |
| | 8 | A | A | A | A | B | B |
| Comparative Example | 1 | C | B | C | B | C | B |
| | 2 | C | D | C | C | C | C |

As clearly seen in Table 51, Examples 5 to 8 showed better results than Comparative Examples 1, 2 for each glossy paper in the light resistance tests.

Example 9

To 250 parts of ice water, 0.10 parts of Leocol® TD90 (surfactant), which is a product name and available from Lion Corporation, was added and vigorously stirred. 3.6 parts of cyanuric chloride was added thereto and stirred for 30 minutes at 0 to 5° C. to obtain a suspension liquid. Subsequently, 100 parts of the wet cake of the compound represented by the above formula (100) was dissolved in 200 parts of water to obtain a solution, to which the above suspension liquid was added dropwise over 30 minutes. After the completion of the dropwise addition, it was stirred for 6 hours under the conditions of pH 6 to 8 and 25 to 45° C. To the resulting liquid, 5.0 parts of methylamine hydrochloride was added, and stirred for 2 hours under the conditions of pH 7 to 9 and 75 to 90° C. After cooling the resulting reaction liquid to 20 to 25° C., 2000 parts of 2-propanol was added to this reaction liquid, and stirred for 2 hours at 20 to 25° C. The resulting precipitated solid was filtered and separated to obtain 48.6 parts of a wet cake. By drying this wet cake with an 80° C. hot-air dryer, 10.9 parts of a sodium salt of a compound according to the present invention represented by the following formula (109) (λmax: 418.0 nm) was obtained.

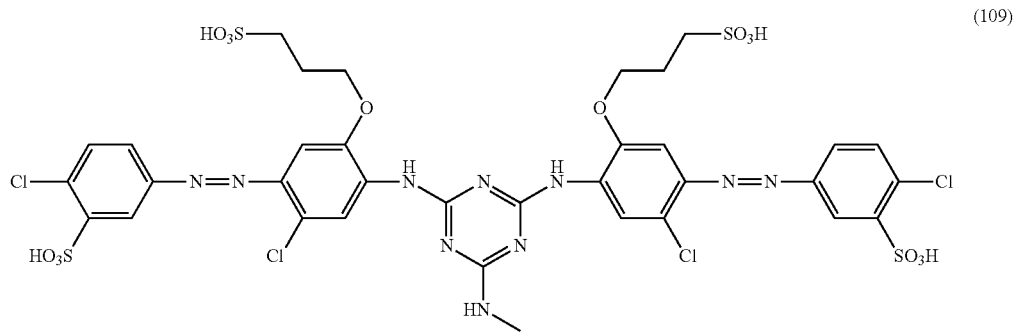 [SMILES: CNc1nc(Nc2cc(Cl)c(N=Nc3ccc(Cl)c(S(=O)(=O)O)c3)cc2OCCCS(=O)(=O)O)nc(Nc2cc(Cl)c(N=Nc3ccc(Cl)c(S(=O)(=O)O)c3)cc2OCCCS(=O)(=O)O)n1]

(109)

[Preparation of Ink]

An ink of Example 9 was prepared as in Example 1 except that the compound represented by the above formula (109) was used instead of the compound represented by the above formula (101).

[Ink-Jet Recording]

Ink-jet recording was performed with an ink-jet printer (Canon, Inc., Product name: PIXUS ip7230) to allow each of the inks from Example 9 and Comparative Examples 1, 2 above to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)

Glossy paper 2: Seiko Epson Corporation, Product name: Photograph paper Crispia

Glossy paper 3: Brother Industries, Ltd., Product name: BP71G

Glossy paper 4: FUJIFILM Corporation, Product name: Gasai Photo-Finishing Pro

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Printing Density Tests]

Yellow printing density (Dy value) was measured using the above colorimetric system for each test piece at a gradation portion where the reflection density was highest. A larger numerical value indicates superior color-developing properties. Evaluation results are shown in Table 52 below.

TABLE 52

| Results from printing | | Glossy paper | | | |
|---|---|---|---|---|---|
| density tests | | 1 | 2 | 3 | 4 |
| Example | 9 | 2.19 | 2.21 | 2.10 | 2.16 |
| Comparative | 1 | 2.14 | 2.19 | 2.07 | 2.15 |
| Example | 2 | 2.12 | 2.14 | 2.03 | 2.05 |

As clearly seen in Table 52, Example 9 showed better results than Comparative Examples 1, 2 in the yellow printing density tests (Dy value) for each glossy paper.

Example 10

To 250 parts of ice water, 0.10 parts of Leocol® TD90 (surfactant) which is a product name and available from Lion Corporation, was added and vigorously stirred. 3.6 parts of cyanuric chloride was added thereto and stirred for 30 minutes at 0 to 5° C. to obtain a suspension liquid. Subsequently, 100 parts of the wet cake of the compound represented by the above formula (100) was dissolved in 200 parts of water to obtain a solution, to which the above suspension liquid was added dropwise over 30 minutes. After the completion of the dropwise addition, it was stirred for 6 hours under the conditions of pH 6 to 8 and 25 to 45° C. To the resulting liquid, 6.0 parts of ethylamine hydrochloride was added, and stirred for 2 hours under the conditions of pH 7 to 9 and 75 to 90° C. After cooling the resulting reaction liquid to 20 to 25° C., 2000 parts of 2-propanol was added to this reaction liquid, and stirred for 2 hours at 20 to 25° C. The resulting precipitated solid was filtered and separated to obtain 49.3 parts of a wet cake. By drying this wet cake with an 80° C. hot-air dryer, 11.0 parts of a sodium salt of a compound according to the present invention represented by the following formula (110) (λmax: 416.5 nm) was obtained.

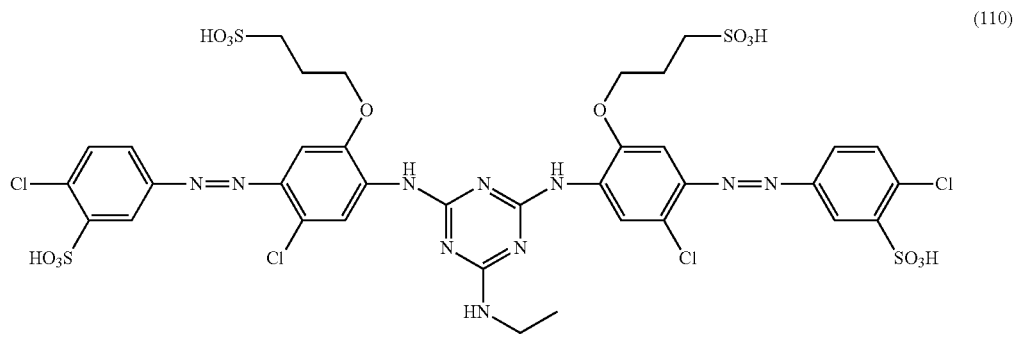 [SMILES: CCNc1nc(Nc2cc(Cl)c(N=Nc3ccc(Cl)c(S(=O)(=O)O)c3)cc2OCCCS(=O)(=O)O)nc(Nc2cc(Cl)c(N=Nc3ccc(Cl)c(S(=O)(=O)O)c3)cc2OCCCS(=O)(=O)O)n1]

(110)

Example 11

A sodium salt of a compound according to the present invention represented by the following formula (111) (λmax: 416.5 nm) was obtained in an amount of 11.2 parts as in Example 10 except that 4.4 parts of propylamine was used instead of 6.0 parts of ethylamine hydrochloride.

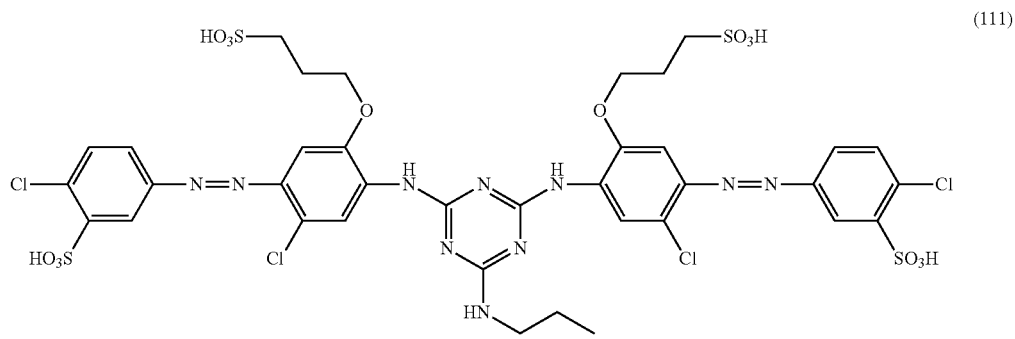 [SMILES: CCCNc1nc(Nc2cc(Cl)c(N=Nc3ccc(Cl)c(S(=O)(=O)O)c3)cc2OCCCS(=O)(=O)O)nc(Nc2cc(Cl)c(N=Nc3ccc(Cl)c(S(=O)(=O)O)c3)cc2OCCCS(=O)(=O)O)n1]

(111)

Example 12

A sodium salt of a compound according to the present invention represented by the following formula (112) (λmax: 418.0 nm) was obtained in an amount of 11.3 parts as in Example 10 except that 5.4 parts of butylamine was used instead of 6.0 parts of ethylamine hydrochloride.

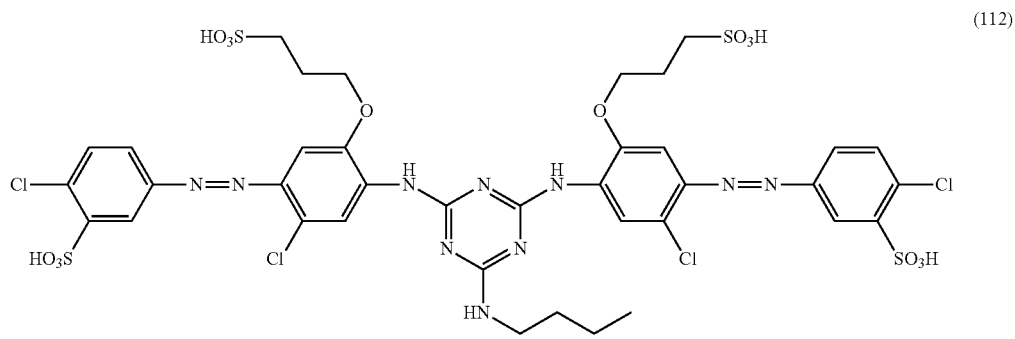 [SMILES: CCCCNc1nc(Nc2cc(Cl)c(N=Nc3ccc(Cl)c(S(=O)(=O)O)c3)cc2OCCCS(=O)(=O)O)nc(Nc2cc(Cl)c(N=Nc3ccc(Cl)c(S(=O)(=O)O)c3)cc2OCCCS(=O)(=O)O)n1]

(112)

[Preparation of Ink]

Inks of Examples 10 to 12 were prepared as in Example 1 except that the compounds represented by the above formulae (110) to (112) were used, respectively, instead of the compound represented by the above formula (101).

[Ink-Jet Recording]

Ink-jet recording was performed with an ink-jet printer (Canon, Inc., Product name: PIXUS ip7230) to allow each of the inks from Examples 10 to 12 and Comparative Examples 1, 2 above to be attached on the following glossy papers 1 to 3. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.
Glossy paper 1: Canon, Inc., Product name: Canon Photograph paper, gold grade (GL-101)
Glossy paper 2: Seiko Epson Corporation, Product name: Photograph paper Crispia
Glossy paper 3: Brother Industries, Ltd., Product name: BP71G

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 70% of each test piece was subjected to color measurements of reflection densities before and after the test. A coloring matter persistence rate was computed from the reflection densities obtained, and evaluation was performed using the following 3-grade criteria. A larger numerical value indicates a superior coloring matter persistence rate. Evaluation results are shown in Table 53 below.

(Evaluation Criteria of Light Resistance)
A coloring matter persistence rate of 85% or more: A
A coloring matter persistence rate of 81% or more and less than 85%: B
A coloring matter persistence rate of less than 81%: C (Formula for Computing Coloring Matter Persistence Rate)

Coloring matter persistence rate (%)=(reflection density after test/reflection density before test)×100

TABLE 53

| Results from light resistance tests | | Glossy paper 1 | Glossy paper 2 | Glossy paper 3 |
|---|---|---|---|---|
| Example | 10 | A | A | A |
|  | 11 | A | A | B |
|  | 12 | A | A | B |
| Comparative Example | 1 | A | B | B |
|  | 2 | C | B | B |

As clearly seen in Table 53, Example 10 showed similar results for Glossy paper 1 and better results for Glossy papers 2, 3 as compared with Comparative Example 1. Further, Example 10 showed better results for each glossy paper as compared with Comparative Example 2. Examples 11, 12 showed similar results for Glossy papers 1, 3 and better results for Glossy paper 2 as compared with Comparative Example 1. Examples 11, 12 showed similar results for Glossy paper 3 and better results for Glossy papers 1, 2 as compared with Comparative Example 2. These results demonstrate that Examples 10 to 12 have similar or better light resistance as compared with Comparative Examples 1, 2.

Example 13

A sodium salt of a compound according to the present invention represented by the following formula (113) (λmax: 416.5 nm) was obtained in an amount of 11.0 parts as in Example 10 except that 15.0 parts of 2-amino-1,3-propanediol was used instead of 6.0 parts of ethylamine hydrochloride.

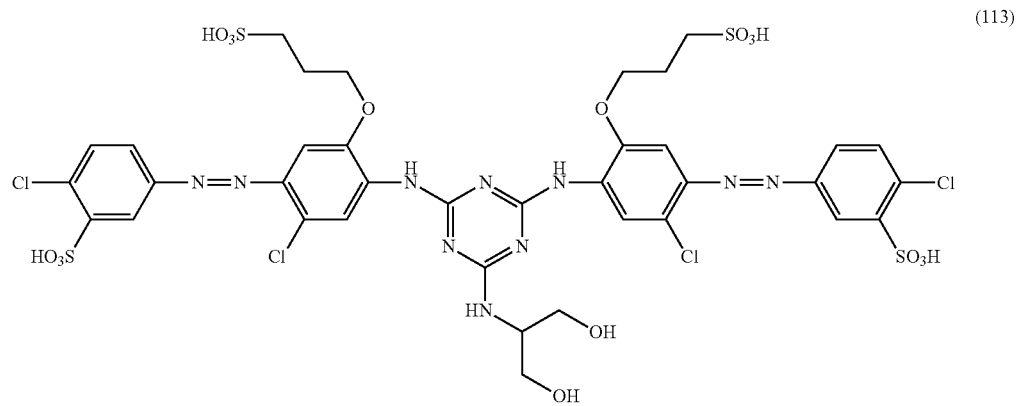 [SMILES: O=S(=O)(O)CCCOc1cc(N=Nc2ccc(Cl)c(S(=O)(=O)O)c2)c(Cl)cc1Nc1nc(Nc2cc(Cl)c(N=Nc3ccc(Cl)c(S(=O)(=O)O)c3)cc2OCCCS(=O)(=O)O)nc(NC(CO)CO)n1]

[Preparation of Ink]

An ink of Example 13 was prepared as in Example 1 except that the compound represented by the above formula (113) was used instead of the compound represented by the above formula (101).

[Ink-Jet Recording]

Ink-jet recording was performed with an ink-jet printer (Canon, Inc., Product name: PIXUS ip7230) to allow each of the inks from Example 13 and Comparative Examples 1, 2 above to be attached on the following glossy papers 1 to 3. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, gold grade (GL-101)

Glossy paper 2: Seiko Epson Corporation, Product name: Photograph paper <glossy>

Glossy paper 3: FUJIFILM Corporation, Product name: Gasai Photo-finishing Pro

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 70% of each test piece was subjected to color measurements of reflection densities before and after the test. A coloring matter persistence rate was computed from the reflection densities obtained, and evaluation was performed using the following 3-grade criteria. A larger numerical value indicates a superior coloring matter persistence rate. Evaluation results are shown in Table 54 below.

(Evaluation Criteria of Light Resistance)

A coloring matter persistence rate of 85% or more: A

A coloring matter persistence rate of 81% or more and less than 85%: B

A coloring matter persistence rate of less than 81%: C (Formula for Computing Coloring Matter Persistence Rate)

Coloring matter persistence rate (%)=(reflection density after test/reflection density before test)×100

TABLE 54

| Results from light resistance tests | | Glossy paper | | |
|---|---|---|---|---|
| | | 1 | 2 | 3 |
| Example | 13 | A | A | A |
| Comparative Example | 1 | A | B | A |
| | 2 | C | B | B |

As clearly seen in Table 54, Example 13 showed similar results for Glossy papers 1, 3 and better results for Glossy paper 2 as compared with Comparative Example 1. Further, Example 13 showed better results for each glossy paper as compared with Comparative Example 2. These results demonstrate that Example 13 has similar or better light resistance as compared with Comparative Examples 1, 2.

Example 14

A sodium salt of a compound according to the present invention represented by the following formula (114) (λmax: 422.0 nm) was obtained in an amount of 11.3 parts as in Example 1 except that 5.3 parts of 2-(ethylamino)ethanol was used instead of 6.2 parts of 4-amino-2-methyl-1-butanol in Example 1 (Step 2).

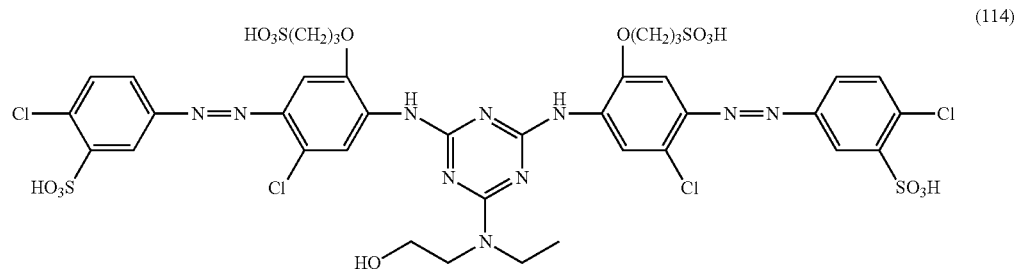

Example 15

A sodium salt of a compound according to the present invention represented by the following formula (115) (λmax: 420.5 nm) was obtained in an amount of 11.6 parts as in Example 1 except that 7.0 parts of 2-(butylamino)ethanol was used instead of 6.2 parts of 4-amino-2-methyl-1-butanol in Example 1 (Step 2).

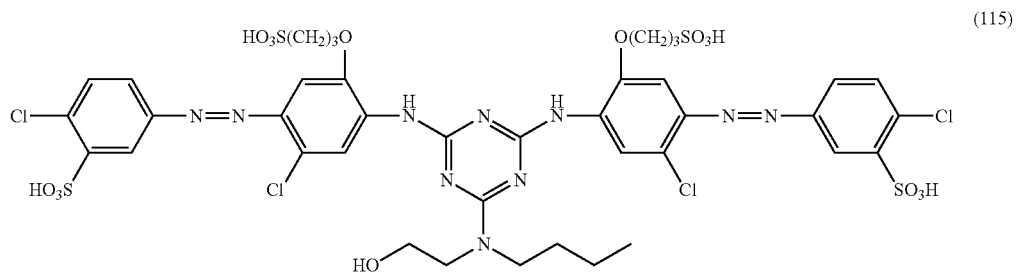

(115)

[Preparation of Ink]

Inks of Examples 14, 15 were prepared as in Example 1 except that the compounds represented by the above formulae (114), (115) were used, respectively, instead of the compound represented by the above formula (101).

[Ink-Jet Recording]

Ink-jet recording was performed with an ink-jet printer (Canon, Inc., Product name: PIXUS ip7230) to allow each of the inks from Examples 14, 15 and Comparative Examples 1, 2 above to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, gold grade (GL-101)

Glossy paper 2: Seiko Epson Corporation, Product name: Photograph paper <glossy>

Glossy paper 3: Brother Industries, Ltd., Product name: BP71G

Glossy paper 4: FUJIFILM Corporation, Product name: Gasai Photo-finishing Pro

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 70% of each test piece was subjected to color measurements of reflection densities before and after the test. A coloring matter persistence rate was computed from the reflection densities obtained, and evaluation was performed using the following 4-grade criteria. A larger numerical value indicates a superior coloring matter persistence rate. Evaluation results are shown in Table 55 below.

(Evaluation Criteria of Light Resistance)
A coloring matter persistence rate of 90% or more: A
A coloring matter persistence rate of 85% or more and less than 90%: B
A coloring matter persistence rate of 81% or more and less than 85%: C
A coloring matter persistence rate of less than 81%: D
(Formula for Computing Coloring Matter Persistence Rate)

Coloring matter persistence rate (%)=(reflection density after test/reflection density before test)×100

TABLE 55

| Results from light | | Glossy paper | | | |
|---|---|---|---|---|---|
| resistance tests | | 1 | 2 | 3 | 4 |
| Example | 14 | B | A | A | A |
|  | 15 | B | C | B | B |
| Comparative | 1 | B | C | C | C |
| Example | 2 | D | C | C | C |

As clearly seen in Table 55, Example 14 showed similar results for Glossy paper 1 and better results for Glossy papers 2 to 4 as compared with Comparative Example 1. Further, Example 14 showed good results for each glossy paper as compared with Comparative Example 2. Example 15 showed similar results for Glossy papers 1, 2 and good results for Glossy papers 3, 4 as compared with Comparative Example 1. Further, Example 15 showed similar results for Glossy paper 2 and good results for the other glossy papers as compared with Comparative Example 2. These results demonstrate that Examples 14, 15 have similar or better light resistance as compared with Comparative Examples 1, 2.

Example 16

To 250 parts of ice water, 0.10 parts of Leocol® TD90 (surfactant), which is a product name and available from Lion Corporation, was added and vigorously stirred. 3.6 parts of cyanuric chloride was added thereto and stirred for 30 minutes at 0 to 5° C. to obtain a suspension liquid. Subsequently, 100 parts of the wet cake of the compound represented by the above formula (100) was dissolved in 200 parts of water to obtain a solution, to which the above suspension liquid was added dropwise over 30 minutes. After the completion of the dropwise addition, it was stirred for 6 hours under the conditions of pH 6 to 8 and 25 to 45°

C. To the resulting liquid, 6.1 parts of tetrahydrofurfurylamine was added, and stirred for 2 hours under the conditions of pH 7 to 9 and 75 to 90° C. After cooling the resulting reaction liquid to 20 to 25° C., 2000 parts of 2-propanol was added to this reaction liquid, and stirred for 2 hours at 20 to 25° C. The resulting precipitated solid was filtered and separated to obtain 103.3 parts of a wet cake. By drying this wet cake with an 80° C. hot-air dryer, 11.4 parts of a sodium salt of a compound according to the present invention represented by the following formula (116) (λmax: 417.5 nm) was obtained.

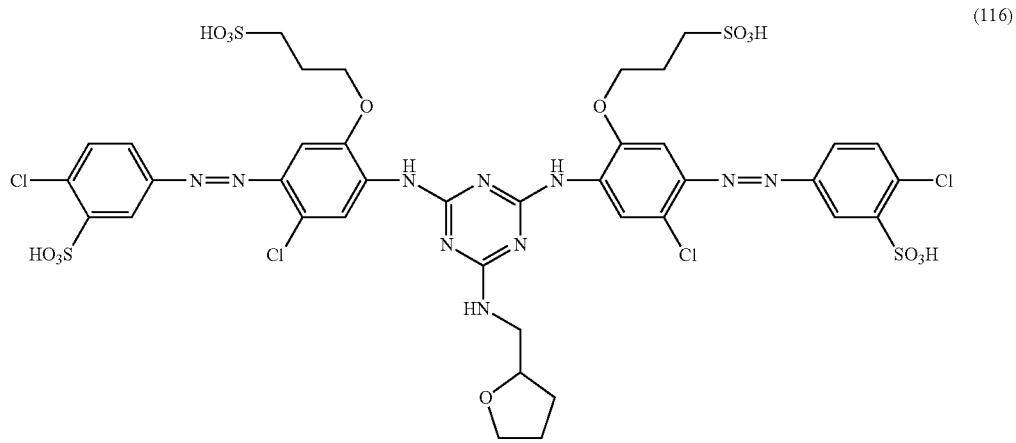 [SMILES: O=S(=O)(O)CCCOc1cc(N=Nc2ccc(Cl)c(S(=O)(=O)O)c2)c(Cl)cc1Nc1nc(NCC2CCCO2)nc(Nc2cc(Cl)c(N=Nc3ccc(Cl)c(S(=O)(=O)O)c3)cc2OCCCS(=O)(=O)O)n1]

(116)

[Preparation of Ink]

An ink of Example 16 was prepared as in Example 1 except that the compound represented by the above formula (116) was used instead of the compound represented by the above formula (101).

[Ink-Jet Recording]

Ink-jet recording was performed with an ink-jet printer (Canon, Inc., Product name: PIXUS ip7230) to allow each of the inks from Example 16 and Comparative Examples 1, 2 above to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)
Glossy paper 2: Canon, Inc., Product name: Canon Photograph paper, gold grade (GL-101)
Glossy paper 3: Seiko Epson Corporation, Product name: Photograph paper Crispia
Glossy paper 4: Brother Industries, Ltd., Product name: BP71G

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 55% of each test piece was subjected to color measurements of reflection densities before and after the test. A coloring matter persistence rate was computed from the reflection densities obtained, and evaluation was performed using the following 4-grade criteria. A larger numerical value indicates a superior coloring matter persistence rate. Evaluation results are shown in Table 56 below.

(Evaluation Criteria of Light Resistance)
A coloring matter persistence rate of 90% or more: A
A coloring matter persistence rate of 85% or more and less than 90%: B
A coloring matter persistence rate of 81% or more and less than 85%: C
A coloring matter persistence rate of less than 81%: D (Formula for Computing Coloring Matter Persistence Rate)

Coloring matter persistence rate (%)=(reflection density after test/reflection density before test)×100

TABLE 56

| Results from light resistance tests | | Glossy paper | | | |
|---|---|---|---|---|---|
| | | 1 | 2 | 3 | 4 |
| Example | 16 | B | A | B | B |
| Comparative Example | 1 | C | B | C | C |
| | 2 | C | D | C | C |

As clearly seen in Table 56, Example 16 showed good results for each glossy paper as compared with Comparative Examples 1, 2. These results demonstrate that Example 16 has superior light resistance as compared with Comparative Examples 1, 2.

Example 17

A sodium salt of a compound according to the present invention represented by the following formula (117) (λmax: 416.5 nm) was obtained in an amount of 10.5 parts as in Example 16 except that 4.0 parts of pyrrolidine was used instead of 6.1 parts of tetrahydrofurfurylamine.

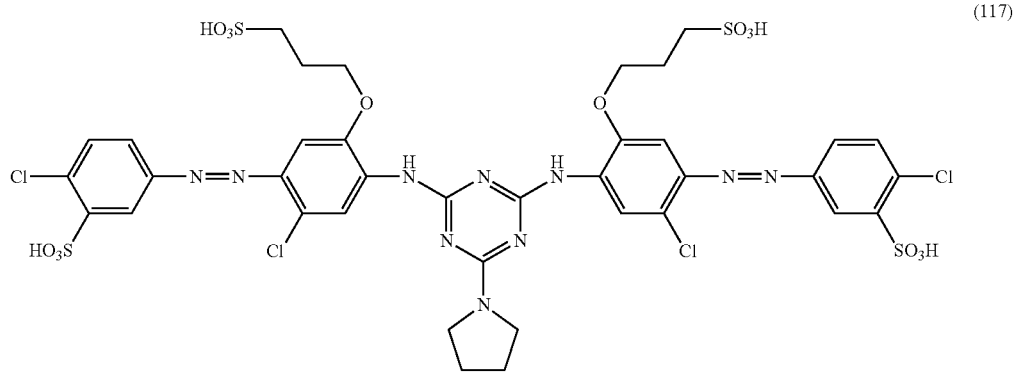 [SMILES: O=S(=O)(O)CCCOc1cc(N=Nc2ccc(Cl)c(S(=O)(=O)O)c2)c(Cl)cc1Nc1nc(Nc2cc(Cl)c(N=Nc3ccc(Cl)c(S(=O)(=O)O)c3)cc2OCCCS(=O)(=O)O)nc(N2CCCC2)n1]

(117)

[Preparation of Ink]

An ink of Example 17 was prepared as in Example 1 except that the compound represented by the above formula (117) was used instead of the compound represented by the above formula (101).

[Ink-Jet Recording]

Ink-jet recording was performed with an ink-jet printer (Canon, Inc., Product name: PIXUS ip7230) to allow each of the inks from Example 17 and Comparative Examples 1, 2 above to be attached on the following glossy papers 1, 2. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)

Glossy paper 2: FUJIFILM Corporation, Product name: Gasai Photo-finishing Pro

[Color Measurements of Recorded Image]

When required, color measurements of a recorded image were performed using a colorimeter (Product name SpectroEye from X-rite, Inc.). Color measurements were performed under the conditions of a density standard of ANSI A, a wide viewing angle of 2 degrees, a light source of D50.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 55% of each test piece was subjected to color measurements of reflection densities before and after the test. A coloring matter persistence rate was computed from the reflection densities obtained, and evaluation was performed using the following 2-grade criteria. A larger numerical value indicates a superior coloring matter persistence rate. Evaluation results are shown in Table 57 below.

(Evaluation Criteria of Light Resistance)

A coloring matter persistence rate of 85% or more: A

A coloring matter persistence rate of less than 85%: B (Formula for Computing Coloring Matter Persistence Rate)

Coloring matter persistence rate (%)=(reflection density after test/reflection density before test)×100

TABLE 57

| Results from light | | Glossy paper | |
|---|---|---|---|
| resistance tests | | 1 | 2 |
| Example | 17 | A | A |
| Comparative | 1 | B | B |
| Example | 2 | B | B |

As clearly seen in Table 57, Example 17 showed good results for each glossy paper as compared with Comparative Examples 1, 2. These results demonstrate that Example 17 has superior light resistance as compared with Comparative Examples 1, 2.

Example 18

(Step 1)

While adjusting pH to 7 with sodium hydroxide, 20.8 parts of 5-amino-2-chlorobenzenesulfonic acid was dissolved in 200 parts of water, and 7.2 parts of sodium nitrite was then added. This solution was added dropwise to 200 parts of 5% hydrochloric acid over 30 minutes at 0 to 10° C., a diazotization reaction was performed with stirring for 1 hour at 10° C. or below to prepare a diazo reaction liquid.

Meanwhile, 26.6 parts of 2-(sulfopropoxy)-5-chloroaniline was dissolved in 130 parts of water while adjusting pH to 7 with sodium hydroxide, and a methyl-ω-sulfonic acid derivative was obtained by the conventional method using 10.4 parts of sodium bisulfite and 8.6 parts of 35% formalin. The resulting methyl-ω-sulfonic acid derivative was added to the diazo reaction liquid prepared above, and stirred for 24 hours under the conditions of 0 to 15° C. and pH 4 to 6. After adjusting pH to 11 with sodium hydroxide, the reaction liquid was stirred for 5 hours at 80 to 95° C. while maintaining that pH, and 100 parts of sodium chloride was added to perform salt precipitation. The resulting precipitated solid was then filtered and separated to obtain 100 parts of the compound represented by the above formula (100) as a wet cake.

(Step 2)

To 250 parts of ice water, 0.10 parts of Leocol® TD90 (surfactant), which is a product name and available from Lion Corporation, was added and vigorously stirred. 3.6 parts of cyanuric chloride was added thereto and stirred for 30 minutes at 0 to 5° C. to obtain a suspension liquid. Subsequently, 100 parts of the wet cake of the compound represented by the above formula (100) was dissolved in 200 parts of water to obtain a solution, to which the above suspension liquid was added dropwise over 30 minutes. After the completion of the dropwise addition, it was stirred for 6 hours under the conditions of pH 6 to 8 and 25 to 45° C. To the resulting liquid, 0.9 parts of piperazine was added, and stirred for 2 hours under the conditions of pH 7 to 9 and 75 to 90° C. After cooling the resulting reaction liquid to 20 to 25° C., 2000 parts of 2-propanol was added to this reaction liquid, and stirred for 2 hours at 20 to 25° C. The resulting precipitated solid was filtered and separated to obtain 92.1 parts of a wet cake. By drying this wet cake with an 80° C. hot-air dryer, 12.0 parts of a sodium salt of a compound according to the present invention represented by the following formula (200) (λmax: 418.5 nm) was obtained.

[Color Measurements of Recorded Image]

When required, color measurements of a recorded image were performed using a colorimeter (Product name SpectroEye from X-rite, Inc.). Color measurements were performed under the conditions of a density standard of DIN NB, a wide viewing angle of 2 degrees, a light source of D65.

[Xenon Light Resistance Tests]

A test piece with a holder was placed in a xenon weatherometer XL75 (Suga Test Instruments Co., Ltd.), and irradiated for 168 hours at a temperature of 24° C., a humidity of 60% RH, and an illuminance of 100 klux. A gradation portion with a density of 70% of each test piece was subjected to color measurements of reflection densities before and after the test. A coloring matter persistence rate

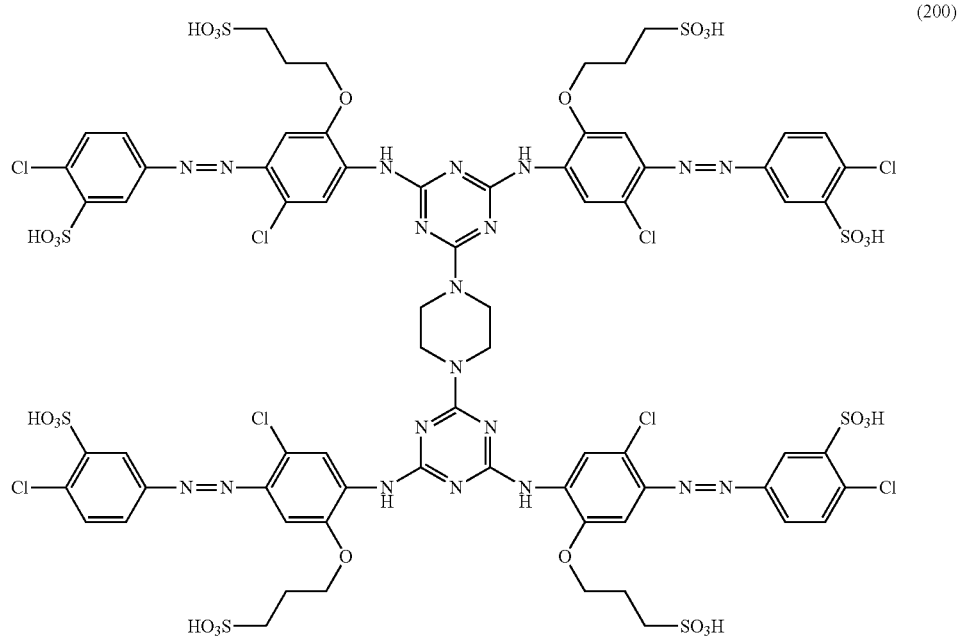 [SMILES: O=S(=O)(O)CCCOc1cc(N=Nc2ccc(Cl)c(S(=O)(=O)O)c2)c(Cl)cc1Nc1nc(Nc2cc(Cl)c(N=Nc3ccc(Cl)c(S(=O)(=O)O)c3)cc2OCCCS(=O)(=O)O)nc(N2CCN(c3nc(Nc4cc(Cl)c(N=Nc5ccc(Cl)c(S(=O)(=O)O)c5)cc4OCCCS(=O)(=O)O)nc(Nc4cc(Cl)c(N=Nc5ccc(Cl)c(S(=O)(=O)O)c5)cc4OCCCS(=O)(=O)O)n3)CC2)n1]

(200)

[Preparation of Ink]

An ink of Example 18 was prepared as in Example 1 except that the compound represented by the above formula (200) was used instead of the compound represented by the above formula (101).

[Ink-Jet Recording]

Ink-jet recording was performed with an ink-jet printer (Canon, Inc., Product name: PIXUS ip7230) to allow each of the inks from Example 18 and Comparative Examples 1, 2 above to be attached on the following glossy papers 1 to 4. Upon performing recording, image patterns were created so that the density can be obtained in a gradation of 6 levels: 100%, 85%, 70%, 55%, 40%, and 25% to obtain a half-tone recorded article. The resulting recorded article was used as a test piece to perform the following tests.

Glossy paper 1: Canon, Inc., Product name: Canon Photograph paper, platinum grade (PT-201)

Glossy paper 2: Seiko Epson Corporation, Product name: Photograph paper Crispia

Glossy paper 3: Brother Industries, Ltd., Product name: BP71G

Glossy paper 4: FUJIFILM Corporation, Product name: Gasai Photo-finishing Pro was computed from the reflection densities obtained, and evaluation was performed using the following 4-grade criteria. A larger numerical value indicates a superior coloring matter persistence rate. Evaluation results are shown in Table 58 below.

(Evaluation Criteria of Light Resistance)

A coloring matter persistence rate of 90% or more: A

A coloring matter persistence rate of 85% or more and less than 90%: B

A coloring matter persistence rate of 81% or more and less than 85%: C

A coloring matter persistence rate of less than 81%: D (Formula for Computing Coloring Matter Persistence Rate)

Coloring matter persistence rate (%)=(reflection density after test/reflection density before test)×100

TABLE 58

| Results from light | | 光沢紙 | | | |
|---|---|---|---|---|---|
| resistance tests | | 1 | 2 | 3 | 4 |
| Example | 18 | A | A | A | A |
| Comparative | 1 | C | B | D | B |
| Example | 2 | C | D | D | D |

As clearly seen in Table 58, Examples 18 showed better results than Comparative Examples 1, 2 for each glossy paper in the light resistance tests.

The invention claimed is:

1. A compound represented by the following formula (1) or (2) or a salt thereof:

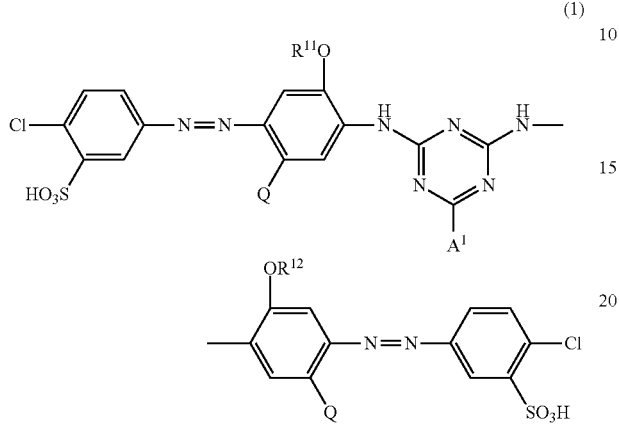

(1)

wherein, each Q independently represents a halogen atom, each $R^{11}$ and $R^{12}$ independently represents an alkyl group substituted with an ionic hydrophilic group, and $A^1$ is a group represented by the following formula (A 1-1), a group represented by the following formula (A1-2), a C1-C3 alkoxy-substituted alkylamino group, a C2-C6 alkyl-monosubstituted amino group having two or more hydroxy groups, a group represented by the following formula (A1-3), a group represented by the following formula (A1-4), or a cyclic amine group,

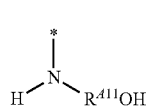

(A1-1)

wherein, $R^{411}$ represents a branched alkylene group, and the symbol "*" represents a position of attachment to a triazine ring,

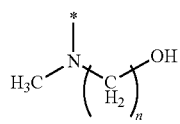

(A1-2)

wherein, n represents an integer of 1 to 6, and the symbol "*" represents a position of attachment to the triazine ring,

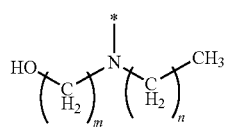

(A1-3)

wherein, m represents an integer of 1 to 6, n represents an integer of 1 to 5, and the symbol "*" represents a position of attachment to the triazine ring,

(A1-4)

wherein, n represents an integer of 2 to 6, and the symbol "*" represents a position of attachment to the triazine ring,

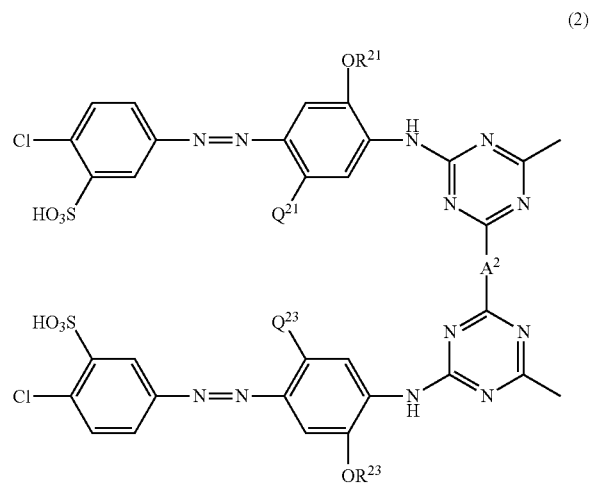

(2)

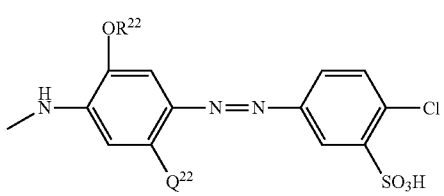

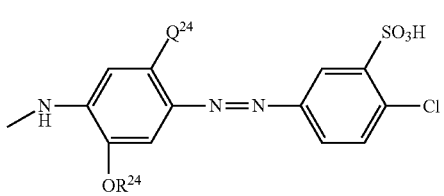

wherein, each $Q^{21}$ to $Q^{24}$ independently represents a halogen atom, and each $R^{21}$ to $R^{24}$ independently represents an alkyl group substituted with an ionic hydrophilic group, and $A^2$ represents a divalent group, wherein the compound represented by the formula (1) is represented by any of the following formulae (1-11) to (1-15):

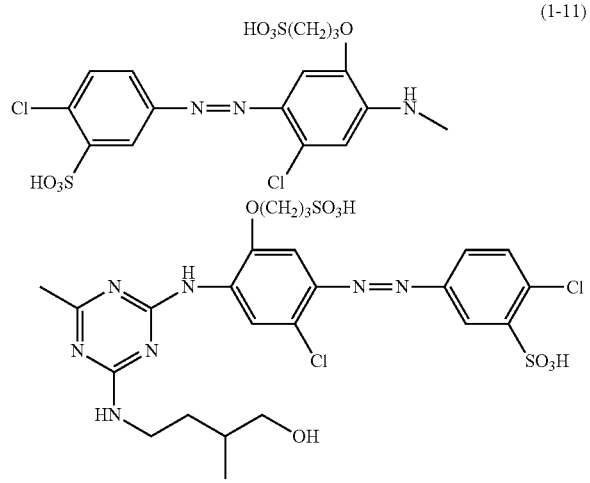

(1-11)

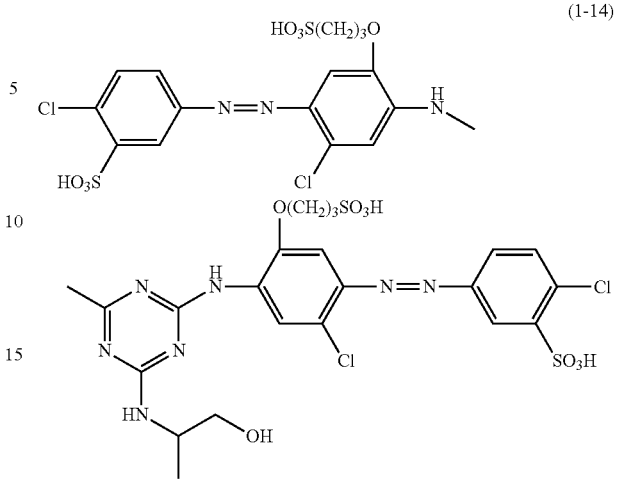

(1-14)

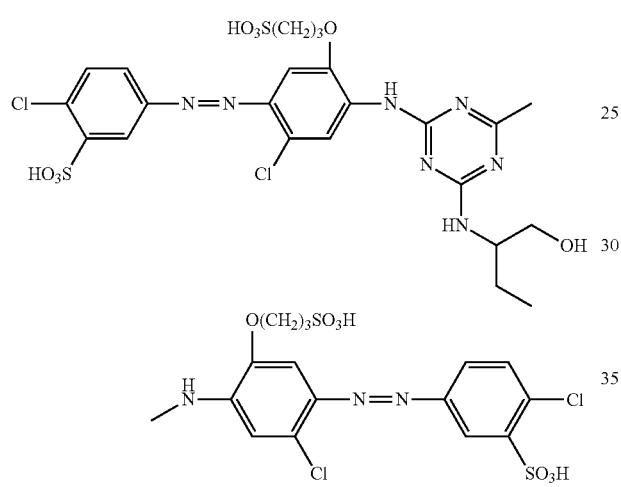

(1-12)

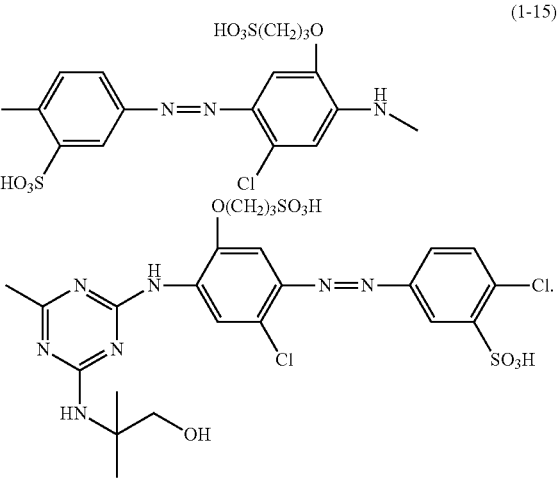

(1-15)

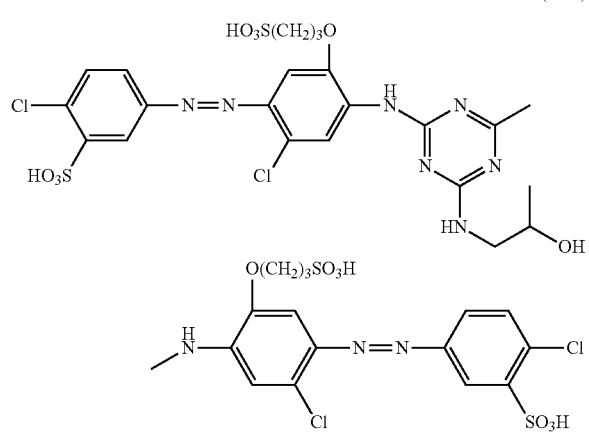

(1-13)

2. An ink comprising the compound or a salt thereof according to claim 1.

3. The ink according to claim 2, further comprising a water-soluble organic solvent.

4. An ink-jet recording method, comprising discharging a droplet of the ink according to claim 2 in response to a recording signal to allow for attachment to a recording medium.

5. The inkjet recording method according to claim 4, wherein the recording medium is plain paper or a sheet having an ink receiving layer.

6. A recording medium to which the compound or a salt thereof according to claim 1 is attached.

7. An ink-jet printer loaded with a container containing the ink according to claim 2.

8. An ink-jet printer loaded with a container containing the ink according to claim 3.

* * * * *

UNITED STATES PATENT AND TRADEMARK OFFICE
CERTIFICATE OF CORRECTION

PATENT NO. : 11,512,203 B2
APPLICATION NO. : 16/336826
DATED : November 29, 2022
INVENTOR(S) : Shinya Nagatsuka, Taku Iino and Hitomi Muto It is certified that error appears in the above-identified patent and that said Letters Patent is hereby corrected as shown below:

In the Specification

In Columns 5-6, Line 8-19 (Approx.), delete

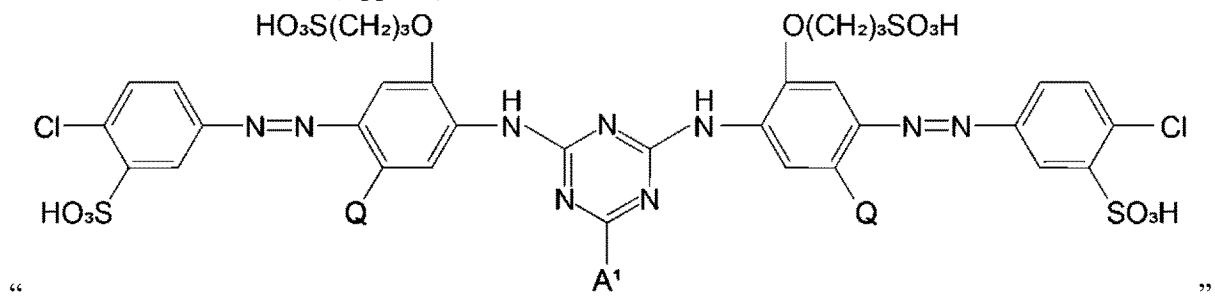

" "
and insert

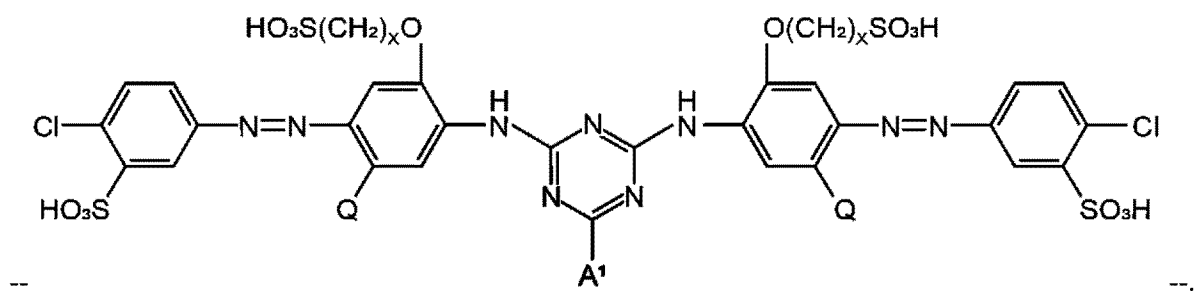

-- --.

In Column 7, Line 48 (Approx.), delete "the the" and insert --the--.

In Column 8, Line 48 (Approx.), delete "the the" and insert --the--.

In Column 19, Line 35 (Approx.), delete "n=4," and insert --n=5,--.

In Column 37, Line 35 (Approx.), delete "H" and insert --Cl--.

Signed and Sealed this
Eighth Day of August, 2023

Katherine Kelly Vidal
*Director of the United States Patent and Trademark Office*

CERTIFICATE OF CORRECTION (continued)
U.S. Pat. No. 11,512,203 B2

In Column 38, Line 19 (Approx.), delete "halogenophenol" and insert --halogenphenol--.

In Column 55, Line 4, delete "1,2-hexandiol," and insert --1,2-hexanediol,--.

In Column 55, Line 41, delete "indanon-based," and insert --indanone-based,--.

In Column 56, Line 22, delete "s-" and insert --ε- --.

In Column 56, Line 29, delete "indans," and insert --indanes,--.

In Column 59, Line 22, delete ""Amax" and insert --"λmax--.

In Column 61, Line 38, delete "that that" and insert --that--.

In Column 64, Line 14 (Approx.), after "more: A", delete "A".

In Column 64, Line 15 (Approx.), before "coloring" insert --A--.

In the Claims

In Column 89, Claim 1, Lines 30-31 (Approx.), delete "(A 1-1)," and insert --(A1-1),--.

In Column 90, Claim 1, Lines 22-57, delete

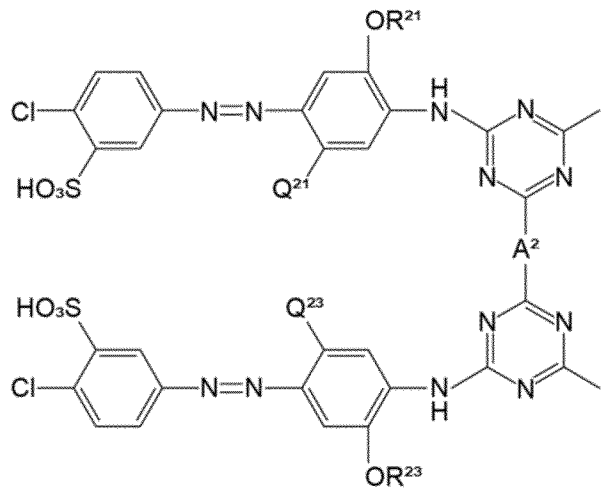

"

CERTIFICATE OF CORRECTION (continued)
U.S. Pat. No. 11,512,203 B2

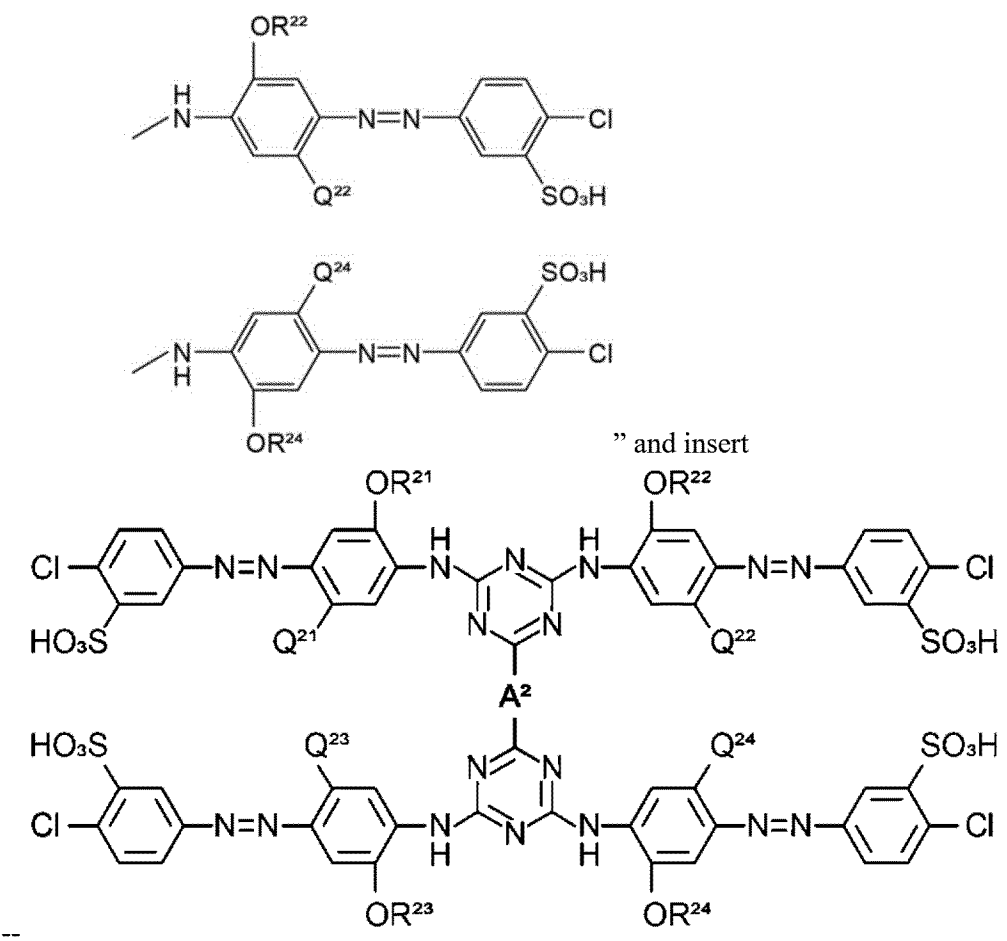

" and insert

--                    --.